(12) United States Patent
Ghaderi et al.

(10) Patent No.: US 9,273,142 B2
(45) Date of Patent: Mar. 1, 2016

(54) GLYCAN-INTERACTING COMPOUNDS

(71) Applicant: SIAMAB THERAPEUTICS, INC., Newton, MA (US)

(72) Inventors: Darius Ghaderi, Laupheim (DE); Ana Paula Galvao da Silva, San Diego, CA (US)

(73) Assignee: SIAMAB THERAPEUTICS, INC., Newton, MA (US)

( * ) Notice: Subject to any disclaimer, the term of this patent is extended or adjusted under 35 U.S.C. 154(b) by 0 days.

(21) Appl. No.: 14/050,773

(22) Filed: Oct. 10, 2013

(65) Prior Publication Data

US 2014/0178365 A1 Jun. 26, 2014

Related U.S. Application Data

(63) Continuation-in-part of application No. PCT/US2013/029240, filed on Mar. 6, 2013.

(60) Provisional application No. 61/620,414, filed on Apr. 4, 2012.

(51) Int. Cl.
*C07K 16/30* (2006.01)
*G01N 33/574* (2006.01)

(52) U.S. Cl.
CPC ......... *C07K 16/3076* (2013.01); *C07K 16/3092* (2013.01); *G01N 33/57484* (2013.01); *C07K 2317/622* (2013.01); *C07K 2317/732* (2013.01)

(58) Field of Classification Search
None
See application file for complete search history.

(56) References Cited

U.S. PATENT DOCUMENTS

| | | | |
|---|---|---|---|
| 4,179,337 A | 12/1979 | Davis et al. | |
| 4,301,144 A | 11/1981 | Iwashita et al. | |
| 4,444,887 A | 4/1984 | Hoffmann | |
| 4,474,893 A | 10/1984 | Reading | |
| 4,485,045 A | 11/1984 | Regen | |
| 4,496,689 A | 1/1985 | Mitra | |
| 4,544,545 A | 10/1985 | Ryan et al. | |
| 4,640,835 A | 2/1987 | Shimizu et al. | |
| 4,670,417 A | 6/1987 | Iwasaki et al. | |
| 4,714,681 A | 12/1987 | Reading | |
| 4,716,111 A | 12/1987 | Osband et al. | |
| 4,791,192 A | 12/1988 | Nakagawa et al. | |
| 4,816,397 A | 3/1989 | Boss et al. | |
| 4,816,567 A | 3/1989 | Cabilly et al. | |
| 4,925,648 A | 5/1990 | Hansen et al. | |
| 4,946,778 A | 8/1990 | Ladner et al. | |
| 4,965,198 A | 10/1990 | Yamasaki et al. | |
| 4,975,369 A | 12/1990 | Beavers et al. | |
| 4,978,745 A | 12/1990 | Schoemaker et al. | |
| 5,013,556 A | 5/1991 | Woodle et al. | |
| 5,045,532 A | 9/1991 | della Valle et al. | |
| 5,059,680 A | 10/1991 | Davis et al. | |
| 5,158,886 A | 10/1992 | Kawamura et al. | |
| 5,208,020 A | 5/1993 | Chari et al. | |
| 5,225,539 A | 7/1993 | Winter | |
| 5,258,498 A | 11/1993 | Huston et al. | |
| 5,403,484 A | 4/1995 | Ladner et al. | |
| 5,413,923 A | 5/1995 | Kucherlapati et al. | |
| 5,427,908 A | 6/1995 | Dower et al. | |
| 5,475,092 A | 12/1995 | Chari et al. | |
| 5,516,637 A | 5/1996 | Huang et al. | |
| 5,530,101 A | 6/1996 | Queen et al. | |
| 5,565,332 A | 10/1996 | Hoogenboom et al. | |
| 5,571,698 A | 11/1996 | Ladner et al. | |
| 5,573,920 A | 11/1996 | Randle | |
| 5,580,717 A | 12/1996 | Dower et al. | |
| 5,585,089 A | 12/1996 | Queen et al. | |
| 5,585,499 A | 12/1996 | Chari et al. | |
| 5,601,819 A | 2/1997 | Wong et al. | |
| 5,625,126 A | 4/1997 | Lonberg et al. | |
| 5,633,425 A | 5/1997 | Lonberg et al. | |
| 5,658,727 A | 8/1997 | Barbas et al. | |
| 5,693,762 A | 12/1997 | Queen et al. | |
| 5,698,426 A | 12/1997 | Huse | |
| 5,733,743 A | 3/1998 | Johnson et al. | |
| 5,750,753 A | 5/1998 | Kimae et al. | |
| 5,780,225 A | 7/1998 | Wigler et al. | |
| 5,807,715 A | 9/1998 | Morrison et al. | |
| 5,821,047 A | 10/1998 | Garrard et al. | |
| 5,846,545 A | 12/1998 | Chari et al. | |
| 5,902,725 A | 5/1999 | Robbins et al. | |

(Continued)

FOREIGN PATENT DOCUMENTS

| | | |
|---|---|---|
| EP | 0239400 | 4/1989 |
| EP | 0316818 | 5/1989 |
| EP | 0313244 | 8/1990 |
| EP | 0404097 | 10/1991 |
| EP | 0519596 | 12/1992 |
| EP | 0592106 | 4/1994 |
| VU | 9633735 | 10/1996 |
| WO | 9002809 | 3/1990 |
| WO | 9100360 | 1/1991 |
| WO | 9109967 | 7/1991 |

(Continued)

OTHER PUBLICATIONS

Kettleborough, C.A. et al., Isolation of tumor cell-specific single-chain Fv from immunized mice using phage-antibody libraries and the re-construction of whole antibodies from these antibody fragments. Eur J Imrnunol. Apr. 1994:24 (4):952-8.

(Continued)

*Primary Examiner* — Brad Duffy
*Assistant Examiner* — Nelson B Moseley, II
(74) *Attorney, Agent, or Firm* — DT Ward, PC; Donna T. Ward; Christopher P. Sullivan

(57) ABSTRACT

The present invention provides glycan-interacting antibodies useful in the treatment and prevention of human disease, including cancer. Such glycan-interacting antibodies include monoclonal antibodies, derivatives and fragments thereof as well as compositions and kits comprising them.

3 Claims, 1 Drawing Sheet

(56) References Cited

U.S. PATENT DOCUMENTS

| | | | |
|---|---|---|---|
| 5,939,598 | A | 8/1999 | Kucherlapati et al. |
| 5,969,108 | A | 10/1999 | McCafferty et al. |
| 6,075,181 | A | 6/2000 | Kucherlapati et al. |
| 6,114,598 | A | 9/2000 | Kucherlapati et al. |
| 6,300,129 | B1 | 10/2001 | Longberg et al. |
| 6,348,584 | B1 | 2/2002 | Hodgson et al. |
| 6,673,901 | B2 | 1/2004 | Koide |
| 6,852,533 | B1 | 2/2005 | Rafii et al. |
| 6,872,868 | B1 | 3/2005 | Wagner et al. |
| 7,682,794 | B2 | 3/2010 | Varki et al. |
| 7,749,225 | B2 | 7/2010 | Chappuis et al. |
| 7,994,100 | B2 | 8/2011 | Ventresca et al. |
| 8,084,219 | B2 | 12/2011 | Varki et al. |
| 8,232,448 | B2 | 7/2012 | Varki et al. |
| 8,298,773 | B2 | 10/2012 | Vuskovic et al. |
| 8,440,798 | B2 | 5/2013 | Clausen et al. |
| 8,541,231 | B2 | 9/2013 | Varki et al. |
| 2002/0012660 | A1 | 1/2002 | Colman et al. |
| 2002/0192231 | A1 | 12/2002 | Zhu et al. |
| 2007/0048314 | A1* | 3/2007 | Dai et al. .................... 424/145.1 |
| 2007/0089178 | A1 | 4/2007 | Zhu |
| 2007/0265170 | A1* | 11/2007 | Blixt et al. .................... 506/9 |
| 2008/0166805 | A1 | 7/2008 | Varki et al. |
| 2009/0099073 | A1 | 4/2009 | Rosen et al. |
| 2010/0009424 | A1 | 1/2010 | Forde et al. |
| 2010/0196983 | A1 | 8/2010 | Yang et al. |
| 2010/0221770 | A1 | 9/2010 | Varki et al. |
| 2010/0272707 | A1 | 10/2010 | Bay et al. |
| 2010/0278818 | A1 | 11/2010 | Hubert-Haddad et al. |
| 2010/0292095 | A1 | 11/2010 | Laukkanen et al. |
| 2010/0293624 | A1 | 11/2010 | Varki et al. |
| 2011/0135570 | A1 | 6/2011 | Janatpour et al. |
| 2011/0177614 | A1 | 7/2011 | Varki et al. |
| 2011/0195921 | A1 | 8/2011 | Varki et al. |
| 2012/0045816 | A1 | 2/2012 | Ghaderi et al. |
| 2012/0142903 | A1 | 6/2012 | Varki et al. |
| 2013/0039991 | A1 | 2/2013 | Varki et al. |

FOREIGN PATENT DOCUMENTS

| | | |
|---|---|---|
| WO | 9110737 | 7/1991 |
| WO | 9110741 | 7/1991 |
| WO | 92/01047 | 1/1992 |
| WO | 9201047 | 1/1992 |
| WO | 9205793 | 4/1992 |
| WO | 9208802 | 5/1992 |
| WO | 9218619 | 10/1992 |
| WO | 9311161 | 6/1993 |
| WO | 9311236 | 6/1993 |
| WO | 9317715 | 9/1993 |
| WO | 9515982 | 6/1995 |
| WO | 95/20401 | 8/1995 |
| WO | 9634096 | 10/1996 |
| WO | 9816654 | 4/1998 |
| WO | 9824893 | 6/1998 |
| WO | 9846645 | 10/1998 |
| WO | 9850433 | 11/1998 |
| WO | 02/088351 | 11/2002 |
| WO | 03/040185 | 5/2003 |
| WO | 2005/010485 | 2/2005 |
| WO | 2005/033303 | 4/2005 |
| WO | 2005/088310 | 9/2005 |
| WO | 2006/133356 | 12/2006 |
| WO | 2010030666 | 3/2010 |
| WO | 2011/088385 | 7/2011 |

OTHER PUBLICATIONS

Kilgore, B.R. et al., Comparability and monitoring immunogenic N-linked oligosaccharides from recombinant monoclonal antibodies from two different cell lines using HPLC with fluorescence detection and mass spectrometly. Methods Mol Biol. 2008;446:333-46

Kim, Y.G. et al., Hybrid restriction enzymes: zinc finger fusions to Fok 1 cleavage domain. Proc Natl Acad Sci U S A. Feb. 6, 1996;93(3):1156-60.

Kirkeby, S. et al. MUC1 and the simple mucin-type antigens: Tn and Sialyl-Tn are differently expressed in salivary gland acini and ducts from the submandibular gland, the vestibular folds, and the soft palate. Arch Oral Biol. Nov. 2010;55(11):830-41.

Kobayashi, H. et al., Serum sialyl Tn as an independent predictor of poor prognosis in patients with epithelial ovarian cancer, J Clin Oncol. Jan. 1992;10(1):95-101).

Kohler, G. et al., Continuous cultures of fused cells secreting antibody of predefined specificity. Nature, Aug. 7, 1975:256(5517):495-7.

Kostelny, S.A. et al., Formation of a bispecific antibody by the use of leucine zippers. J Immunol. Mar. 1, 1992;148 (5):1547-53).

Kozbor, D. et al., A human hybrid myeloma for production of human monoclonal antibodies. J Immunol. Dec. 1984;133(6);3001-5.

Lonberg, N. et al., Human antibodies from transgenic mice. Int Rev Immunol. 1995:13(1):65-93.

Maccioni, H.J. et al., Organization of the synthesis of glycolipid oligosaccharides in the Golgi complex. FEBS Lett. Jun. 6, 2011;585(11):1691-8.

Malphettes, L. et al., Highly efficient deletion of FUT8 in CHO cell lines using zinc-finger nucleases yields cells that produce completely nonfucosylated antibodies. Biotechnoi Bioeng. Aug. 1, 2010;106(5):774-83.

Malykh, Y.N. et al, N-Glycotylneurarninic acid in human tumours. Biochimie. 2001. 83: 623-634.

Manimala, J. et al., Carbohydrate Array Analysis of Anti-Tn Antibodies and Lectins Reveals Unexpected Specificities: Implications for Diagnostic and Vaccine Development ChemBioChem 2005, 6, 2229-2241.

Martin, F.J. et al., Irreversible coupling of immunoglobulin fragments to preformed vesicles. An improved method for liposome targeting. J Biol Chem. Jan. 10, 1982;257(1):286-8.

Massignani, et al., Cellular delivery of antibodies: effective targeted subcellular imaging and new therapeutic tool. Nature Proceedings, May 2010.

McNaughton et al., Mammalian cell penetration, siRNA transfection, and DNA transfection by supercharged proteins Proc. Natl. Acad. Sci. USA 2009 106:6111-6116.

Meng, X. et al., Targeted gene inactivation in zebrafish using engineered zinc-finger nucleases. Nat Biotechnol. Jun. 2008;26(6):695-701.

Miersch, S. et al., Synthetic antibodies: Concepts, potential and practical considerations. Methods. Aug. 2012;57(4):486-98.

Morrison, S.L., Transfectomas provide novel chimeric antibodies. Science. Sep. 20, 1985;229(4719):1202-7.

Motoo, Y. et al., Serum sialyl-Tn antigen levels in patients with digestive cancers. Oncology. 1991;48(4):321-6.

Newman and Bettinger, Gene therapy progress and prospects: ultrasound for gene transfer Gene Ther. 2007 14:465-475.

Newsom-Davis, T. et al., Enhanced immune Recognition of Cryptic Glycan Markers in Human Tumors Cancer Res 2009;69:2018-2025.

Nguyen, D.H. et al., Effects of natural human antibodies against a nonhuman sialic add that metabolically incorporates activated and malignant immune cells. J Immunol. Jul. 1, 2005;175(1):228-36.

Ogata, S. et al., Tumor-associated sialyiated antigens are constitutively expressed in normal human colonic mucosa. Cancer Res. May 1, 1995;55(9):1869-74.

Ohno, S. et al, Expression of Tn and sialyl-Tn antigens in endometrial cancer: its relationship with tumor-produced cyclooxygenase-2, tumor-infiltrated lymphocytes and patient prognosis. Anticancer Res. Nov.-Dec. 2006:26 (6A):4047-53.

Padlan, E.A. A possible procedure for reducing the immunogenicity of antibody variable domains while preserving their ligand-binding properties. Mol Immunol. Apr.-May 1991;28(4-5):489-98.

Padler-Karavani, V. et al., Diversity in specificity, abundance, and composition of anti-Neu5Gc antibodies in normal humans: potential implications for disease. Glycobiology. Oct. 2008;18(10):818-30.

Padler-Karavani, V. et al., Human xeno-autoantibodies against a non-human sialic acid serve as novel serum biomarkers and immunotherapeutics in cancer. Cancer Res. May 1, 2011;71(9):3352-63.

(56) References Cited

OTHER PUBLICATIONS

Persic, L. et al., An integrated vector system for the eukaryotic expression of antibodies or their fragments after selection from phage display libraries. Gene. Mar. 10, 1997;187(1):9-18.
Pinho, S. et al., Biological significance of cancer-associated sialyl-Tn antigen: modulation of malignant phenotype in gastric carcinoma cells. Cancer Lett. May 8, 2007:249(2):157-70.
Porteus, M.H. et al., Chimeric nucleases stimulate gene targeting in human cells. Science. May 2, 2003;300(5620):763.
Riechmann, L. et al., Reshaping human antibodies for therapy. Nature. Mar. 24, 1988;332(6162);323-7.
Roguska, M.A. et al., Humanization of murine monoclonal antibodies through variable domain resurfacing. Proc Natl Acad Sci U S A. Feb. 1, 1994;91(3):969-73.
Rozema et al., Dynamic PolyConjugates for targeted in vivo delivery of siRNA to hepatocytes Proc Natl Acad Sci U S A. 2007 104:12982-12887.
Sherwood, J.K. et al., Controlled antibody delivery systems Nature Biotechnology 10, 1446-1449 (1992).
Shu, L. et al., Secretion of a single-gene-encoded immunoglobulin from myeloma cells. Proc Natl Acad Sci U S A. Sep. 1, 1993;90(17):7995-9.
Siegwart et al., Combinatorial synthesis of chemically diverse core-shell nanoparticles for intracellular delivery Proc Natl Acad Sci U S A. 2011 108:12996-13001.
Skerra, A. et al., Assembly of a functional immunoglobulin Fv fragment in *Escherichia coli*. Science. May 20, 1988;240(4855):1038-41.
Steentoft, C. et al., Mining the O-glycoproteome using zinc-finger nuclease-glycoengineered SimpleCell lines. Nat Methods. Oct. 9, 2011;8(11):977-82.
Studnicka, G.M, et al., Human-engineered monoclonal antibodies retain full specific binding activity by preserving non-CDR complementarily-modulating residues. Protein Eng. Jun. 1994;7(6):805-14.
Takahashi et al. Immunoglobulin G3 Monoclonal Antibody Directed to Tn Antigen(Tumor-associated alpha-N-acetylgalactasaminyl Epitope) That Does Not Cross-React with Blood Group A Antigen, Cancer Res 1988;48:4361-4367.
Tangvoranuntakul, P. et al., Human uptake and incorporation of an immunogenic nonhuman dietary sialic acid. Proc Natl Aced Sci U S A. Oct. 14, 2003:100(21):12045-50.
Townsend, J.A. et al., High-frequency modification of plant genes using engineered zinc-finder nucleases. Nature. May 21, 2009:459(7245):442-5.
Tutt, A. et al., Trispecific F(ab')3 derivatves that use coopertive signaling via the TCR/CD3 complex and CD2 to activate and redirect resting cytotoxic T cells. J Immunol. Jul. 1, 1991;147(1):60-9.
Varki, A. et al., Multiple changes in sialic acid biology during human evolution. Glycoconj J. 2009. 26: 231-245.
Varki, A., Glycan-based interactions involving vertebrate sialic-acid-recognizing proteins, Nature 2007 446:1023-1029.
Varki, N.M. et al., Biomedical differences between human and non-human hominids: potential roles for uniquely human aspects of sialic acid biology. Annu Rev Pathol. 2011. 6: 365-393.
von Mensdorff-Pouilly, S., et al. Reactivity of natural and induced human antibodies to MUC1 mucin with MUC1 peptides and n-acetylgalactosamine (GalNAc) peptides Int J Cancer. Jun. 1, 2000:86(5):702-12.
Wang. D., N-glycan Cryptic Antigens as Active Immunological Targets in Prostate.
Wood, A.J. et al., Targeted genome editing across speices using ZFNs and TALENs. Science. Jul. 15, 2011;333(6040):307.
Yin, J. et al., Hypoxic culture induces expression of sialin, a sialic acid transporter, and cancer-associated gangliosides containing nonhuman sialic acid on human cancer cells. Cancer Res. Mar. 15, 2006;66(6):2937-45.
International Search Report for International Application No. PCT/US2013/029240, dated Jun. 21, 2013.
Desmetz, C. et al. (2009) "Humoral response to cancer as a tool for biomarker discovery," Journal of Proteomics 72(6), 982-988.
Diaz, A. et al., (2003) "Immune responses in breast cancer patients immunized with an anti-idiotype antibody mimicking NeuGc-containing gangliosides," Clin. Immunol. 107(2), 80-89.
Dube, D. H. and Bertozzi, C. R. (2005) "Glycans in cancer and inflammation—potential for therapeutics and diagnostics," Nature Reviews Drug Discovery 4(6), 477-488.
Finn, O. J. (2008) "Cancer Immunology," New England Journal of Medicine 358(25), 2704-2715.
Fujii, Y. et al., Specificities of human heterophilic Hanganutziu and Deicher (H-D) antibodies and avian antisera against H-D antigen-active glycosphingolipids. Mol. Immunol. vol. 19, 1982, pp. 87-94.
Greene, K. L. et al. (2009) "Prostate Specific Antigen Best Practice Statement: 2009 Update," The Journal of Urology 182(5), 2232-2241.
Heiskanen, et al., "N-Glycolylneuraminic Acid Xenoantigen Contamination of HumanEmbryonic and Mesenchymal Stem Cells is Substantially Reversible." Stem Cells, 25(1):197-202 (2007).
Higashi, et al. "Detection of Gangliosides as N-Glycolylneuraminic Acid-Specific Tumor-Associated Hanganutziu-Deicher Antigen in Human Retinoblastoma Cells." Jpn J Cancer Res,79(8):952-956 (1988).
Higashi, H. et al., Antigen of "serum sickness" type of heterophile antibodies in human sera: indentification as gangliosides with N-glycolylneuraminic acid. Biochem. Biophys. Res. Comm. vol. 79, 1977, pp. 388-395.
Hirabayashi Y et al: "Occurrence of Tumor-Associated Ganglioside Antigens With Hanganutziu-Deicher Antigenic Activity on Human Melanomas" Japanese Journal of Cancer Research, Japanese Cancer Association, Tokyo, JP, vol. 78, No. 6, Jan. 1, 1987, pp. 614-620.
Hirabayashi, et al. "Specific Expression of Unusual Gm2 Ganglioside with Hanganutziu-Deicher Antigen Activity on Human Colon Cancers." 78(3):251-260 (1987).
Juneja, L. R. et al. Large-scale preparation of sialic acid from chalaza and egg-yolk membrane. Carbohydr. Res. vol. 214, 1991, pp. 179-186.
Kasai N et al: "Preparation and specificity of avian anti-GM2(NeuGc) ganglioside antiserum", Biochemical and Biophysical Research Communications, Academic Press Inc. Orlando, FL, US, vol. 129, No. 2, Jun. 14, 1985, pp. 334-341.
Kim, G. E. et al. (2002) "Aberrant expression of MUC5AC and MUC6 gastric mucins and sialyl Tn antigen in intraepithelial neoplasms of the pancreas," Gastroenterology 123(4), 1052-1060.
Kim, Y. and Varki, A. (1997) "Perspectives on the significance of altered glycosylation of glycoproteins in cancer," Glycoconjugate Journal 14(5), 569-576.
Lee, J.-O., et al. Production of N-acetylneuraminic acid from N-acetylglucosamine and pyruvate using recombinant human renin binding protein and sialic acid aldolase in one pot. 2004. Enzyme and Microbial Technology 35(2-3): 121-125.
Lewartowska Aleksandra et al: "Ganglioside reactive antibodies of IgG and IgM class in sera of patients with differentiated thyroid cancer", Immunology Letters, vol. 80, No. 2, Feb. 1, 2002, pp. 129-132.
Lowe and Marth, "A Genetic Approach to Mammalian Glycan Function." Annu Rev Biochem,72:643-691 (2003).
Ludwig, J. A. and Weinstein, J. N. (2005) "Biomarkers in Cancer Staging, Prognosis and Treatment Selection," Nature Reviews Cancer 5(11), 845-856.
Marcial, V. A. (1977) "Carcinoma of the cervix. Present status and future," Cancer 39(Supplement S2), 945-958.
Mechref, Y. et al. (2009) "Quantitative Serum Glycomics of Esophageal Adenocarcinoma and Other Esophageal Disease Onsets," Journal of Proteome Research 8(6), 2656-2666.
Merrick, J. M.et al., Characterization of the Hanganutziu-Deicher (serum-sickness) antigen as gangliosides containing n-glycolylneuraminic acid. Int. Arch. Allergy Appl. Immunol. vol. 57, 1978, pp. 477-480.
Morito T et al. 1986. "Studies on Hanganutziu-Deicher antigens-antibodies. I. Hanganutziu-Deicher antibodies of IgG class in liver diseases", International Archives of Allergy and Applied Immunology. 81(3): 204-208.

(56) References Cited

OTHER PUBLICATIONS

Nelson, A. E. et al. (2009) "Population screening and early detection of ovarian cancer in asymptomatic women," Australian & New Zealand Journal of Obstetrics & Gynaecology 49(5), 448-450.
Nohle, U. et al. (1981) "Uptake, metabolism and excretion of orally and intravenously administered, 14C- and 3H-labeled N-acetylneuraminic acid mixture in the mouse and rat," Hoppe-Seylers Zeitschriftfur Physiologische Chemie 362(11), 1495-1506.
Nossov, V. et al. (2008) "The early detection of ovarian cancer: from traditional methods to proteomics. Can we really do better than serum CA-125?," American Journal of Obstetrics and Gynecology 199(3), 215-223.
Ogata, S. et al. (1998) "Different modes of sialyl-Tn expression during malignant transformation of human colonic mucosa," Glycoconjugate Journal 15(1), 29-35.
Parkin, D. M. et al. (2001) "Cancer burden in the year 2000. The global picture," European Journal of Cancer 37, Supplement 8(0), 4-66.
Prehn, R. T. and Prehn, L. M. (2008) "The flip side of immune surveillance: immune dependency," Immunological Reviews 222(1), 341-356.
Raedle, J. et al. (1998) "Clinical evaluation of autoantibodies to p53 protein in patients with chronic liver disease and hepatocellular carcinoma," European Journal of Cancer 34(8), 1198-1203.
Ransohoff, D. F. (2004) "Rules of evidence for cancer molecular-marker discovery and validation," Nature Reviews Cancer 4(4), 309-314.
Schauer, R. et al. (2009) "Low incidence ofN-glycolylneuraminic acid in birds and reptiles and its absence in the platypus," Carbohydrate Research 344(12), 1494-1500.
Schauer, R. Adv. Carbohydr. Chem. Biochem. vol. 40, 1982, pp. 131-234.
Shaw, L. et al. (1988) "The biosynthesis of N-glycoloylneuraminic acid occurs by hydroxylation of the CMP-glycoside of N-acetylneuraminic acid," Biological Chemistry Hoppe-Seyler 369(6), 477-486.
Stacker, S. A. et al., (1985) "A new breast carcinoma antigen defined by a monoclonal antibody," J. Natl. Cancer Inst. 75(5), 801-811.
Tan, H. T. et al. (2009) "Serum autoantibodies as biomarkers for early cancer detection," FEBS Journal 276(23), 6880-6904.
Traving and Schauer "Structure, Function and Metabolism of Sialic Acids." Cell Mol Life Sci,54(12):1330-1349 (1998).
Tzanakakis, et al., "Determination and Distribution of N-Acetyl- and N-Glycolylneuraminic Acids in Culture Media and Cell-Associated Glycoconjugates from Human Malignant Mesothelioma and Adenocarcinoma Cells." Biomed Chromatogr, 20(5):434-439 (2006).
Vamecq, J. et al., Studies on the metabolism of glycolyl-CoA. Biochem. Cell Biol. vol. 68, 1990, pp. 846-851.
van Leeuwen, P. J. et al. (2010) "Prostate cancer mortality in screen and clinically detected prostate cancer: Estimating the screening benefit," European Journal of Cancer 46(2), 377-383.
Varki, A. et al., The release and purification of sialic acids from glycoconjugates: methods to minimize the loss and migration of O-acetyl groups. Anal. Biochem. vol. 137, 1984, pp. 236-247.
Vazquez, A. M. et al., Generation of a murine monoclonal antibody specific for N-glycolylneuraminic acid-containing gangliosides that also recognizes sulfated glycolipids. Hybridoma vol. 14, 1995, pp. 551-556.
Warren, L. 1963. The Distribution of Sialic Acids in Nature. Comp. Biochem. Physiol. 10: 153-71.
Ames. R.S. et al., Conversion of murine Fabs isolated from a combinatorial phage display library to full length immunoglobulins. J Immunol Methods. Aug. 18, 1995;184(2):177-86.
Bardor, M. et al., Mechanism of uptake and incorporation of the non-human sialic acid N-glycolyineuraminic acid into human cells. J Biol Chem. 2005. 280: 4228-4237.
Benoit et al., Synthesis of folate-functionalized RAFT polymers for targeted siRNA delivery Biomacromolecules. 2011 12:2708-2714.
Bibikova, M. et al., Enhancing gene targeting with designed zinc finger nucleases. Science. May 2, 2003;300(5620):764.
Bradbury, A.R. et al., Beyond natural antibodies: the power of in vitro display technologies. Nat Biotechnol. Mar. 2011:29(3):245-54.
Brinkmann, U. et al., Phage display of disulfide-stabilized Fv fragments. J Immunol Methods. May 11, 1995;182 (1):41-50.
Brinkman-Van der Linden, E.C. et al., New aspects of siglec binding specificities, including the significance of fucosylation and of the sialyi-Tn epitope. Sialic acid-binding immunoglobulin superfamily lectins. J Biol Chem. Mar. 24, 2000;275(12):8625-32.
Brockhausen, I. et al., Pathways of mucin O-glycosylation in normal and malignant rat colonic epithelial cells reveal a mechanism for cancer-associated Sialyl-Tn antigen expression. Biol Chem, Feb. 2001;382(2):219-32.
Cao, Y. et al., Immunodetection of epithelial mucin (MUC1, MUC3) and mucin-associated glycotopes (TF, Tn, and sialosyl-Tn) in benign and malignant lesions of colonic epithelium: apolar localization corresponds to malignant transformation. Virchows Arch. 1997.
Caron et al., Intracellular delivery of a Tat-eGFP fusion protein into muscle cells Mol. Ther. 3(3):310-8 (2001).
Carroll, D., Progress and prospects: zinc-finger nucleases as gene therapy agents. Gene Ther. Nov. 2008;15(22):1463-8.
Cathomen, T. et al. Zinc-finger nuceases: the next generation emerges. Mol Ther. Jul. 2008;16(7)1200-7.
Chao, G. et al., Isolating and engineering human antibodies using yeast surface display. Nat Protoc. 2006;1(2):755-68.
Cheever, M.A. et al., The prioritization of cancer antigens: a national cancer institute pilot project for the acceleraton of translational research. Clin Cancer Res. Sep. 1, 2009;15(17):5323-37.
Chen, X. et al., Advances in the biology and chemistry of sialic acids. ACS Chem Biol. Feb. 19, 2010;5(2):163-76.
Chung, C.H. et al., Cetuximab-induced anaphylaxis and IgE specific for galactose-alpha-1,3-galactose. N Engl J Med. Mar. 13, 2008;358(11):1109-17.
Cronican et al., Potent delivery of functional proteins into Mammalian cells in vitro and in vivo using a supercharged protein ACS Chem. Biol. 2010 5:747-752.
Daugherty, et al., Formulation and delivery issues for monoclonal antibody therapeutics. Adv Drug Deliv Rev. Aug. 7, 2006;58(5-6):686-706.
Davis et al. Evidence of RNAi in humans from systemically administered siRNA via targeted nanoparticles Nature 2010 464:1067-1070.
Davis, M.E. The first targeted delivery of siRNA in humans via a self-assembling, cyclodextrin polymer-based nanoparticle: from concept to clinic Mol Pharm. 2009 6:659-668.
Deshayes et al., Cell-penetrating peptides: tools for intracellular delivery of therapeutics. Cell. Mol. Life Sci. 62 (16):1839-49 (2005).
Devine, P.L. et al., The breast tumor-associated epitope defined by monoclonal antibody 3E1.2 is an O-linked mucin carbohydrate containing N-glycolylneuraminic acid. Cancer Res. 1991. 51: 5826-5836.
Dharmawardhane, S. et al., Regulation of macropinocytosis by p21-activated kinase-1. Mol Biol Cell. Oct. 2000;11 (10):3341-52.
Diaz, S.L. et al., Sensitive and specific detection of the non-human sialic Acid N-glycolylneuraminic acid in human tissues and biotherapeutic products. PLoS One. 2009. 4; e4241.
Doyon, Y. et al., Heritable targeted gene disruption in zebrafish using designed zinc-finger nucleases, Nat Biotechnol. Jun. 2008;26(6):702-8.
El-Andaloussi et al., Cell-penetrating peptides: mechanisms and applications Curr. Pharm. Des. 11(28):3597-611(2003).
Eppstein D.A. et al., Biological activity of liposome-encapsulated murine interferon gamma is mediated by a cell membrane receptor. Proc Natl Acad Sci U S A. Jun. 1985;82(11):3688-92.
Geurts, A.M. et al., Knockout rats via embryo microinjection of zinc-finger nucleases. Science. Jul. 24, 2009;325(5939):433.
Ghaderi, D. et al., Implications of the presence of N-glycolylneuraminic acid in recombinant therapeutic glycoproteins. Nat Biotechnol. 2010. 28: 863-867.
Gillies, S.D. et al., High-level expression of chimeric antibodies using adapted cDNA variable region cassettes. J lmmunol Methods. Dec. 20, 1989;125(1-2):191-202.

(56) References Cited

OTHER PUBLICATIONS

Hedlund, M. et al., Evidence for a human-specific mechanism for diet and antibody-mediated inflammation in carcinoma progression. Proc Natl Acad Sci U S A. Dec. 2, 2008;105(48):18936-41.

Heimburg-Molinaro, J. et al., Cancer vaccines and carbohydrate epitopes. Vaccine. Nov. 8, 2011;29(48):8802-26.

Higashi, H. et al., Characterization of N-glycolylneuraminic acid-containing gangliosides as tumor-associated Hanganutziu-Deicher antigen in human colon cancer . . . Cancer Res. Aug. 1985;45(8):3796-802.

Hojman, Basic principles and clinical advancements of muscle electrotransfer Curr Gene Thar. 2010 10:128-138.

Hollinger et al., Proc. Natl. Acad. Sci, USA, 90:6444-6448 (1993).

Huston, J.S. et al., Protein engineering of single-chain Fv analogs and fusion proteins. Methods Enzymol. 1991:203:46-88.

Hwang, K.J. et al., Hepatic uptake and degradation of unilamellar sphingomyelin/cholesterol liposomes: a kinetic study. Proc Natl Acad Sci U S A. Jul. 1980;77(7):4030-4.

Ikehara, Y. et al., Cloning and expression of a human gene encoding an N-acetylgalactosamine-alpha2,6-sialyltransferase (ST6GalNAc 1): a candidate for synthesis of cancer-associated sialyl-Tn antigens. Glycobiology. Nov. 1999;9(11):1213-24.

Itzkowitz, S.H. et al., Sialosyl-Tn. A novel mucin antigen associated with prognosis in colorectal cancer patients. Cancer. Nov. 1, 1990;66(9):1960-6.

Jess, J.R. et al., Distribution of sialosyl Tn and Tn antigens within normal and malignant colorectal epithelium. J Pathol. Jun. 1995;176(2):143-9.

Johannes, L. et al., Clathrin-dependent or not: is it still the question? Traffic. Jul. 2002:3(7):443-51.

Ju, T. et al., Human tumor antigens Tn and sialyl Tn arise from mutations in Cosmc, Cancer Res. Mar. 15, 2008;68(6):1636-46.

Ju, T et al., Protein glycosylation: chaperone mutation in Tn syndrome. Nature. Oct. 27, 2005;437(7063):1252.

Julien S. et al. Sialyl-Tn in Cancer: (How) Did We Miss the Target? Biomolecules 2012,2, 435-466.

Julien S. et al. Stable expression of sialyl-Tn antigen in T47-D cells induces a decrease of cell adhesion and an increase of cell migration Breast Cancer Research and Treatment (2005) 90: 77-84.

Julien, S. et al., Sialyl-Tn vaccine induces antibody-mediated tumour protection in a relevant murine model. Br J Cancer. Jun. 2, 2009;100(11):1746-54.

Karlen, P. et al., Sialyl-Tn antigen as a marker of colon cancer risk in ulcerative colitis: relation to dysplasia and DNA aneuploidy. Gastroenterology. Dec. 1998;115(6):1395-404.

Kawachi. S, et al., Heterophile Hanganutziu-Deicher antigen in ganglioside fractions of human melanoma tissues. Int Arch Allergy Appl Immunol. 1988. 85: 381-383.

Zhu et al. Anti-N-glycolylneuraminic acid antibodies identified in healthy human serum. Xenotransplantation. 2002 vol. 9: 376-81.

An, H. J . et al. (2009) Glycomics and disease markers. Current Opinion in Chemical Biology 13(5-6), 601-607.

Andreu P; Johansson M; Affara NI et al.: FcRgamma activation regulates inflammation-associated squamous carcinogenesis' Cancer Cell vol. 17, 2010, pp. 121-134.

Bergfeld, A. K. et al. (2012) "Metabolism of Vertebrate Amino Sugars with N-Glycolyl Groups: Elucidating the Intracellular Fate of the Non-Human Sialic Acid N-Glycolylneuraminic Acid," Journal of Biological Chemistry 287(34), 28865-28881.

Bork et al, 2009, Increasing the Sialylation of Therapeutic Glycoproteins: The Potential of the Sialic Acid Biosynthetic Pathway. Journal of Pharmaceutical Sciences. 98(10):3499-508.

Brinkman-Vander Linden, Els C. M.; E. R. Sjoberg; L. R. Juneha; P. R. Crocker; N. Varki; and A Varki; "Loss of N-Glycolylneuraminic Acid in Human Evolution"; The Journal of Biological Chemistry; Mar. 24, 2000, vol. 275, No. 12. pp. 8633-8640.

Carlson, D. M. et al. (1968) "Structures and Immunochemical Properties of Oligosaccharides Isolated from Pig Submaxillary Mucins," Journal of Biological Chemistry 243(3), 616-626.

Chou, et al. "A Mutation in Human Cmp-Sialic Acid Hydroxylase Occurred after the Homo-Pan Divergence." Proceedings of the National Academy of Sciences, 95(20):11751-11756 (1998).

Chou, et al. "Inactivation of Cmp-N-Acetylneuraminic Acid Hydroxylase Occurred Prior to Brain Expansion During Human Evolution." Proc Natl Acad Sci U S A, 99(18):11736-11741 (2002).

Collins, Brian E.; T. J. Fralich; S. Itonori; Y. Ichiawa; and R. L. Schnaar; "Conversion of cellular sialic acid expression from N-acetyl- to N-glycolylneuraminic acid using a synthetic precursor, N-glycolylmannosamine pentaacetate: inhibition of myelin-associated glycoprotein binding to neural cells" Glycobiology; 2000, vol. 10, No. 1, pp. 11-20.

Conze, T. et al. (2010) "MUC2 mucin is a major carrier of the cancer-associated sialyl-Tn antigen in intestinal metaplasia and gastric carcinomas," Glycobiology 20(2), 199-206.

de León, J. et al. (2008) "Differential influence of the tumour-specific non-human sialic acid containing GM3 ganglioside on CD4+CD25? effector and naturally occuring CD4+CD25+ regulatory T cells function," International Immunology 20(4), 591-600.

de Visser, K E. et al. (2005) De novo carcinogenesis promoted by chronic inflammation is B lymphocyte dependent. Cancer Cell 7(5), 411-423.

Drake, P. M. et al. (2010) "Sweetening the Pot: Adding Glycosylation to the Biomarker Discovery Equation," Clinical Chemistry 56(2), 223-236.

Du, J. et al. (2009) "Metabolic glycoengineering: Sialic acid and beyond," Glycobiology 19(12), 1382-1401.

Eckhardt, A. E. et al. (1997) ""The Complete cDNA Sequence and Structural Polymorphism of the Polypeptide Chain of Porcine Submaxillary Mucin,"" Journal of Biological Chemistry 272(52), 33204-33210.

Ferris, R. L. et al. (2010) "Tumor Antigen—Targeted, Monoclonal Antibody—Based Immunotherapy: Clinical Response, Cellular Immunity, and Immunoescape," Journal of Clinical Oncology 28(28), 4390-4399.

Furukawa, K. et al., Analysis of the expression of N-glycolylneuraminic acid-containing gangliosides in cells and tissues using two human monoclonal antibodies. J Biol. Chem. vol. 263, 1988, pp. 18507-18512.

Goodman, M. The genomic record of Humankind's evolutionary roots. Am. J. Hum. Genet. vol. 64, 1999, pp. 31-39.

Gupta, D. and Lis, C. (2009) "Role of CA125 in predicting ovarian cancer survival-a review of the epidemiological literature," Journal of Ovarian Research 2(1), 13.

Hara, S. et al. (1986) "Highly sensitive determination of N-acetyl- and N- glycolylneuraminic acids in human serum and urine and rat serum by reversed-phase liquid chromatography with fluorescence detection," Journal of chromatography A 377, 111-119.

Hayakawa, T. et al. (2001) "Alu-mediated inactivation of the human CMP- N-acetylneuraminic acid hydroxylase gene,"Proceedings of the National Academy of Science 98(20), 11399-11404.

Hedlund, M. et al. (2007) "N-Glycolylneuraminic Acid Deficiency in Mice: Implications for Human Biology and Evolution," Molecular and Cellular Biology 27(12), 4340-4346.

Hirabayashi Y et al: "A new method for purification of anti-glycosphingolipid antibody. Avian anti-hematoside (NeuGc) antibody" Journal of Biochemistry, Japanese Biochemical Society / OUP, Tokyo; JP, vol. 94, No. 1, Jul. 1, 1983, pp. 327-330.

Hong and Stanley, "Lec3 Chinese Hamster Ovary Mutants Lack UDP-N-Acetylglucosamine 2-Epimerase Activity Because of Mutations in the Epimerase Domain of the Gne Gene." J Biol Chem, 278(52):53045-53054 (2003).

Hossler et al, Glycobiology, vol. 19, No. 9, pp. 936-949, 2009, Optimal and consistent protein glycosylation in mammalian cell culture.

Inoue, S. et al., (2010) "Extensive enrichment ofN-glycolylneuraminic acid in extracellular sialoglycoproteins abundantly synthesized and secreted by human cancer cells," Glycobiology 20(6), 752-762.

Irie, A. et al: "The Molecular Basis for the Absence of N-Glycolylneuraminic Acid in Humans", Journal of Biological Chemistry, vol. 273, No. 25, Jun. 19, 1998, pp. 15866-15871.

(56) References Cited

OTHER PUBLICATIONS

Johansen, E. et al. (2009) "A Lectin HPLC Method to Enrich Selectively-glycosylated Peptides from Complex Biological Samples," Journal of Visualized Experiments(32), 1398.

Jolles, S. et al. (2005) "Clinical uses of intravenous immunoglobulin," Clinical & Experimental Immunology 142(1), 1-11.

Ju, T. and Cummings, R. D. (2002) A unique molecular chaperone Cosme required for activity of the mammalian core 1 S3-galactosyltransferase, Proceedings of the National Academy of Sciences 99(26), 16613-16618.

Karim, M., et al. 2006 CAB Reviews: Perspectives in Agriculture, Veterinary Science, Nutrition, and Natural Resources 1 (018 ): 1-11.

Kawai T. et al., Quantitative determination of N-glycolylneuraminic acid expression in human cancerous tissues and avian lymphoma cell lines as a tumor-associated sialic acid by gas chromatography-mass spectrometry. Cancer Res. vol. 51, 1991, pp. 1242-1246.

Kawano, T. et al. (1995) "Molecular Cloning of Cytidine Monophospho-N-Acetylneuraminic Acid Hydroxylase. Regulation of Species- and Tissue-Specific Expression of N-Glycolylneuraminic Acid," Journal of Biological Chemistry 270(27), 16458-16463.

Kayser, H. et al., Biosynthesis of a nonphysiological sialic acid in different rat organs, using N-propanoyl-D-hexosamines as precursors. J Biol. Chem. vol. 267, 1992, pp. 16934-16938.

Kjeldsen, T. et al. (1988) "Preparation and Characterization of Monoclonal Antibodies Directed to the Tumor-associated O-linked Sialosyl-2?6 ?-N-Acetylgalactosaminyl (Sialosyl-Tn) Epitope," Cancer Research 48(8), 2214-2220.

Klein, A. et al., New sialic acids from biological sources identified by a comprehensive and sensitive approach: liquid chromatography-electrospray ionization-mass spectrometry (LC-ESI-MS) of SIA quinoxalinones. Glycobiology vol. 7, 1997, pp. 421-432.

Kobata, A. and Amano, J. (2005) "Altered glycosylation of proteins produced by malignant cells, and application for the diagnosis and immunotherapyof tumours," Immunology & Cell Biology 83(4), 429-439.

Kozutsumi,Y.; Kawano, T.;Yamakawa, T.; Suzuki, A J Biochem. vol. 108, 1990, pp. 704-706.

Li, C. et al. (2009) "Pancreatic Cancer Serum Detection Using a Lectin/Glyco-Antibody Array Method," Journal of Proteome Research 8(2), 483-492.

Liu, C.C. et al. (2009) "Integrative disease classification based on cross-platform microarray data," BMC Bioinformatics 10 Suppl 1:S25.

Lofling, J. C. et al. (2009) "A dietary non-human sialic acid may facilitate hemolytic-uremic syndrome," Kidney International 76(2), 140-144.

Marquina, Gilda; H. Waki; L. E. Fernandez; K. Kon; A Carr; 0. Valiente; R. Perez; and S. Ando; "Gangliosides Expressed in Human Breast Cancer"; Cancer Research; Nov. 15, 1996; 56; pp. 5165-5171.

Martin et al. Abstract #4182, Blood, (Nov. 16, 2004) vol 104, No. 11, Part 2, pp. 132B. Meeting Info.: 46th Annual Meeting of the American-Society-of-Hematology. San Diego, CA, USA. Dec. 4-7, 2004.

Martin. L. T. et al. (2002) Genetically Altered Mice with Different Sialyl transferase Deficiencies Show Tissue-specific Alterations in Sialylation and Sialic Acid 9-O-Acetylation, Journal of Biological Chemistry 277(36), 32930-32938.

Muchmore, Elaine et al, American Journal of Physical Anthropology 107:187-198 (1998); A Structural Difference Between the Cell Surfaces of Humans and the Great Apes.

Muchmore, E. et al., Biosynthesis of N-glycolyneuraminic acid. The primary site of hydroxylation of N-acetylneuraminic acid is the cytosolic sugar nucleotide pool. J Biol. Chem vol. 264, 1989, pp. 20216-20223.

Naito, Y. et al., 2007. Germinal center marker GL7 probes activation-dependent repression of N-glycolylneuraminic acid, a sialic acid species involved in the negative modulation of B-cell activation. Mol Cell Biol. Apr. 2007;27 (8):3008-22.

Nelson, H. D. et al (2009) Screening for Breast Cancer: An Update for the U.S. Preventive Services Task Force, Annals of Internal Medicine 151(10), 727-737.

Nogueira, L. et al. (2009) Prostatic specific antigen for prostate cancer detection. International Braz j urol 35(5), 521-529.

Nohle, U. et al. (1982) "Uptake, Metabolism and Excretion of Orally and Intravenously Administered, Double-Labeled N-Glycoloylneuraminic Acid and Single-Labeled 2-Deoxy-2,3-dehydro-N-acetylneuraminic Acid in Mouse and Rat," European Journal of Biochemistry 126(3), 543-548.

Oetke, Cornelia; S. Hinderlich; R. Brossmer; W. Reutter; M. Pawlita; and 0. T. Keppler; "Evidence for efficient uptake and incorporation of sialic acid by eukaryotic cells"; Eur. J. Biochem.; 2001; 265; pp. 4553-4561.

Ostrand-Rosenberg, S. (2008) "Immune surveillance: a balance between protumor and antitumor immunity," Current Opinion in Genetics & Development 18(1), 11-18.

Oyelaran O; McShane LM; Dodd L; Gildersleeve JC: 'Profiling human serum antibodies with a carbohydrate antigen microarray' J Proteome Res. vol. 8, 2009, pp. 4301-4310.

Pearce, O. M. et al. (2010) "Chemo-enzymatic synthesis of the carbohydrate antigen N-glycolylneuraminic acid from glucose," Carbohydrate Research 345(9), 1225-1229.

Phelps, C. J. et al., "Production of Alpha 1,3-Galactosyltransferase-Deficient Pigs." Science, 299(5605):411-414 (2003).

Saldova, R. et al., 'Glycosylation changes on serum glycoproteins in ovarian cancer may contribute to disease pathogenesis' Dis Markers vol. 25, 2008, pp. 219-232.

Sato et al. Frequent occurrence of pre-existing alpha 2→8-linked disialic and oligosialic acids with chain lengths up to 7 Sia residues in mammalian brain glycoproteins. Prevalence revealed by highly sensitive chemical methods and anti-di-, oligo-, and poly-Sia antibodies specific for defined chain lengths. J. Bioi. Chem. 2000 vol. 276, p. 15422-15431.

Sato, Chihiro et al., "Carbohydrates, Lipids, and Other Natural Products: Identification of Oligo-N-Glycolylneuraminic Acid Residues in Mammal-derived Glycoproteins by a Newly Developed Immunochemical Reagent and Biochemical Methods", J. Biol. Chem. 1998, 273:2575-2582.

Schröder, F. H. et al. (2009) "Screening and Prostate-Cancer Mortality in a Randomized European Study," New England Journal of Medicine 360(13), 1320-1328.

Schwarzkopf, et al., "Sialylation is Essential for Early Development in Mice." Proc Natl Acad Sci U S A, 99(8):5267-5270 (2002).

Sewell R. et al. (2006) The ST6GaINAc-l Sialyltransferase Localizes throughout the Golgi and Is Responsible for the Synthesis of the Tumor-associated Sialyl-Tn O-Glycan in Human Breast Cancer, Journal of Biological Chemistry 281(6), 3586-3594.

Shaw, L. et al. (1994) "CMP-N-acetylneuraminic acid hydroxylase from mouse liver and pig submandibular glands," European Journal of Biochemistry 219(3), 1001-1011.

Sjoberg, Eric R.; L. D. Powell; A Klein; and A Varki; "Natural Ligands of the B Cell Adhesion Molecule CD22j3 can be Masked by 9-0-Acetylation of Sialic Acids"; The Journal of Cell Biology; Jul. 1994L Voo. 126, No. 2., pp. 549-562.

Slovin, S. F. et al. (2005) "Carbohydrate vaccines as immunotherapy for cancer," Immunology & Cell Biology 83(4), 418-428.

Sonnenburg, Justin L.; H. van Halbeek; and A Varki "Characterization of the Acid Stability of Glycosidically Linked Neuraminic Acid"; The Journal of Biological Chemistry; May 17, 2002; vol. 277, No. 20, pp. 17502-17510.

Soussi, T. (2000) "p53 Antibodies in the Sera of Patients with Various Types of Cancer: A Review," Cancer Research 60(7), 1777-1788.

Srivastava, S. and Gopal-Srivastava, R. (2002) "Biomarkers in Cancer Screening: A Public Health Perspective," The Journal of Nutrition 132(8), 2471S-2475S.

Stanley and loffe, "Glycosyltransferase Mutants: Key to New Insights in Glycobiology." FASEB J, 9(14):1436-1444 (1995).

Takematsu, H. et al., (1994) "Reaction Mechanism Underlying CMP-N-Acetylneuraminic Acid Hydroxylation in Mouse Liver: Formation of a Ternary Complex of Cytochrome b5, CMP-N-Acetylneuraminic Acid, and a Hydroxylation Enzyme," J. Biochem. (Tokyo) 115(3), 381-386.

(56) References Cited

OTHER PUBLICATIONS

Taylor, R. E. et al. (2010) "Novel mechanism for the generation of human xeno-autoantibodies against the nonhuman sialic acid N-glycolylneuraminic acid," The Journal of Experimental Medicine 207(8), 1637-1646.
Thompson I.M. et al. (2005) "Operating characteristics of prostate-specific antigen in men with an initial psa level of 3.0 ng/ml or lower," JAMA: The Journal of the American Medical Association 294(1), 66-70.
Uygur-Bayramicli, O. et al. (2007) "Type 2 diabetes mellitus and CA 19-9 levels," World Journal of Gastroenterology 13(40), 5357-5359.
Vamecq, J.et al., Subcellular distribution of glycolyltransferases in rodent liver and their significance in special reference to the synthesis of N-glycolyneuraminic acid. J Biochem vol. 111, 1992, pp. 579-583.
Varki "Sialic Acids in Human Health and Disease." Trends Mol Med, 14(8):351-360 (2008).
Varki, A "N-glycolylneuraminic acid deficiency in humans", Biochimie 83 (2001) 615-622.
Varki, A. "Loss of N-Glycolylneuraminic Acid in Humans: Mechanisms, Consequences, and Implications for Hominid Evolution" Yearbook of Physical Anthropology 44:54-69 (2001).
Varki, A. (2010) "Uniquely human evolution of sialic acid genetics and biology," Proceedings of the National Academy of Sciences 107(Supplement 2), 8939-8946.
Varki, A. et al. (2009) Glycosylation Changes in Cancer, in Essentials of Glycobiology. Ch 44, pp. 617-632, Cold Spring Harbor Laboratory Press, Cold Spring Harbor, New York.
Varki, A. et al. (2009) in Essentials of Glycobiology (Varki, A., et al., Eds.), Ch. 14, pp. 199-218, Cold Spring Harbor Laboratory Press, Cold Spring Harbor, NY.
Varki, Ajit; "Sialic acids such as ligands in recognition phenomena" The FASEB Journal; Mar. 1997; vol. 111 pp. 248-255.
Wang, B. et al. (2001) "Concentration and distribution of sialic acid in human milk and infant formulas," American Journal of Clinical Nutrition 74(4), 510-515.
Wang, B. et al. (2007) "Dietary sialic acid supplementation improves learning and memory in piglets," American Journal of Clinical Nutrition 85(2), 561-569.
Weiss, J. M. et at. (2007) Immunotherapy of Cancer by IL-12-based Cytokine Combinations. Expert Opinion on Biological Therapy 7(11), 1705-1721.
Wong, N.S. et al, 2010. An Investigation of Intracellular Glycosylation Activities in CHO Cells: Effects of Nucleotide Sugar Precursor Feeding. Biotechnology and Bioengineering. 107(2):321-36.
Wright, et al., "Piscine Islet Xenotransplantation." ILAR J, 45(3):314-323 (2004).
Wu, X. et al. (2004) "A New Homobifunctional p-Nitro Phenyl Ester Coupling Reagent for the Preparation of Neoglycoproteins," Organic Letters 6(24), 4407-4410.
Wu. C.-Y. et al. (2009) New development of glycan arrays, Organic & Biomolecular Chemistry 7(11), 2247-2254.
Yu, H. et al. (2005) A Multifunctional Pasteurella multocida Sialyltransferase: A Powerful Powerful Tool for the Synthesis of Sialoside Libraries, Journal of the American Chemical Society 127(50), 17618-17619.
Yu, H. et al. (2006) Highly Efficient Chemoenzymatic Synthesis of Naturally Occurring and Non-Natural a-2,6-Linked Sialosides: A P. damsela a-2,6-Sialyltransferase with Extremely Flexible Donor-Substrate Specificity, Angewandte Chemie International Edition 45(24), 3938-3944.
Yu, H. et al. (2006) One-pot three-enzyme chemoenzymatic approach to the synthesis of sialosides containing natural and non-natural functionalities. Nature Protocols 1(5), 2485-2492.
Yu, H. et al. (2007) "Efficient chemoenzymatic synthesis of biotinylated human serum albumin-sialoglycoside conjugates containing O-acetylated sialic acids," Organic & Biomolecular Chemistry 5(15), 2458-2463.
Zhang, D.Y. et al. (2009) "Proteomics, pathway array and signaling network-based medicine in cancer," Cell Division 4 (1), 20.
Angata, T. et al. (2002) "Chemical Diversity in the Sialic Acids and Related α-Keto Acids: An Evolutionary Perspective," Chemical Reviews 102(2), 439-470.
Asaoka, H. et al. "Two chicken monoclonal antibodies specific for heterophil Hanganutziu-Deicher antigens." Immunol. Lett vol. 32, 1992, pp. 91-96.
Candefjord, S. et al. (2009) "Technologies for localization and diagnosis of prostate cancer," Journal of Medical Engineering & Technology 33(8), 585-603.
Carr, et al. "A Mouse IgG1 Monoclonal Antibody Specific for N-Glycolyl Gm3 Ganglioside Recognized Breast and Melanoma Tumors." Hybridoma, 19(3):241-247 (2000).
Cavadas, V. et al. (2010) "Prostate Cancer Prevention Trial and European Randomized Study of Screening for Prostate Cancer Risk Calculators: A Performance Comparison in a Contemporary Screened Cohort," European Urology 58(4), 551-558.
Chenu, et al. "Reduction of Cmp-N-Acetylneuraminic Acid Hydroxylase Activity in Engineered Chinese Hamster Ovary Cells Using an Antisense-RNA Strategy." Biochim Biophys Acta, 1622(2):133-144 (2003).
Dai, et al., "Targeted Disruption of the Alpha1,3-Galactosyltransferase Gene in Cloned Pigs." Nat Biotechnol, 20 (3):251-255 (2002).

\* cited by examiner

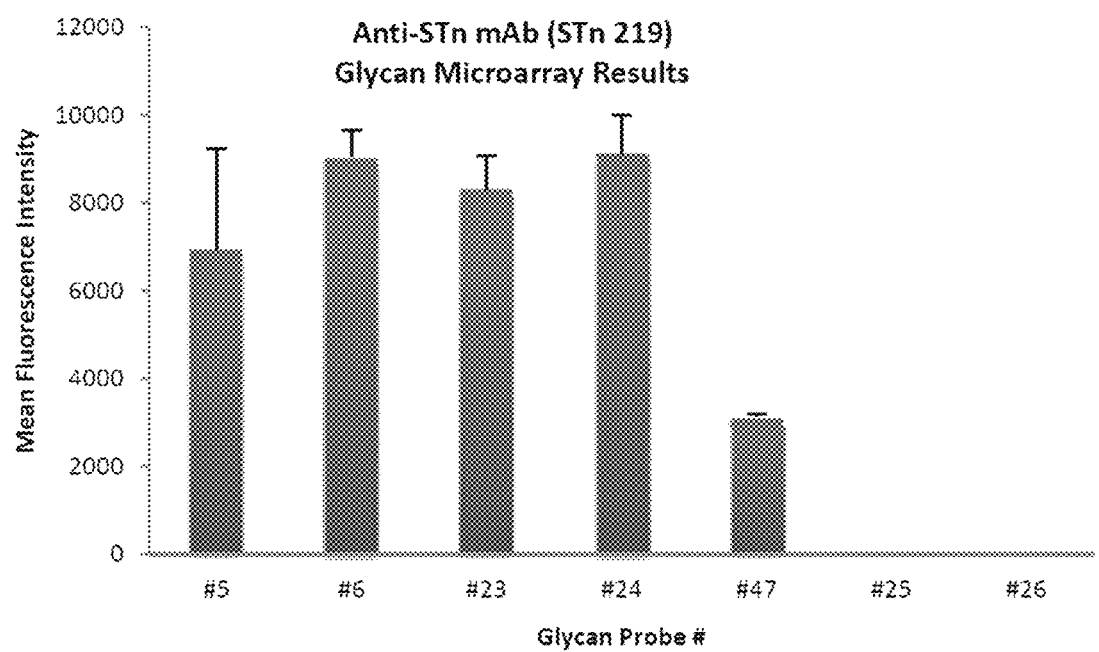

SEQUENCE LISTING

<160> NUMBER OF SEQ ID NOS: 6

<210> SEQ ID NO 1
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide <400> SEQUENCE: 1

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ala Leu Ile
    50                  55                  60

Ser Arg Leu Ser Ile Ser Lys Asp Asn Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Lys Gly Gly Tyr Phe Asp Tyr Trp Gly Gln Gly Thr Thr Leu Thr Val
            100                 105                 110

Ser Ser

<210> SEQ ID NO 2
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

```
Gln Ile Val Leu Thr Gln Ser Pro Ala Val Met Ser Ala Ser Pro Gly
1               5                   10                  15

Glu Lys Val Ala Ile Thr Cys Ser Ala Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Trp Thr
                85                  90                  95

Phe Gly Gly Gly Thr Lys Leu Glu Ile Lys
            100                 105
```

<210> SEQ ID NO 3
<211> LENGTH: 342
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

```
caggtgcagc tgaaggagtc aggacctggc ctggtggcgc cctcacagag cctgtccatc      60
acatgcactg tctcagggtt ctcattaacc agctatggtg taagctgggt tcgccagcct     120
ccaggaaagg gtctggagtg gctgggagta atatgggggtg acgggagcac aaattatcat     180
tcagctctca tatccagact gagcatcagc aaggataact ccaagagcca gttttctta      240 aaactgaaca gtctgcaaac tgatgacaca gccacgtact actgtgccaa agggggctac     300
tttgactact ggggccaagg caccactctc acagtctcct ca                        342
```

<210> SEQ ID NO 4
<211> LENGTH: 319
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4

```
caaattgttc tcacccagtc tccagcagtc atgtctgcat ctccagggga gaaggtcgcc      60
ataacctgca gtgccagctc aagtgtaagt tacatgcact ggttccagca gaagccaggc     120
acttctccca aactctggat ttatagcaca tccaacctgg cttctggagt ccctgctcgc     180
ttcagtggca gtggatctgg gacctcttac tctctcacaa tcagccgaat ggaggctgaa     240
gatgctgcca cttattactg ccagcaaagg agtagttacc cgtggacgtt cggtggaggc     300
accaagctgg aaatcaaac                                                  319
```

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic peptide

```
<400> SEQUENCE: 5

Glu Gln Lys Leu Ile Ser Glu Glu Asp Leu
1               5                   10

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asp Tyr Lys Asp Asp Asp Asp Lys
1               5
```

GLYCAN-INTERACTING COMPOUNDS

CROSS REFERENCE TO RELATED APPLICATIONS

This application is a Continuation in Part of PCT Application Number PCT/US2013/029240, filed Mar. 6, 2013, entitled Glycan-Interacting Compounds, which claims priority to U.S. Provisional Patent Application No. 61/620,414, filed Apr. 4, 2012, entitled Anti-GcSTn Monoclonal Antibodies and Methods for Treating Cancer, the content of each of which is herein incorporated by reference in its entirety.

REFERENCE TO THE SEQUENCE LISTING

The instant application contains a Sequence Listing which has been submitted electronically in ASCII format and is hereby incorporated by reference in its entirety. Said ASCII copu, created on Nov. 22,2013, is named 20331066USCIP_SL.txt and is 4,289 bytes in size.

FIELD OF THE INVENTION

This invention relates to compounds and compositions, including, but not limited to antibodies for the detection and/or removal of glycosylated matter from an organism.

BACKGROUND OF THE INVENTION

Aberrant glycosylation accompanies some of the other mutations commonly observed in carcinomas. It has been estimated that about 80% of all carcinomas express a truncated glycan, the Tn Antigen. With few exceptions Tn and the sialylated form Sialyl Tn (STn), are not expressed in normal, healthy tissues. Furthermore, the non-human immunogenic sialic acid, N-glycolylneuraminic acid (Neu5Gc), seems to be differentially expressed on carcinomas such as breast cancer in the form of Neu5Gc-STn (GcSTn).

Multiple aberrant glycosylation forms have been described in human cancers, identifying specific glycans as a class of cell surface molecules suitable for specific tumor targeting (Cheever, M. A. et al., The prioritization of cancer antigens: a national cancer institute pilot project for the acceleration of translational research. Clin Cancer Res. 2009 Sep. 1; 15(17): 5323-37). For example, various human cancer types (such as bladder, breast, cervical, colon, lung, and ovarian cancer among others) show high expression of STn antigen, which is rare in normal human tissues (Karlen, P. et al., Sialyl-Tn antigen as a marker of colon cancer risk in ulcerative colitis: relation to dysplasia and DNA aneuploidy. Gastroenterology. 1998 December; 115(6):1395-404; Ohno, S. et al, Expression of Tn and sialyl-Tn antigens in endometrial cancer: its relationship with tumor-produced cyclooxygenase-2, tumor-infiltrated lymphocytes and patient prognosis. Anticancer Res. 2006 November-December; 26(6A):4047-53). In addition, the presence of STn on tumor-associated mucins relates to cancer with poor prognosis and is therewith considered an attractive epitope for cancer detection and targeted therapy (Cao, Y. et al., Immunodetection of epithelial mucin (MUC1, MUC3) and mucin-associated glycotopes (TF, Tn, and sialosyl-Tn) in benign and malignant lesions of colonic epithelium: apolar localization corresponds to malignant transformation. Virchows Arch. 1997 September; 431(3):159-66; Julien, S. et al., Sialyl-Tn vaccine induces antibody-mediated tumour protection in a relevant murine model. Br J. Cancer. 2009 Jun. 2; 100(11):1746-54; Itzkowitz, S. H. et al., Sialosyl-Tn. A novel mucin antigen associated with prognosis in colorectal cancer patients. Cancer. 1990 Nov. 1; 66(9):1960-6; Motoo, Y. et al., Serum sialyl-Tn antigen levels in patients with digestive cancers. Oncology. 1991; 48(4):321-6; Kobayashi, H. et al., Serum sialyl Tn as an independent predictor of poor prognosis in patients with epithelial ovarian cancer. J Clin Oncol. 1992 January; 10(1):95-101). Tn and STn formation is associated with somatic mutations in the gene Cosmc that encodes a molecular chaperon required for the formation of the activate T-synthase (Ju, T. et al., Protein glycosylation: chaperone mutation in Tn syndrome. Nature. 2005 Oct. 27; 437(7063):1252; Ju, T. et al., Human tumor antigens Tn and sialyl Tn arise from mutations in Cosmc. Cancer Res. 2008 Mar. 15; 68(6):1636-46). It can also result from increased expression of the sialyl transferase, ST6GalNAc-I (Ikehara, Y. et al., Cloning and expression of a human gene encoding an N-acetylgalactosamine-alpha-2,6-sialyltransferase (ST6GalNAc I): a candidate for synthesis of cancer-associated sialyl-Tn antigens. Glycobiology. 1999 November; 9(11):1213-24; Brockhausen, I. et al., Pathways of mucin O-glycosylation in normal and malignant rat colonic epithelial cells reveal a mechanism for cancer-associated Sialyl-Tn antigen expression. Biol. Chem. 2001 February; 382(2):219-32). De-novo expression of STn can modulate carcinoma cells, change the malignant phenotype, and lead to more aggressive cell behaviors (Pinho, S. et al., Biological significance of cancer-associated sialyl-Tn antigen: modulation of malignant phenotype in gastric carcinoma cells. Cancer Lett. 2007 May 8; 249(2):157-70). Although STn is highly expressed in malignant tissues, low levels are also found on healthy human cells (Jass, J. R. et al., Distribution of sialosyl Tn and Tn antigens within normal and malignant colorectal epithelium. J. Pathol. 1995 June; 176(2):143-9; Kirkeby, S. et al., MUC1 and the simple mucin-type antigens: Tn and Sialyl-Tn are differently expressed in salivary gland acini and ducts from the submandibular gland, the vestibular folds, and the soft palate. Arch Oral Biol. 2010 November; 55(11):830-41). STn alone has attracted attention as a target for cancer detection and therapy (Cheever, M. A. et al., The prioritization of cancer antigens: a national cancer institute pilot project for the acceleration of translational research. Clin Cancer Res. 2009 Sep. 1; 15(17):5323-37).

In addition to the presence of STn, other glycosylation changes have been described in cancer. One of them involves Neu5Gc. N-acetylneuraminic acid (Neu5Ac) and Neu5Gc are the two major sialic acids on mammalian cell surfaces. Neu5Ac and Neu5Gc differ only in that Neu5Gc comprises an additional oxygen atom associated with chemical group attached to carbon 5. Due to the loss of a functional gene, humans can only synthesize sialic acid in the form of Neu5Ac, but not Neu5Gc. However Neu5Gc can be metabolically incorporated into humans from animal-derived dietary sources such as red meats (Tangvoranuntakul, P. et al., Human uptake and incorporation of an immunogenic nonhuman dietary sialic acid. Proc Natl Acad Sci USA. 2003 Oct. 14; 100(21):12045-50; Nguyen, D. H. et al., Effects of natural human antibodies against a nonhuman sialic acid that metabolically incorporates into activated and malignant immune cells. J. Immunol. 2005 Jul. 1; 175(1):228-36; U.S. Pat. Nos. 7,682,794, 8,084,219, US2012/0142903, WO2010030666 and WO2010030666, herein incorporated by reference in their entirety). Neu5Gc is significantly abundant among human tumors (Higashi, H. et al., Characterization of N-glycolylneuraminic acid-containing gangliosides as tumor-associated Hanganutziu-Deicher antigen in human colon cancer. Cancer Res. 1985 August; 45(8):3796-802; Miyoshi I. et al., Detection of 4-O-acetyl-N-glycolylneuraminyl lactosylceramide as one of tumor-associated antigens in human colon cancer tissues by specific antibody. Mol. Immunol. 1986. 23: 631-638; Hirabayashi, Y. et al., Occurrence of tumor-associated ganglioside antigens with Hanganutziu-Deicher antigenic activity on human melanomas. Jpn J Cancer Res. 1987. 78: 614-620; Kawachi. S, et al., Heterophile Hanganutziu-Deicher antigen in ganglioside fractions of human melanoma tissues. Int Arch Allergy Appl Immunol. 1988. 85: 381-383; Devine, P. L. et al., The breast tumor-associated epitope defined by monoclonal antibody 3E1.2 is an O-linked mucin carbohydrate containing N-glycolylneuraminic acid. Cancer Res. 1991. 51: 5826-5836; Malykh, Y. N. et al, N-Glycolylneuraminic acid in human tumours. Biochimie. 2001. 83: 623-634) and remarkably low in normal human tissues, which had been overlooked for several decades (Diaz, S. L. et al., Sensitive and specific detection of the non-human sialic Acid N-glycolylneuraminic acid in human tissues and biotherapeutic products. PLoS One. 2009. 4: e4241; Tangvoranuntakul, P. et al., Human uptake and incorporation of an immunogenic nonhuman dietary sialic acid. Proc Natl Acad Sci USA. 2003. 100: 12045-12050; Varki, A. et al., Multiple changes in sialic acid biology during human evolution. Glycoconj J. 2009. 26: 231-245.) The increased metabolic accumulation of diet-derived Neu5Gc in cancer tissue compared to healthy human tissues is likely explained by at least three factors: rapid growth with underproduction of competing endogenous Neu5Ac, enhanced macropinocytosis induced by growth factors (Dharmawardhane, S. et al., Regulation of macropinocytosis by p21-activated kinase-1. Mol Biol Cell. 2000 October; 11(10):3341-52; Simonsen, A. et al., The role of phosphoinositides in membrane transport. Curr Opin Cell Biol. 2001 August; 13(4):485-92; Johannes, L. et al., Clathrin-dependent or not: is it still the question? Traffic. 2002 July; 3(7):443-51; Amyere, M. et al., Origin, originality, functions, subversions and molecular signaling of macropinocytosis. Int J Med. Microbiol. 2002 February; 291(6-7): 487-94), and the upregulation of gene expression of the lysosomal sialic acid transporter gene sialin by hypoxia (Yin, J. et al., Hypoxic culture induces expression of sialin, a sialic acid transporter, and cancer-associated gangliosides containing non-human sialic acid on human cancer cells. Cancer Res. 2006 Mar. 15; 66(6):2937-45). In addition, all humans tested to date comprise a polyclonal antibody reservoir against non-human Neu5Gc, which makes it the first example of a xeno-autoantigen (Padler-Karavani, V. et al., Diversity in specificity, abundance, and composition of anti-Neu5Gc antibodies in normal humans: potential implications for disease. Glycobiology. 2008 October; 18(10):818-30; Varki, N. M. et al., Biomedical differences between human and nonhuman hominids: potential roles for uniquely human aspects of sialic acid biology. Annu Rev Pathol. 2011; 6:365-93). The accumulation of dietary Neu5Gc in malignant tumors in the face of an anti-Neu5Gc response was shown to facilitate tumor progression by inducing a low-grade chronic inflammation (Hedlund, M. et al., Evidence for a human-specific mechanism for diet and antibody-mediated inflammation in carcinoma progression. Proc Natl Acad Sci USA. 2008 Dec. 2; 105(48):18936-41). Thus, Neu5Gc containing glycan epitopes on human tumors represent a valuable possibility for drug targeting. A recent study suggests the existence of antibodies against Neu5Gc-containing STn (GcSTn), but not Neu5Ac-STn (AcSTn), in cancer patients and explores their potential as a specific biomarker for cancer detection (Padler-Karavani, V. et al., Human xeno-autoantibodies against non-human sialic acid serve as novel serum biomarkers and immunotherapeutics in cancer. Cancer Res. 2011 May 1; 71(9):3352-63).

However, the available antibodies have major drawbacks as they likely do not detect GcSTn and react only AcSTn by definition. There remains a need for antibodies specific for GcSTn. There are important methodological reasons for this gap. First, Neu5Gc is widely present in non-human mammals, and hence mammalian cell lines, which are conventionally utilized for antibody production. Under normal conditions it is difficult to gain immunity against a "self" molecule. Second, the myeloma cells commonly used as fusion partners to establish a hybridoma endogenously produce and expresses Neu5Gc. The endogenous production and expression may cause the binding of this antigen to antibody produced from the same cells. This situation would likely result in poor antibody yield and/or reduced survival of the hybridoma cells. Third, in most cases, the antibody producing cells are cultured in media that contain animal products (such as fetal calf serum), which also prevents the production of antibodies specific against Neu5Gc containing epitopes creating yet another barrier to the production of GcSTn.

SUMMARY OF THE INVENTION

The present invention provides an isolated antibody directed toward one or more cancer-related antigens, wherein one or more are selected from the group consisting of mucin-related antigens, blood group Lewis-related antigens, glycosphingolipid-related antigens, ganglioside-related antigens and polysialic acid-related antigens. In some embodiments, the mucin-related antigens are selected from the group consisting of N-acetylgalactosamine (Tn), sialyl (alpha2,6)N-acetylgalactosamine (STn) and galactose(beta1, 3)N-acetylgalactosamine (Thomsen-Friedenreich antigen or TF). In some embodiments, the blood group Lewis-related antigens are selected from the group consisting of Lewis$^Y$, Lewis$^X$, Sialyl Lewis$^X$ and Sialyl Lewis$^A$. In some embodiments, the glycosphingolipid related antigens are selected from the group consisting of Globo H and stage-specific embryonic antigen-3. In some embodiments, the ganglioside-related antigens are selected from the group consisting of GD2, GD3, GM2, fucosyl GM1 and GM3. In some embodiments, the cancer-related antigens are linked to a sialic acid residue. In some embodiments, the sialic acid residue may be N-acetylneuraminic acid (Neu5Ac) or N-glycolylneuraminic acid (Neu5Gc). In some embodiments the cancer-related antigen is Neu5Gc(alpha2,6)N-acetylgalactosamine (GcSTn). In some embodiments, the isolated antibody is monoclonal. In some embodiments, the isolated antibody is developed according to a method comprising the use of a glycan array.

The present invention contemplates an antibody directed toward one or more glycans comprising the structure S1-S2-S3-S4-S5 wherein S1 is absent or is a residue selected from the group consisting of Neu5Ac and Neu5Gc, S2 is absent or a residue selected from the group consisting of galactose (Gal), 2-keto-3-deoxy-D-glycero-D-galacto-nononic acid (KDN), Neu5Ac and Neu5Gc, S3 is absent or a residue selected from the group consisting of KDN, Neu5Gc, Gal, N-acetylglucosamine (GlcNAc) and Neu5Ac, S4 is absent or a residue selected from the group consisting of Gal, Neu5Ac and Neu5Gc and S5 is a residue selected from the group consisting of Gal, N-acetylgalactosamine (GalNAc), glucose (Glc), GlcNAc and 6-Sulfo-N-acetylglucosamine (GlcNAc6S). In some embodiments, the one or more glycans comprise a parent chain comprising at least one branch chain. In some embodiments, at least one branch chain comprises a fucose (Fuc) branching residue. In some embodiments, the fucose branching residue is linked to S5 by an alpha1,3 linkage. In some embodiments, the branch chain comprises one or more branching residues selected from the group consisting of Neu5Ac, Neu5Gc and KDN linked to S4. In some embodiments, at least one Neu5Gc branching residue is linked to S4 by an alpha 2,3 linkage. In some embodiments, the glycans comprise a terminal residue selected from the group consisting of Neu5Ac and Neu5Gc. In some embodiments, the terminal residue is methylated at carbon 2. In some embodiments, the terminal residue is linked by a glycosidic bond selected from the group consisting of an alpha2,3 glycosidic bond and an alpha2,6 glycosidic bond to a residue selected from the group consisting of Gal and GalNAc. In some embodiments, the terminal residue comprises an acetyl group attached to carbon 9. In some embodiments, the glycans comprise an entity (R) coupled to S5 by a linkage selected from the group consisting of an alpha linkage and a beta linkage. In some embodiments, R comprises one or more entities selected from the group consisting of a serine residue, a threonine residue, a protein, a lipid, a glycan and a carbohydrate linker. In some embodiments, R comprises a carbohydrate linker comprising $O(CH_2)_2CH_2NH_2$.

The present invention also provides an antibody directed toward one or more glycans, wherein said one or more glycans comprise one or more polysaccharide chains selected from the group consisting of Neu5Gc(alpha2,3)Gal(beta1,4)GlcNAc, 9-acetyl-Neu5Gc(alpha2,6)GalNAc, Neu5Gc(alpha2,3)Gal, Neu5Gc(alpha2,6)Gal, 9-acetyl-Neu5Gc(alpha2,6)Gal, Neu5Gc(alpha2,3)Gal(beta1,4)[Fuc(alpha1,3)]GlcNAc and Neu5Gc(alpha2,3)Gal(beta1,4)GlcNAc. In some embodiments, the GlcNAc residues are sulfated on carbon 6. In some embodiments, the glycans comprise a linkage to an entity (R), wherein said linkage is selected from the group consisting of an alpha linkage and a beta linkage and wherein R comprises one or more entities selected from the group consisting of a serine residue, a threonine residue, a protein, a lipid, a glycan and a carbohydrate linker.

In some embodiments, any of the antibodies of the present invention may interacts with one or more regions of antibody recognition selected from the group consisting of a sialic acid residue, a bond between a sialic acid residue and an adjacent residue on the glycan chain, a region of interaction between a sialic acid residue and an adjacent glycan, and a region of interaction between a sialic acid residue and a residue on a branching chain of the same glycan.

The present invention also provides a method of producing one or more glycan-interacting antibodies comprising the steps of contacting one or more mammals with a composition comprising one or more glycans, detecting the presence of said one or more glycan-interacting antibodies in one or more serum samples derived from said one or more mammals using one or more modes of detection selected from the group consisting of enzyme-linked immunosorbent assays and glycan arrays, selecting at least one mammal wherein said one or more glycan-interacting antibodies have been detected and isolating spleen cells from said at least one mammal and using them to produce said one or more glycan-interacting antibodies using a technology selected from the group consisting of hybridoma formation and phage display technology. In some embodiments, the composition comprising one or more glycans comprises one or more forms of synthetic STn selected from the group consisting of Neu5Gc-STn and Neu5Ac-STn. In some embodiments, the composition comprising one or more glycans comprises submaxillary mucin. In some embodiments, the submaxillary mucin is porcine submaxillary mucin (PSM). In some embodiments, the mammals are mice. In some embodiments, the mice are selected from the group consisting of transgenic mice and knockout mice. In some embodiments, the knockout mice do not express a functional version of the enzyme cytidine monophosphate-N-acetylneuraminic acid hydroxylase (CMAH). In some embodiments, the hybridoma formation comprises the fusion of said spleen cells with cells from a myeloma cell line to generate hybridoma cells. In some embodiments, the isolated colonies of said hybridoma cells are selected for antibody generation based on the detection of said one or more glycan-interacting antibodies in the medium used to culture said isolated colonies. In some embodiments, detection comprises using one or more modes of detection selected from the group consisting of enzyme-linked immunosorbent assays and glycan arrays. In some embodiments, the glycan-interacting antibodies are directed toward a cancer-related antigen. In some embodiments, the cancer-related antigen comprises sialic acid. In some embodiments, the sialic acid is Neu5Gc. The present invention also provides an isolated antibody prepared according to any of the embodiments of this method.

In some embodiments, antibodies of the present invention are whole IgG antibodies. In some embodiments, these are humanized.

The present invention also provides compositions comprising any of the antibodies described herein, further comprising an excipient. The present invention also provides a kit comprising this composition along with instructions for use thereof.

BRIEF DESCRIPTION OF THE FIGURES

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead being placed upon illustrating the principles of various embodiments of the invention.

FIG. 1. Anti-STn mAb (STn 219) was purchased from Abcam. An antibody dilution of 1:250 was allowed to hybridize with the blocked glycan array slide. After a one-hour incubation at RT, the slide was washed, and hybridized with a Cy3-conjugated secondary anti-mouse antibody. Glycan Probe #5 is Neu5Ac-α-2-6-GalNAc (AcSTn), Glycan Probe #6 is Neu5Gc-α-2-6-GalNAc (GcSTn), Glycan Probe #23 is Neu5,9Ac2-α-2,6-GalNAc, Glycan Probe #24 is Neu9Ac5Gc-α-2,6-GalNAc, Glycan Probe #47 is GalNAc, Glycan Probe #25 is Neu5Ac-α-2,3-Gal and Glycan Probe #26 is Neu5Gc-α-2,3-Gal.

DETAILED DESCRIPTION

Introduction

Provided herein is a monoclonal anti-GcSTn as a biotherapeutic. Also provided herein are methods for generating such an antibody by immunizing a mouse that has had the Cmah gene disrupted to produce a human-like mutation in which it can no longer produce Neu5Gc, the immunogenic, non-human form of sialic acid. Also provided is a Cmah$^{-/-}$ myeloma cell for producing a hybridoma that is free of Neu5Gc expression, for production of a GcSTn monoclonal antibody either by reducing the amount of recoverable anti-GcSTn or the hybridoma will begin to die due to antibody binding back to the hybridoma.

In some embodiments, the present invention provides glycan-interacting antibodies (Glycan-interacting antibodies) designed to bind glycans present on a variety of molecular targets. In some embodiments, glycan-interacting antibodies bind molecular targets comprising epitopes further comprising Neu5Gc. In some embodiments, glycan-interacting antibodies comprise antibodies against Neu5Gc that stimulate the immune system to clear molecular targets comprising Neu5Gc. Further provided are methods for producing and optimizing glycan-interacting antibodies as well as kits and assays for exploiting such glycan-interacting antibodies.

Definitions

Adjacent: As used herein, the term "adjacent" refers to something that is adjoining, neighboring or next to a given entity. In some embodiments, "adjacent residues" are sugar residues within a glycan chain that are linked to one another. In some embodiments, "adjacent glycans" are glycan chains that next to each other either in direct contact or within close proximity and without another glycan in between the two.

Administered in combination: As used herein, the term "administered in combination" or "combined administration" means that a subject is simultaneously exposed to two or more agents administered at the same time or within an interval such that the subject is at some point in time simultaneously exposed to both and/or such that there may be an overlap in the effect of each agent on the patient. In some embodiments, at least one dose of one or more agents is administered within about 24 hours, 12 hours, 6 hours, 3 hours, 1 hour, 30 minutes, 15 minutes, 10 minutes, 5 minutes, or 1 minute of at least one dose of one or more other agents. In some embodiments, administration occurs in overlapping dosage regimens. As used herein, the term "dosage regimen" refers to a plurality of doses spaced apart in time. Such doses may occur at regular intervals or may include one or more hiatus in administration. In some embodiments, the administration of individual doses of one or more glycan-interacting antibodies, as described herein, are spaced sufficiently closely together such that a combinatorial (e.g., a synergistic) effect is achieved.

Amino acid: As used herein, the terms "amino acid" and "amino acids" refer to all naturally occurring L-alpha-amino acids as well as non-naturally occurring amino acids. Amino acids are identified by either the one-letter or three-letter designations as follows: aspartic acid (Asp:D), isoleucine (Ile:I), threonine (Thr:T), leucine (Leu:L), serine (Ser:S), tyrosine (Tyr:Y), glutamic acid (Glu:E), phenylalanine (Phe:F), proline (Pro:P), histidine (His:H), glycine (Gly:G), lysine (Lys:K), alanine (Ala:A), arginine (Arg:R), cysteine (Cys:C), tryptophan (Trp:W), valine (Val:V), glutamine (Gln:Q) methionine (Met:M), asparagine (Asn:N), where the amino acid is listed first followed parenthetically by the three and one letter codes, respectively.

Animal: As used herein, the term "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone.

Antibody: As used herein, the term "antibody" is used in the broadest sense and specifically covers various embodiments including, but not limited to monoclonal antibodies, polyclonal antibodies, multispecific antibodies (e.g. bispecific antibodies formed from at least two intact antibodies), and antibody fragments such as diabodies so long as they exhibit a desired biological activity. Antibodies are primarily amino-acid based molecules but may also comprise one or more modifications such as with sugar moieties.

Antibody fragment: As used herein, the term "antibody fragment" refers to a portion of an intact antibody, preferably comprising an antigen binding region thereof. Examples of antibody fragments include Fab, Fab', F(ab')$_2$, and Fv fragments; diabodies; linear antibodies; single-chain antibody molecules; and multispecific antibodies formed from antibody fragments. Papain digestion of antibodies produces two identical antigen-binding fragments, called "Fab" fragments, each with a single antigen-binding site. Also produced is a residual "Fc" fragment, whose name reflects its ability to crystallize readily. Pepsin treatment yields an F(ab')$_2$ fragment that has two antigen-binding sites and is still capable of cross-linking antigen. glycan-interacting antibodies may comprise one or more of these fragments. For the purposes herein, an antibody may comprise a heavy and light variable domain as well as an Fc region.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: As used herein, the terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. An "association" need not be strictly through direct covalent chemical bonding. It may also suggest ionic or hydrogen bonding or a hybridization based connectivity sufficiently stable such that the "associated" entities remain physically associated.

Bifunctional: As used herein, the term "bifunctional" refers to any substance, molecule or moiety which is capable of or maintains at least two functions. The functions may affect the same outcome or a different outcome. The structure that produces the function may be the same or different.

Biomolecule: As used herein, the term "biomolecule" is any natural molecule which is amino acid-based, nucleic acid-based, carbohydrate-based or lipid-based, and the like.

Branch: As used herein, the term "branch" refers to an entity, moiety or appendage that is linked or extends out from a main entity or source. In some embodiments, a "branch chain" or "branching chain" comprises one or more residues (including, but not limted to sugar residues) that extend from a parent chain. As used herein, a "parent chain" is used to refer to a chain of residues (including, but not limited to sugar residues) from which a branching chain is linked. In the case of a glycan with multiple branches, the parent chain may also refer to the source chain from which all such branches are directly or indirectly attached. In the case of a polysaccharide comprising a chain of hexose residues, parent chain linkages typically occur between carbons 1 and 4 of adjacent residues while branching chains are attached to a parent chain through a linkage between carbon 1 of the branching residue and carbon 3 of the parent residue from which the branch extends. As used herein, the term "branching residue" refers to the residue attached to the parent chain in a branching chain.

Compound: As used herein, the term "compound," refers to a distinct chemical entity. In some embodiments, a particular compound may exist in one or more isomeric or isotopic forms (including, but not limited to stereoisomers, geometric isomers and isotopes). In some embodiments, a compound is provided or utilized in only a single such form. In some embodiments, a compound is provided or utilized as a mixture of two or more such forms (including, but not limited to a racemic mixture of stereoisomers). Those of skill in the art appreciate that some compounds exist in different such forms, show different properties and/or activities (including, but not limited to biological activities). In such cases it is within the ordinary skill of those in the art to select or avoid particular forms of the compound for use in accordance with the present invention. For example, compounds that contain asymmetrically substituted carbon atoms can be isolated in optically active or racemic forms. Methods on how to prepare optically active forms from optically active starting materials are known in the art, such as by resolution of racemic mixtures or by stereoselective synthesis.

Cyclic or Cyclized: As used herein, the term "cyclic" refers to the presence of a continuous loop. Cyclic molecules need not be circular, only joined to form an unbroken chain of subunits.

Cytidine monophosphate-N-acetylneuraminic acid hydroxylase: As used herein, the term "cytidine monophosphate-N-acetylneuraminic acid hydroxylase" or "CMAH" refers to an enzyme, absent in humans, but present in most other mammals (including, but not limited to mice, pigs and chimpanzees) that catalyzes the formation of N-glycolylneuraminic acid from N-acetylneuraminic acid. The absence of the enzyme in humans is due to a frameshift mutation resulting in the premature termination of the CMAH transcript and the production of a non-functional protein.

Cytotoxic: As used herein, the term "cytotoxic" is used to refer to an agent that kills or causes injurious, toxic, or deadly effects on a cell (e.g., a mammalian cell (e.g., a human cell)), bacterium, virus, fungus, protozoan, parasite, prion, or a combination thereof.

Delivery: As used herein, "delivery" refers to the act or manner of delivering a compound, substance, entity, moiety, cargo or payload.

Delivery Agent: As used herein, "delivery agent" refers to any substance which facilitates, at least in part, the in vivo delivery of an agent Detectable label: As used herein, "detectable label" refers to one or more markers, signals, or moieties which are attached, incorporated or associated with another entity, which markers, signals or moieties are readily detected by methods known in the art including radiography, fluorescence, chemiluminescence, enzymatic activity, absorbance and the like. Detectable labels include radioisotopes, fluorophores, chromophores, enzymes, dyes, metal ions, ligands such as biotin, avidin, streptavidin and haptens, quantum dots, and the like. Detectable labels may be located at any position in the entity with which they are attached, incorporated or associated. For example, when attached, incorporated in or associated with a peptide or protein, they may be within the amino acids, the peptides, or proteins, or located at the N- or C-termini.

Display library: As used herein, the term "display library" refers to a tool used in scientific discovery to identify biomolecular interactions. Different variations of display libraries exist that include the utilization of bacteriophages, yeast and ribosomes. In each case, proteins within a given library (also referred to herein as "library members") are linked (physically or through association with a host) to the nucleic acid which encodes the protein. When a target molecule is incubated with the members of a display library, any library members that bind to the target may be isolated and the sequences encoding the bound protein may be determined through analysis of the linked nucleic acid. In some embodiments, display libraries are "phage display libraries" wherein the display library is made up of bacteriophage viral particles (also referred to herein as "phage particles") wherein nucleic acids have been incorporated into the phage genome resulting in the production of viral coat proteins that are fused to proteins encoded by the nucleic acids that have been introduced. Such fused proteins are "displayed" on the outer surface of the assembled phage particles where they may interact with a given target.

Distal: As used herein, the term "distal" means situated away from the center or away from a point or region of interest.

Engineered: As used herein, embodiments of the invention are "engineered" when they are designed to have a feature or property, whether structural or chemical, that varies from a starting point, wild type or native molecule. Thus, engineered agents or entities are those whose design and/or production include an act of the hand of man.

Epitope: As used herein, an "epitope" refers to a surface or region on a molecule that is capable of interacting with components of the immune system, including, but not limited to antibodies. In some embodiments, an epitope may comprise a target site.

Ether bond: As used herein, an "ether bond" refers to a chemical bond comprising an oxygen bonded between two carbon atoms. In some embodiments, ether bonds link sugar residues to other entities, including, but not limited to other sugar residues to form a glycan chain. Such bonds are also referred to as "glycosidic bonds" or "glycosidic linkages". In the context of at least one sugar residue, the terms "link" and/or "linkage" are also used herein when referring to a glycosidic linkage. In some embodiments, linkages may link glycans to other entities, including, but not limited to proteins, lipids, phospholipids and sphingolipids. In some embodiments, sugar residues may be linked to protein, typically forming a link between a sugar residue and an amino acid residue. Such amino acid residues include serine and threonine. In some embodiments, ether bonds link glycans to a glycan array comprising a carbohydrate linker that participates in bond formation. Glycosidic linkages may differ in their stereochemical properties. In some embodiments, alpha oriented glycosidic linkages (also referred to herein as "alpha linkages") result in an axial orientation between the bonded oxygen of the ether bond and the cyclohexane ring of the sugar reside. In some embodiments, beta oriented glycosidic linkages (also referred to herein as "beta linkages") result in an equatorial orientation between the bonded oxygen of the ether bond and the cyclohexane ring of the sugar residue.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; (4) folding of a polypeptide or protein; and (5) post-translational modification of a polypeptide or protein.

Feature: As used herein, a "feature" refers to a characteristic, a property, or a distinctive element.

Formulation: As used herein, a "formulation" includes at least one antibody and a delivery agent.

Functional: As used herein, a "functional" biological molecule is a biological entity with a structure and in a form in which it exhibits a property and/or activity by which it is characterized. As used herein, a "functional group" or "chemical group" refers to a characteristic group of atoms or chemical bonds that are part of a larger molecule. In some embodiments, functional groups may be associated with different molecules, but may participate in similar chemical reactions regardless of the molecule of which they are a part. Common functional groups include, but are not limited to carboxyl groups (—COOH), acetyl groups (—COH), amino groups (—NH$_2$), methyl groups (—CH$_3$), sulfate groups (—SO$_3$H) and acyl groups. In some embodiments, the addition of one or more functional group to a molecule may be conveyed using terms that modify the name of the functional group with the ending "-ylated", e.g., acetylated, methylated and sulfated.

Glycan: As used herein, the terms "glycan", "oligosaccharide" and "polysaccharide" are used interchangeably and refer to polymers made up of sugar monomers, typically joined by glycosidic bonds also referred to herein as linkages. In some embodiments, the terms "glycan", "oligosaccharide" and "polysaccharide" may be used to refer to the carbohydrate portion of a glycoconjugate (e.g., glycoprotein, glycolipid or proteoglycan).

Glycan chain: As used herein, the term "glycan chain" refers to a sugar polymer comprising two or more sugars. In some embodiments, glycan chains are covalently linked to proteins through serine or threonine residues on the protein.

Glycan-rich composition: As used herein, the term "glycan-rich composition" refers to composition comprising a large percentage of glycans. In some embodiments, glycans within a glycan-rich composition may comprise from about 1% to about 10%, from about 5% to about 15%, from about 20% to about 40%, from about 30% to about 50%, from about 60% to about 80%, from about 70% to about 90% or at least 100% of the total weight of the composition.

Glycosidic bond: As used herein, the term "glycosidic bond" refers to a covalent bond formed between a carbohydrate and another chemical group. In some embodiments, glycosidic bonds are formed between the reducing end of one sugar molecule and the non-reducing end of a second sugar molecule or polysaccharide chain. Such glycosidic bonds are also known as O-glycosidic bonds due to the oxygen (or ether bond) between the joined sugars. In some embodiments, a glycosidic bond between two sugars or between a sugar and a linker may also be referred to as a "linkage".

In vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In vivo: As used herein, the term "in vivo" refers to events that occur within an organism (e.g., animal, plant, or microbe or cell or tissue thereof).

Isolated: As used herein, the term "isolated" is synonymous with "separated", but carries with it the inference separation was carried out by the hand of man. In one embodiment, an isolated substance or entity is one that has been separated from at least some of the components with which it was previously associated (whether in nature or in an experimental setting). Isolated substances may have varying levels of purity in reference to the substances from which they have been associated. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

Kit: As used herein, the term "kit" refers to a set comprising multiple components adapted for a cooperative purpose and instructions for use thereof.

Knockout: As used herein, the term "knockout" refers to an organism wherein an existing gene has been inactivated through a process that typically involves the hand of man. In a knockout organism, a gene that has been inactivated is said to have been "knocked out". In some embodiments, the knocked out gene may be inactivated through the insertion of a nucleotide sequence into the gene or through replacement of the gene entirely.

Linker: As used herein, a "linker" refers to a moiety that connects two or more domains, moieties or entities. In one embodiment, a linker may comprise 10, 11, 12, 13, 14, 15 or more atoms. In a further embodiment, a linker may comprise a group of atoms, e.g., 10-1,000 atoms, and can be comprised of the atoms or groups such as, but not limited to, carbon, amino, alkylamino, oxygen, sulfur, sulfoxide, sulfonyl, carbonyl, and imine. In some embodiments, the linker may comprise an amino acid, peptide, polypeptide or protein. In some embodiments, a moiety bound by a linker may include, but is not limited to an atom, a chemical group, a nucleoside, a nucleotide, a nucleobase, a sugar, a nucleic acid, an amino acid, a peptide, a polypeptide, a protein, a protein complex, a payload (e.g., a therapeutic agent) or a marker (including, but not limited to a chemical, fluorescent, radioactive or bioluminescent marker). The linker can be used for any useful purpose, such as to form multimers or conjugates, as well as to administer a payload, as described herein. Examples of chemical groups that can be incorporated into the linker include, but are not limited to, alkyl, alkenyl, alkynyl, amido, amino, ether, thioether, ester, alkylene, heteroalkylene, aryl, or heterocyclyl, each of which can be optionally substituted, as described herein. Examples of linkers include, but are not limited to, unsaturated alkanes, polyethylene glycols (e.g., ethylene or propylene glycol monomeric units, e.g., diethylene glycol, dipropylene glycol, triethylene glycol, tripropylene glycol, tetraethylene glycol, or tetraethylene glycol), and dextran polymers, Other examples include, but are not limited to, cleavable moieties within the linker, such as, for example, a disulfide bond (—S—S—) or an azo bond (—N═N—), which can be cleaved using a reducing agent or photolysis. Non-limiting examples of a selectively cleavable bonds include an amido bond which may be cleaved for example by the use of tris(2-carboxyethyl)phosphine (TCEP), or other reducing agents, and/or photolysis, as well as an ester bond which may be cleaved for example by acidic or basic hydrolysis. In some embodiments, a linker is a carbohydrate moiety used to link glycans to a substrate, such as in a glycan array. Such carbohydrate linkers include, but are not limited to —O(CH$_2$)$_2$CH$_2$HN$_2$ and —O(CH$_2$)$_3$NHCOCH$_2$(OCH$_2$CH$_2$)$_6$NH$_2$.

mRNA: As used herein, the term "mRNA" refers to messenger RNA produced as a result of gene transcription and processing of the generated transcript. In some embodiments, mRNA that has left the nucleus of the cell may be extracted from a cell or set of cells and analyzed to determine which genes have undergone transcription at a given time or under a given set of circumstances.

Mucin: As used herein, the term "mucin" refers to a family of proteins that are heavily glycosylated. In some embodiments mucins are produced by the submaxillary glands and are found in saliva and mucous.

Negative selection: As used herein, the term "negative selection" refers to the selection of library members from a display library based on their ability to bind entities and/or components of a composition that do not comprise a target antigen. In some embodiments, negative selection is used prior to positive selection to remove elements that might bind non-specifically to the target.

Off-target: As used herein, "off target" refers to any unintended effect on any one or more target, gene, or cellular transcript.

Patient: As used herein, "patient" refers to a subject who may seek or be in need of treatment, requires treatment, is receiving treatment, will receive treatment, or a subject who is under care by a trained (e.g., licensed) professional for a particular disease or condition.

Peptide: As used herein, "peptide" is less than or equal to 50 amino acids long, e.g., about 5, 10, 15, 20, 25, 30, 35, 40, 45, or 50 amino acids long.

Pharmaceutically acceptable: The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipients: The phrase "pharmaceutically acceptable excipient," as used herein, refers any ingredient other than active agents (e.g., as described herein) present in a pharmaceutical composition and having the properties of being substantially nontoxic and non-inflammatory in a patient. In some embodiments, a pharmaceutically acceptable excipient is a vehicle capable of suspending or dissolving the active agent. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

Pharmaceutically acceptable salts: Pharmaceutically acceptable salts of the compounds described herein are forms of the disclosed compounds wherein the acid or base moiety is in its salt form (e.g., as generated by reacting a free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Pharmaceutically acceptable salts include the conventional non-toxic salts, for example, from non-toxic inorganic or organic acids. In some embodiments a pharmaceutically acceptable salt is prepared from a parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17$^{th}$ ed., Mack Publishing Company, Easton, Pa., 1985, p. 1418, *Pharmaceutical Salts: Properties, Selection, and Use*, P. H. Stahl and C. G. Wermuth (eds.), Wiley-VCH, 2008, and Berge et al., *Journal of Pharmaceutical Science*, 66, 1-19 (1977), each of which is incorporated herein by reference in its entirety. Pharmaceutically acceptable solvate: The term "pharmaceutically acceptable solvate," as used herein, refers to a crystalline form of a compound wherein molecules of a suitable solvent are incorporated in the crystal lattice. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate." In some embodiments, the solvent incorporated into a solvate is of a type or at a level that is physiologically tolerable to an organism to which the solvate is administered (e.g., in a unit dosage form of a pharmaceutical composition).

Pharmacokinetic: As used herein, "pharmacokinetic" refers to any one or more properties of a molecule or compound as it relates to the determination of the fate of substances administered to a living organism. Pharmacokinetics is divided into several areas including the extent and rate of absorption, distribution, metabolism and excretion. This is commonly referred to as ADME where: (A) Absorption is the process of a substance entering the blood circulation; (D) Distribution is the dispersion or dissemination of substances throughout the fluids and tissues of the body; (M) Metabolism (or Biotransformation) is the irreversible transformation of parent compounds into daughter metabolites; and (E) Excretion (or Elimination) refers to the elimination of the substances from the body. In rare cases, some drugs irreversibly accumulate in body tissue.

Physicochemical: As used herein, "physicochemical" means of or relating to a physical and/or chemical property.

Positive selection: As used herein, the term "positive selection" refers to the selection of library members from a display library based on their ability to bind the desired target. In some embodiments, positive selection is used with phage display libraries to identify phage particles expressing scFvs that bind to the desired target. In some embodiments, the desired target is one or more glycans comprising Neu5Gc.

Preventing: As used herein, the term "preventing" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

Prodrug: The present disclosure also includes prodrugs of the compounds described herein. As used herein, "prodrugs" refer to any substance, molecule or entity which is in a form predicate for that substance, molecule or entity to act as a therapeutic upon chemical or physical alteration. Prodrugs may by covalently bonded or sequestered in some way and which release or are converted into the active drug moiety prior to, upon or after administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Preparation and use of prodrugs is discussed in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference in their entirety.

Proximal: As used herein, the term "proximal" means situated nearer to the center or to a point or region of interest.

Region of interaction: As used herein, the term "region of interaction" refers to a region along any of two or more entities where such entities interact or overlap. In some embodiments, a region of interaction may comprise one or more sugar residues along a glycan chain that contacts a second glycan chain. In some embodiments, the glycan chains are branching chains from the same parent chain. In some embodiments, a region of interaction may occur between two glycan chains wherein one chain is a branching chain and the second chain is a parent chain. In the case of glycan chains, regions of interaction may comprise 1, 2, 3, 4, 5, 6, 7, 8, 9 or at least 10 sugar residues. In some embodiments, regions of interaction may also occur between glycans and proteins or between glycans and lipids.

Region of antibody recognition: As used herein, the term "region of antibody recognition" refers to the region on an antigen or between two or more antigens that is specifically recognized and bound by a corresponding antibody. In some embodiments a region of antibody recognition comprises one or more sugar residues along one or more glycan. In some embodiments, a region of antibody recognition may comprise 1, 2, 3, 4, 5, 6, 7, 8, 9 or at least 10 sugar residues. In some embodiments, a region of antibody recognition may comprise a region of interaction. In some embodiments, a region of antibody recognition may comprise a junction between two sugar residues, between a branching chain and a parent chain or between a glycan and a protein.

Residue: As used herein, the term "residue" refers to a monomer associated with or capable of associating with a polymer. In some embodiments, residues comprise sugar molecules including, but not limited to glucose, galactose, N-acetylglucosamine, N-acetylgalactosamine, sialic acids. In some embodiments, residues comprise amino acids.

Sample: As used herein, the term "sample" refers to an aliquot or portion taken from a source and/or provided for analysis or processing. In some embodiments, a sample is from a biological source such as a tissue, cell or component part (e.g. a body fluid, including but not limited to blood, mucus, lymphatic fluid, synovial fluid, cerebrospinal fluid, saliva, amniotic fluid, amniotic cord blood, urine, vaginal fluid and semen). In some embodiments, a sample may be or comprise a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. In some embodiments, a sample is a or comprises a medium, such as a nutrient broth or gel, which may contain cellular components, such as proteins or nucleic acid molecule. In some embodiments, a "primary" sample is an aliquot of the source. In some embodiments, a primary sample is subjected to one or more processing (e.g., separation, purification, etc.) steps to prepare a sample for analysis or other use.

Selection: As used herein, the term "selection" refers to the isolation or identification of a given entity based on a given criteria or property. In some embodiments, selection comprises the isolation of phage particles from a phage display library based on their ability to bind an antigen.

Sialyl: As used herein, the prefix "sialyl" as well as the term "sialylated" describe compounds comprising sialic acid.

Single-chain variable fragment: As used herein, the term "single-chain variable fragment" or "scFv" refers to a fusion protein comprising antibody variable regions connected by a linker. In some embodiments, scFvs are utilized in conjunction with phage display methods where they may be expressed in association with a phage coat protein and used in the identification of high affinity peptides for a given antigen.

Single unit dose: As used herein, a "single unit dose" is a dose of any therapeutic administered in one dose/at one time/single route/single point of contact, i.e., single administration event. In some embodiments, a single unit dose is provided as a discrete dosage form (e.g., a tablet, capsule, patch, loaded syringe, vial, etc).

Split dose: As used herein, a "split dose" is the division of single unit dose or total daily dose into two or more doses.

Stable: As used herein "stable" refers to a compound or entity that is sufficiently robust to survive isolation to a useful degree of purity from a reaction mixture, and preferably capable of formulation into an efficacious therapeutic agent.

Stabilized: As used herein, the term "stabilize", "stabilized," "stabilized region" means to make or become stable. In some embodiments, stability is measured relative to an absolute value. In some embodiments, stability is measured relative to a reference compound or entity.

Subject: As used herein, the term "subject" or "patient" refers to any organism to which a composition in accordance with the invention may be administered, e.g., for experimental, diagnostic, prophylactic, and/or therapeutic purposes. Typical subjects include animals (e.g., mammals such as mice, rats, rabbits, non-human primates, and humans) and/or plants.

Submaxillary glands: As used herein, the term "submaxillary glands" or "submandibular glands" refers to mucous producing glands located beneath the mouth floor. These glands are capable of producing mucins and in some embodiments, may be extracted from mammals as a source of mucin.

Suffering from: An individual who is "suffering from" a disease, disorder, and/or condition has been diagnosed with or displays one or more symptoms of a disease, disorder, and/or condition.

Susceptible to: An individual who is "susceptible to" a disease, disorder, and/or condition has not been diagnosed with and/or may not exhibit symptoms of the disease, disorder, and/or condition but harbors a propensity to develop a disease or its symptoms. In some embodiments, an individual who is susceptible to a disease, disorder, and/or condition (for example, cancer) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Synthetic: The term "synthetic" means produced, prepared, and/or manufactured by the hand of man. Synthesis of polynucleotides or polypeptides or other molecules of the present invention may be chemical or enzymatic.

Target: As used herein, the term "target" refers to an object or entity to be affected by an action. In some embodiments, targets refer to antigens to be used for the development of antibodies that specifically bind the antigens.

Target site: As used herein, the term "target site" refers to a target on or within one or more glycans, biomolecules and/or biostructures within a cell, the extracellular space, a tissue, an organ and/or an organism. In some embodiments, glycan target sites may reside exclusively on one sugar residue or may be formed by two or more residues. In some embodiments, target sites are formed between two or more glycans. In some embodiments, target sites are formed between branching chains of the same glycan or between one or more branching chains and a parent chain.

Targeted Cells: As used herein, "targeted cells" refers to any one or more cells of interest. The cells may be found in vitro, in vivo, in situ or in the tissue or organ of an organism. The organism may be an animal, preferably a mammal, more preferably a human and most preferably a patient.

Terminal residue: As used herein, the term "terminal residue" refers to the last residue in a polymeric chain. In some embodiments, terminal residues are sugar residues located at the non-reducing end of a polysaccharide chain.

Therapeutic agent: The term "therapeutic agent" refers to any agent that, when administered to a subject, has a therapeutic, diagnostic, and/or prophylactic effect and/or elicits a desired biological and/or pharmacological effect.

Therapeutically effective amount: As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition. In some embodiments, a therapeutically effective amount is provided in a single dose. In some embodiments, a therapeutically effective amount is administered in a dosage regimen comprising a plurality of doses. Those skilled in the art will appreciate that in some embodiments, a unit dosage form may be considered to comprise a therapeutically effective amount of a particular agent or entity if it comprises an amount that is effective when administered as part of such a dosage regimen.

Therapeutically effective outcome: As used herein, the term "therapeutically effective outcome" means an outcome that is sufficient in a subject suffering from or susceptible to an infection, disease, disorder, and/or condition, to treat, improve symptoms of, diagnose, prevent, and/or delay the onset of the infection, disease, disorder, and/or condition.

Total daily dose: As used herein, a "total daily dose" is an amount given or prescribed in 24 hr period. It may be administered as a single unit dose.

Transgenic: As used herein, the term "transgenic" refers to an organism that comprises one or more genes incorporated within the organisms genome that are not naturally found in that organism.

Treating: As used herein, the term "treating" refers to partially or completely alleviating, ameliorating, improving, relieving, delaying onset of, inhibiting progression of, reducing severity of, and/or reducing incidence of one or more symptoms or features of a particular infection, disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Variable region: As used herein, the term "variable region" or "variable domain" refers to specific antibody domains that differ extensively in sequence among antibodies and are used in the binding and specificity of each particular antibody for its particular antigen.

Whole IgG: As used herein, the term "whole IgG" refers to a complete IgG molecule. In some embodiments, whole IgG molecules comprise regions found naturally in two or more other organisms.

Wild type: As used herein, the term "wild type" refers to an organism comprising a natural genome (free from genes derived from other organisms).

I. Compositions of the Invention

In some embodiments, the present invention provides compounds as well as compositions that comprise at least one glycan-interacting antibody. As used herein, the term "glycan" refers to a polysaccharide comprising a polymeric chain of two or more monosaccharides. Within a glycan, monosaccharide monomers may all be the same or they may differ. Common monomers include, but are not limited to trioses, tetroses, pentoses, glucose, fructose, galactose, xylose, arabinose, lyxose, allose, altrose, mannose, gulose, iodose, ribose, mannoheptulose, sedoheptulose and talose. Amino sugars may also be monomers within a glycan. Glycans comprising such sugars are herein referred to as aminoglycans. Amino sugars, as used herein, are sugar molecules that comprise an amine group in place of a hydroxyl group, or in some embodiments, a sugar derived from such a sugar. Examples of amino sugars include, but are not limited to glucosamine, galactosamine, N-acetylglucosamine, N-acetylgalactosamine, sialic acids (including, but not limited to, N-acetylneuraminic acid and N-glycolylneuraminic acid) and L-daunosamine.

As used herein the term "glycan-interacting antibody" refers to an exogenously supplied compound, composition or entity comprising one or more antibody or fragments thereof which functions to bind to, alter, activate, inhibit, stabilize, degrade and/or modulate a glycan or a glycan-associated molecule or entity. In some embodiments, glycan-interacting antibodies may comprise conjugates or combinations with other molecules. In some embodiments, glycan-interacting antibodies are directed toward glycans comprising one or more amino sugar. In a further embodiment, one or more amino sugar is a sialic acid. In a further embodiment, one or more sialic acid is N-acetylneuraminic acid and/or N-glycolylneuraminic acid.

Antibodies

Glycan-interacting antibodies may comprise antibodies or fragments thereof. As used herein, the term "antibody" is used in the broadest sense and specifically covers various embodiments including, but not limited to monoclonal antibodies, polyclonal antibodies, multispecific antibodies (e.g. bispecific antibodies formed from at least two intact antibodies), and antibody fragments such as diabodies so long as they exhibit a desired biological activity. Antibodies are primarily amino-acid based molecules but may also comprise one or more modifications such as with sugar moieties.

"Antibody fragments" comprise a portion of an intact antibody, preferably comprising an antigen binding region thereof. Examples of antibody fragments include Fab, Fab', F(ab')$_2$, and Fv fragments; diabodies; linear antibodies; single-chain antibody molecules; and multispecific antibodies formed from antibody fragments. Papain digestion of antibodies produces two identical antigen-binding fragments, called "Fab" fragments, each with a single antigen-binding site. Also produced is a residual "Fc" fragment, whose name reflects its ability to crystallize readily. Pepsin treatment yields an F(ab')$_2$ fragment that has two antigen-binding sites and is still capable of cross-linking antigen. Glycan-interacting antibodies may comprise one or more of these fragments. For the purposes herein, an "antibody" may comprise a heavy and light variable domain as well as an Fc region.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain.

As used herein, the term "variable domain" refers to specific antibody domains that differ extensively in sequence among antibodies and are used in the binding and specificity of each particular antibody for its particular antigen. As used herein, the term "Fv" refers to antibody fragments which contain a complete antigen-recognition and antigen-binding site. This region consists of a dimer of one heavy chain and one light chain variable domain in tight, non-covalent association.

Antibody "light chains" from any vertebrate species can be assigned to one of two clearly distinct types, called kappa and lambda based on amino acid sequences of their constant domains. Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2a, IgG2b, IgG2c, IgG3, IgG4, IgA, and IgA2. "Single-chain Fv" or "scFv" as used herein, refers to a fusion protein of $V_H$ and $V_L$ antibody domains, wherein these domains are linked together into a single polypeptide chain. In some embodiments, the Fv polypeptide linker enables the scFv to form the desired structure for antigen binding.

The term "diabodies" refers to small antibody fragments with two antigen-binding sites, which fragments comprise a heavy chain variable domain $V_H$ connected to a light chain variable domain $V_L$ in the same polypeptide chain. By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993), the contents of each of which are incorporated herein by reference in their entirety.

The term "monoclonal antibody" as used herein refers to an antibody obtained from a population of substantially homogeneous cells (or clones), i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen The modifier "monoclonal" indicates the character of the antibody as being obtained from a substantially homogeneous population of antibodies, and is not to be construed as requiring production of the antibody by any particular method. The monoclonal antibodies herein include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies.

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from the hypervariable region from an antibody of the recipient are replaced by residues from the hypervariable region from an antibody of a non-human species (donor antibody) such as mouse, rat, rabbit or nonhuman primate having the desired specificity, affinity, and capacity.

The term "hypervariable region" when used herein in reference to antibodies refers to regions within the antigen binding domain of an antibody comprising the amino acid residues that are responsible for antigen binding. The amino acids present within the hypervariable regions determine the structure of the complementarity determining region (CDR). As used herein, the "CDR" refers to the region of an antibody that comprises a structure that is complimentary to its target antigen or epitope.

In some embodiments, glycan-interacting antibodies of the present invention may be antibody mimetics. The term "antibody mimetic" refers to any molecule which mimics the function or effect of an antibody and which binds specifically and with high affinity to their molecular targets. In some embodiments, antibody mimetics may be monobodies, designed to incorporate the fibronectin type III domain (Fn3) as a protein scaffold (U.S. Pat. Nos. 6,673,901; 6,348,584). In some embodiments, antibody mimetics may be those known in the art including, but are not limited to affibody molecules, affilins, affitins, anticalins, avimers, DARPins, Fynomers and Kunitz and domain peptides. In other embodiments, antibody mimetics may include one or more non-peptide region.

As used herein, the term "antibody variant" refers to a biomolecule resembling an antibody in structure and/or function comprising some differences in their amino acid sequence, composition or structure as compared to a native antibody.

Antibody Development

Glycan-interacting antibodies of the present invention are developed to bind antigens described herein. As used herein, an "antigen" is an entity which induces or evokes an immune response in an organism. An immune response is characterized by the reaction of the cells, tissues and/or organs of an organism to the presence of a foreign entity. Such an immune response typically leads to the production by the organism of one or more antibodies against the foreign entity, e.g., antigen or a portion of the antigen. Antigens of the invention may comprise glycans, glycoconjugates (including, but not limited to glycoproteins and glycolipids), peptides, polypeptides, fusion proteins, or any of the foregoing and may be conjugated or complexed to one or more separate adjuvants or heterologous proteins.

As used herein, an "adjuvant" is a pharmacological or immunological agent that modifies the effect of other agents. Adjuvants according to the present invention include, but are not limited chemical compositions, biomolecules, therapeutics, and/or therapeutic regimens.

Antibodies of the present invention may be polyclonal or monoclonal or recombinant, produced by methods known in the art or as described in this application.

In some embodiments, the antibodies of the present invention may be labeled for purposes of detection with a detectable label known by one of skill in the art. The label can be a radioisotope, fluorescent compound, chemiluminescent compound, enzyme, or enzyme co-factor, or any other labels known in the art. In some aspects, the antibody that binds to a desired antigen is not labeled, but may be detected by binding of a labeled secondary antibody that specifically binds to the primary antibody.

Antibodies of the present invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), intracellularly made antibodies (i.e., intrabodies), and epitope-binding fragments of any of the above. Antibodies of the present invention can be from any animal origin including birds and mammals. Preferably, such antibodies are of human, murine (e.g., mouse and rat), donkey, sheep, rabbit, goat, guinea pig, camel, horse, or chicken origin. The antibodies of the present invention can be monospecific or multispecific (e.g., bispecific, trispecific, or of greater multispecificity). Multispecific antibodies can be specific for different epitopes of a target antigen of the present invention, or can be specific for both a target antigen of the present invention, and a heterologous epitope, such as a heterologous glycan, peptide or solid support material. (See, e.g., WO 93/17715; WO 92/08802; WO 91/00360; WO 92/05793; Tutt, A. et al., *Trispecific F(ab)3 derivatives that use cooperative signaling via the TCR/CD3 complex and CD2 to activate and redirect resting cytotoxic T cells*. J. Immunol. 1991 Jul. 1; 147(1):60-9; U.S. Pat. Nos. 4,474,893; 4,714,681; 4,925,648; 5,573,920; 5,601,819; and Kostelny, S. A. et al., *Formation of a bispecific antibody by the use of leucine zippers*. J. Immunol. 1992 Mar. 1; 148(5):1547-53).

Glycan-interacting antibodies of the present invention comprising monoclonal antibodies can be prepared using well-established methods known by those skilled in the art. In one embodiment, the monoclonal antibodies are prepared using hybridoma technology (Kohler, G. et al., *Continuous cultures of fused cells secreting antibody of predefined specificity*. Nature. 1975 Aug. 7; 256(5517):495-7). For hybridoma formations, first, a mouse, hamster, or other appropriate host animal, is typically immunized with an immunizing agent (e.g., a target antigen of the invention) to elicit lymphocytes that produce or are capable of producing antibodies that will specifically bind to the immunizing agent. Alternatively, the lymphocytes may be immunized in vitro. The lymphocytes are then fused with an immortalized cell line using a suitable fusing agent, such as polyethylene glycol, to form a hybridoma cell (Goding, J. W., *Monoclonal Antibodies: Principles and Practice*. Academic Press. 1986; 59-103 1). Immortalized cell lines are usually transformed mammalian cells, particularly myeloma cells of rodent, rabbit, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor, D. et al., *A human hybrid myeloma for production of human monoclonal antibodies*. J. Immunol. 1984 December; 133(6):3001-5; Brodeur, B. et al., Monoclonal Antibody Production Techniques and Applications. Marcel Dekker, Inc., New York. 1987; 33:51-63).

The culture medium in which the hybridoma cells are cultured can then be assayed for the presence of monoclonal antibodies. Preferably, the binding specificity (i.e., specific immunoreactivity) of monoclonal antibodies produced by the hybridoma cells is determined by immunoprecipitation or by an in vitro binding assay, such as radioimmunoassay (RIA) or enzyme-linked immunosorbent assay (ELISA). Such techniques and assays are known by those skilled in the art. The binding specificity of the monoclonal antibody can, for example, be determined by Scatchard analysis (Munson, P. J.

et al., *Ligand: a versatile computerized approach for characterization of ligand-binding systems*. Anal Biochem. 1980 Sep. 1; 107(1):220-39).

After the desired hybridoma cells are identified, the clones may be subcloned by limiting dilution procedures and grown by standard methods. Suitable culture media for this purpose include, for example, Dulbecco's Modified Eagle's Medium or RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

In another embodiment, the monoclonal antibodies of the present invention can also be made by recombinant DNA methods, such as those described in U.S. Pat. No. 4,816,567, which is hereby incorporated by reference in its entirety. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

In some embodiments, antibodies of the present invention may be produced by various procedures known by those skilled in the art. For the production of polyclonal antibodies in vivo, host animals, such as rabbits, rats, mice, cows, horses, donkeys, chickens, monkeys, sheep or goats, are immunized with either free or carrier-coupled antigens, for example, by intraperitoneal and/or intradermal injection. In some embodiments, injection material may be an emulsion containing about 100 µg of antigen or carrier protein. In some embodiments, injection materials comprise a glycan-rich composition such as non-human mammalian submaxillary mucin in solution. Various adjuvants can also be used to increase the immunological response, depending on the host species. Adjuvants include, but are not limited to, Freund's (complete and incomplete), mineral gels such as aluminum hydroxide, surface active substances such as lysolecithin, pluronic polyols, polyanions, peptides, oil emulsions, TiterMax® (CytRx Corp, Los Angeles, Calif.), keyhole limpet hemocyanins, dinitrophenol, and potentially useful human adjuvants such as BCG (bacille Calmette-Guerin) and *corynebacterium parvum*. Such adjuvants are also well known in the art. Several booster injections may be needed, for instance, at intervals of about two weeks, to provide a useful titer of antibody which can be detected, for example, by ELISA assay using glycans and/or free peptide adsorbed to a solid surface. The titer of antibodies in serum from an immunized animal can be increased by selection of antibodies, e.g., by adsorption of antigens onto a solid support and elution of the selected antibodies according to methods well known in the art.

Glycan-interacting antibodies, variants and fragments thereof may be selected and produced using high throughput methods of discovery. In one embodiment, glycan-interacting antibodies comprising synthetic antibodies, variants and fragments thereof are produced through the use of display libraries. The term "display" as used herein, refers to the expression or "display" of proteins or peptides on the surface of a given host. The term "library" as used herein, refers to a collection of unique cDNA sequences and/or the proteins that are encoded by them. A library may contain from as little as two unique cDNAs to hundreds of billions of unique cDNAs.

In a preferred embodiment, glycan-interacting antibodies comprising synthetic antibodies are produced using antibody display libraries or antibody fragment display libraries. The term "antibody fragment display library" as used herein, refers to a display library wherein each member encodes an antibody fragment containing at least one variable region of an antibody. Such antibody fragments are preferably Fab fragments, but other antibody fragments such as single-chain variable fragments (scFvs) are contemplated as well. In an Fab antibody fragment library, each Fab encoded may be identical except for the amino acid sequence contained within the variable loops of the complementarity determining regions (CDRs) of the Fab fragment. In an alternative or additional embodiment, amino acid sequences within the individual $V_H$ and/or $V_L$ regions may differ as well.

Display libraries may be expressed in a number of possible hosts including, but not limited to yeast, bacteriophage, bacteria and retroviruses. Additional display technologies that may be used include ribosome-display, microbead-display and protein-DNA linkage techniques. In a preferred embodiment, Fab display libraries are expressed in yeast or in bacteriophages (also referred to herein as "phages" or "phage particles". When expressed, the Fabs decorate the surface of the phage or yeast where they can interact with a given antigen. An antigen comprising a glycan or other antigen from a desired target may be used to select phage particles or yeast cells expressing antibody fragments with the highest affinity for that antigen. The DNA sequence encoding the CDR of the bound antibody fragment can then be determined through sequencing using the bound particle or cell. In one embodiment, positive selection is used in the development of antibodies. In some embodiments, negative selection is utilized in the development of antibodies. In some embodiments, both positive and negative selection methods are utilized during multiple rounds of selection in the development of antibodies using display libraries.

In yeast display, cDNA encoding different antibody fragments are introduced into yeast cells where they are expressed and the antibody fragments are "displayed" on the cell surface as described by Chao et al. (Chao, G. et al., *Isolating and engineering human antibodies using yeast surface display*. Nat. Protoc. 2006; 1(2):755-68). In yeast surface display, expressed antibody fragments contain an additional domain comprising the yeast agglutinin protein, Aga2p. This domain allows the antibody fragment fusion protein to attach to the outer surface of the yeast cell through the formation of disulphide bonds with surface-expressed Aga1p. The result is a yeast cell, coated in a particular antibody fragment. Display libraries of cDNA encoding these antibody fragments are utilized initially in which the antibody fragments each have a unique sequence. These fusion proteins are expressed on the cell surface of millions of yeast cells where they can interact with a desired antigenic target antigen, incubated with the cells. Target antigens may be covalently or otherwise modified with a chemical or magnetic group to allow for efficient cell sorting after successful binding with a suitable antibody fragment takes place. Recovery may be by way of magnetic-activated cell sorting (MACS), fluorescence-activated cell sorting (FACS) or other cell sorting methods known in the art. Once a subpopulation of yeast cells is selected, the corresponding plasmids may be analyzed to determine the CDR sequence.

Bacteriophage display technology typically utilizes filamentous phage including, but not limited to fd, F1 and M13 virions. Such strains are non-lytic, allowing for continued propagation of the host and increased viral titres. Examples of phage display methods that can be used to make the antibodies of the present invention include those disclosed in Miersch et al. (Miersch, S. et al., *Synthetic antibodies: Concepts, potential and practical considerations*. Methods. 2012 August; 57(4):486-98), Bradbury et al. (Bradbury, A. R. et al., *Beyond natural antibodies: the power of in vitro display technologies*. Nat. Biotechnol. 2011 March; 29(3):245-54), Brinkman et al. (Brinkmann, U. et al., *Phage display of disulfide-stabilized Fv fragments*. J Immunol Methods. 1995 May 11; 182(1):41-50); Ames et al. (Ames, R. S. et al., *Conversion of murine Fabs isolated from a combinatorial phage display library to full length immunoglobulins*. J Immunol Methods. 1995 Aug. 18; 184(2):177-86); Kettleborough et al. (Kettleborough, C. A. et al., *Isolation of tumor cell-specific single-chain Fv from immunized mice using phage-antibody libraries and the re-construction of whole antibodies from these antibody fragments*. Eur J. Immunol. 1994 April; 24(4):952-8); Persic et al. (Persic, L. et al., *An integrated vector system for the eukaryotic expression of antibodies or their fragments after selection from phage display libraries*. Gene. 1997 Mar. 10; 187(1):9-18); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108, each of which is incorporated herein by reference in its entirety. Antibody fragment expression on bacteriophages may be carried out by inserting the cDNA encoding the fragment into the gene expressing a viral coat protein. The viral coat of filamentous bacteriophages is made up of five coat proteins, encoded by a single-stranded genome. Coat protein pIII is the preferred protein for antibody fragment expression, typically at the N-terminus. If antibody fragment expression compromises the function of pIII, viral function may be restored through coexpression of a wild type pIII, although such expression will reduce the number of antibody fragments expressed on the viral coat, but may enhance access to the antibody fragment by the target antigen. Expression of viral as well as antibody fragment proteins may alternatively be encoded on multiple plasmids. This method may be used to reduce the overall size of infective plasmids and enhance the transformation efficiency.

As described above, after selection of a host expressing a high affinity antibody or antibody fragment, the coding regions from the antibody or antibody fragment can be isolated and used to generate whole antibodies, including human antibodies, or any other desired antigen binding fragment, and expressed in any desired host, including mammalian cells, insect cells, plant cells, yeast, and bacteria, e.g., as described in detail below.

The DNA sequence encoding a high affinity antibody can be mutated for additional rounds of selection in a process known as affinity maturation. The term "affinity maturation", as used herein, refers to a method whereby antibodies are produced with increasing affinity for a given antigen through successive rounds of mutation and selection of antibody- or antibody fragment-encoding cDNA sequences. In a preferred embodiment, this process is carried out in vitro. To accomplish this, amplification of CDR coding sequences may be carried out using error-prone PCR to produce millions of copies containing mutations including, but not limited to point mutations, regional mutations, insertional mutations and deletional mutations. As used herein, the term "point mutation" refers to a nucleic acid mutation in which one nucleotide within a nucleotide sequence is changed to a different nucleotide. As used herein, the term "regional mutation" refers to a nucleic acid mutation in which two or more consecutive nucleotides are changed to different nucleotides. As used herein, the term "insertional mutation" refers to a nucleic acid mutation in which one or more nucleotides are inserted into a nucleotide sequence. As used herein, the term "deletional mutation" refers to a nucleic acid mutation in which one or more nucleotides are removed from a nucleotide sequence. Insertional or deletional mutations may include the complete replacement of an entire codon or the change of one codon to another by altering one or two nucleotides of the starting codon.

Mutagenesis may be carried out on CDR-encoding cDNA sequences to create millions of mutants with singular mutations in CDR heavy and light chain regions. In another approach, random mutations are introduced only at CDR residues most likely to improve affinity. These newly generated mutagenic libraries can be used to repeat the process to screen for clones that encode antibody fragments with even higher affinity for the target antigen. Continued rounds of mutation and selection promote the synthesis of clones with greater and greater affinity (Chao, G. et al., *Isolating and engineering human antibodies using yeast surface display*. Nat. Protoc. 2006; 1(2):755-68).

Examples of techniques that can be used to produce antibodies and antibody fragments, such as Fabs and scFvs, include those described in U.S. Pat. Nos. 4,946,778 and 5,258, 498; Miersch et al. (Miersch, S. et al., *Synthetic antibodies: Concepts, potential and practical considerations*. Methods. 2012 August; 57(4):486-98), Chao et al. (Chao, G. et al., *Isolating and engineering human antibodies using yeast surface display*. Nat. Protoc. 2006; 1(2):755-68), Huston et al. (Huston, J. S. et al., *Protein engineering of single-chain Fv analogs and fusion proteins*. Methods Enzymol. 1991; 203: 46-88); Shu et al. (Shu, L. et al., *Secretion of a single-gene-encoded immunoglobulin from myeloma cells*. Proc Natl Acad Sci USA. 1993 Sep. 1; 90(17):7995-9); and Skerra et al. (Skerra, A. et al., *Assembly of a functional immunoglobulin Fv fragment in Escherichia coli*. Science. 1988 May 20; 240 (4855):1038-41), each of which is incorporated herein by reference in its entirety.

For some uses, including the in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal immunoglobulin and a human immunoglobulin constant region. Methods for producing chimeric antibodies are known in the art. (Morrison, S. L., *Transfectomas provide novel chimeric antibodies*. Science. 1985 Sep. 20; 229(4719): 1202-7; Gillies, S. D. et al., *High-level expression of chimeric antibodies using adapted cDNA variable region cassettes*. J Immunol Methods. 1989 Dec. 20; 125(1-2):191-202; and U.S. Pat. Nos. 5,807,715; 4,816,567; and 4,816,397, which are incorporated herein by reference in their entirety). Humanized antibodies are antibody molecules from non-human species that bind to the desired antigen and have one or more complementarity determining regions (CDRs) from the nonhuman species and framework regions from a human immunoglobulin molecule. Often, framework residues in the human framework regions are substituted with corresponding residues from the CDR and framework regions of the donor antibody to alter, preferably improve, antigen binding. These framework substitutions are identified by methods well known in the art, e.g., by modeling of the interactions of the CDR and framework residues to identify framework residues important for antigen binding, and by sequence comparison to identify unusual framework residues at particular positions. (U.S. Pat. Nos. 5,693,762 and 5,585,089; Riechmann, L. et al., *Reshaping human antibodies for therapy.* Nature. 1988 Mar. 24; 332(6162):323-7, which are incorporated herein by reference in their entireties). Antibodies can be humanized using a variety of techniques known in the art, including, for example, CDR-grafting (EP 239,400; PCT publication WO 91/09967; U.S. Pat. Nos. 5,225,539; 5,530, 101; and 5,585,089); veneering or resurfacing (EP 592,106; EP 519,596; Padlan, E. A., *A possible procedure for reducing the immunogenicity of antibody variable domains while preserving their ligand-binding properties.* Mol. Immunol. 1991 April-May; 28(4-5):489-98; Studnicka, G. M. et al., *Human-engineered monoclonal antibodies retain full specific binding activity by preserving non-CDR complementarity-modulating residues.* Protein Eng. 1994 June; 7(6):805-14; Roguska, M. A. et al., *Humanization of murine monoclonal antibodies through variable domain resurfacing.* Proc Natl Acad Sci USA. 1994 Feb. 1; 91(3):969-73); and chain shuffling (U.S. Pat. No. 5,565,332); each of which is incorporated herein by reference in their entirety.

Completely human antibodies are particularly desirable for therapeutic treatment of human patients, so as to avoid or alleviate immune reaction to foreign protein. Human antibodies can be made by a variety of methods known in the art, including the antibody display methods described above, using antibody libraries derived from human immunoglobulin sequences. See also, U.S. Pat. Nos. 4,444,887 and 4,716, 111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin polynucleotides. For example, the human heavy and light chain immunoglobulin polynucleotide complexes can be introduced randomly, or by homologous recombination, into mouse embryonic stem cells. Alternatively, the human variable region, constant region, and diversity region may be introduced into mouse embryonic stem cells, in addition to the human heavy and light chain polynucleotides. The mouse heavy and light chain immunoglobulin polynucleotides can be rendered nonfunctional separately or simultaneously with the introduction of human immunoglobulin loci by homologous recombination. In particular, homozygous deletion of the $J_H$ region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a glycan, glycoconjugate and/or polypeptide of the invention.

Thus, using such a technique, it is possible to produce useful human IgG, IgA, IgM, IgD and IgE antibodies. For an overview of the technology for producing human antibodies, see Lonberg and Huszar (Lonberg, N. et al., *Human antibodies from transgenic mice.* Int Rev Immunol. 1995; 13(1):65-93). For a detailed discussion of the technology for producing human antibodies and human monoclonal antibodies and protocols for producing such antibodies, see, e.g., PCT publications WO 98/24893; WO 92/01047; WO 96/34096; WO 96/33735; U.S. Pat. Nos. 5,413,923; 5,625,126; 5,633,425; 5,569,825; 5,661,016; 5,545,806; 5,814,318; 5,885,793; 5,916,771; 5,939,598; 6,075,181; and 6,114,598, each of which are incorporated by reference herein in their entirety. In addition, companies such as Abgenix, Inc. (Fremont, Calif.), Protein Design Labs, Inc. (Mountain View, Calif.) and Genpharm (San Jose, Calif.) can be engaged to provide human antibodies directed against a selected antigen using technology similar to the above described technologies.

Once an antibody molecule of the present invention has been produced by an animal, a cell line, chemically synthesized, or recombinantly expressed, it can be purified (i.e., isolated) by any method known in the art for the purification of an immunoglobulin or polypeptide molecule, for example, by chromatography (e.g., ion exchange, affinity, particularly by affinity for the specific antigen, Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The preparation of antibodies, whether monoclonal or polyclonal, is known in the art. Techniques for the production of antibodies are well known in the art and described, e.g. in Harlow and Lane "Antibodies, A Laboratory Manual", Cold Spring Harbor Laboratory Press, 1988 and Harlow and Lane "Using Antibodies: A Laboratory Manual" Cold Spring Harbor Laboratory Press, 1999.

Targets

Glycan-interacting antibodies of the present invention exert their effects via binding (reversibly or irreversibly) to one or more targets. In some embodiments, glycan-interacting antibodies can be prepared from any region of the targets taught herein. In some embodiments, targets of the present invention comprise glycans. Glycans used for generating antibodies may comprise a chain of sugars comprising at least 2, at least 3, at least 4, at least 5, at least 6, at least 7, at least 8, at least 9, at least 10, at least 11, at least 12, at least 13, at least 14, at least 15, at least 16, at least 17, at least 18, at least 19 or at least 20 residues. Preferably, glycans used for generating antibodies comprise from about 2 residue to about 5 residues.

In some embodiments, glycan-interacting antibody target antigens comprise sialic acids. N-acetylneuraminic acid (Neu5Ac) and N-glycolylneuraminic acid (Neu5Gc) are the major sialic acids on mammalian cell surfaces. Of these, Neu5Ac is naturally produced in humans. Neu5Gc is naturally produced in most mammals with the exception of humans due to a mutation in the cytidine monophosphate (CMP)-N-acetylneuraminic acid hydroxylase (CMAH) gene responsible for CMP-Neu5Gc production from CMP-Neu5Ac. Neu5Gc in humans is in fact immunogenic with nearly all humans expressing anti-Neu5Gc antibodies. Despite a lack of production, most human systems comprise some level of Neu5Gc due to dietary intake. These foreign products are subsequently incorporated into human glycoproteins. Such glycoproteins are contemplated as targets of the invention. Glycan target antigens of the present invention, include, but are not limited to those listed in Table 1.

TABLE 1

Glycan target antigens
Glycan

GalNAcα-R
Galα1,3Galβ1,4GlcNAcβ-R
Galβ1,3GalNAcβ-R
Galβ1,3GlcNAcα-R
Galβ1,3GlcNAcβ1,3Galβ1,4Glcβ-R
Galβ1,3GlcNAcβ-R
Galβ1,4GlcNAc6Sβ-R
Galβ1,4GlcNAcβ-R
Galβ1,4Glcβ-R
KDNα2,8Neu5Acα2,3Galβ1,4Glcβ-R
KDNα2,8Neu5Gcα2,3Galβ1,4Glcβ-R
Neu5,9Ac2α2,3Galβ1,3GalNAcα-R
Neu5,9Ac2α2,3Galβ1,3GalNAcβ-R
Neu5,9Ac2α2,3Galβ1,3GlcNAcβ-R
Neu5,9Ac2α2,3Galβ1,4GlcNAcβ-R
Neu5,9Ac2α2,3Galβ1,4Glcβ-R
Neu5,9Ac2α2,3Galβ-R
Neu5,9Ac2α2,6GalNAcα-R
Neu5,9Ac2α2,6Galβ1,4GlcNAcβ-R
Neu5,9Ac2α2,6Galβ1,4Glcβ-R
Neu5,9Ac2α2,6Galβ-R
Neu5Acα2,3Galβ1,3GalNAcα-R
Neu5Acα2,3Galβ1,3GalNAcβ-R
Neu5Acα2,3Galβ1,3GlcNAcβ1,3Galβ1,4Glcβ-R
Neu5Acα2,3Galβ1,3GlcNAcβ-R
Neu5Acα2,3Galβ1,4(Fucα1,3)GlcNAc6Sβ-R
Neu5Acα2,3Galβ1,4(Fucα1,3)GlcNAcβ-R
Neu5Acα2,3Galβ1,4GlcNAc6Sβ-R
Neu5Acα2,3Galβ1,4GlcNAcβ-R
Neu5Acα2,3Galβ1,4Glcβ-R
Neu5Acα2,3Galβ-R
Neu5Acα2,6(KDNα2,3)Galβ1,4Glcβ-R
Neu5Acα2,6(Neu5Acα2,3)Galβ1,4Glcβ-R
Neu5Acα2,6(Neu5Gcα2,3)Galβ1,4Glcβ-R
Neu5Acα2,6GalNAcα-R
Neu5Acα2,6Galβ1,4GlcNAcβ-R
Neu5Acα2,6Galβ1,4Glcβ-R
Neu5Acα2,6Galβ-R
Neu5Acα2,8KDNα2,6Galβ1,4Glcβ-R
Neu5Acα2,8Neu5Acα2,3Galβ1,4Glcβ-R
Neu5Acα2,8Neu5Acα2,3Galβ1,4Glcβ-R
Neu5Acα2,8Neu5Acα2,6Galβ1,4Glcβ-R
Neu5Acα2,8Neu5Acα2,8Neu5Acα2,3Galβ1,4Glcβ-R
Neu5Acα2,8Neu5Acα2,8Neu5Acα2,3Galβ1,4Glcβ-R
Neu5Acα2,8Neu5Gcα2,3Galβ1,4Glcβ-R
Neu5Acα2,8Neu5Gcα2,6Galβ1,4Glcβ-R
Neu5Gc9Acα2,3Galβ1,4Glcβ-R
Neu5Gc9Acα2,6Galβ1,4Glcβ-R
Neu5Gc9Acα2,3Galβ1,3GalNAcα-R
Neu5Gc9Acα2,3Galβ1,3GalNAcβ-R
Neu5Gc9Acα2,3Galβ1,3GlcNAcβ-R
Neu5Gc9Acα2,3Galβ1,4GlcNAcβ-R
Neu5Gc9Acα2,3Galβ-R
Neu5Gc9Acα2,6GalNAcα-R
Neu5Gc9Acα2,6Galβ1,4GlcNAcβ-R
Neu5Gc9Acα2,6Galβ-R
Neu5GcOMeα2,8Neu5Acα2,3Galβ1,4Glcβ-R
Neu5Gcα2,3Galβ1,3GalNAcα-R
Neu5Gcα2,3Galβ1,3GalNAcβ-R
Neu5Gcα2,3Galβ1,3GlcNAcβ1,3Galβ1,4Glcβ-R
Neu5Gcα2,3Galβ1,3GlcNAcβ-R
Neu5Gcα2,3Galβ1,4(Fucα1,3)GlcNAc6Sβ-R
Neu5Gcα2,3Galβ1,4(Fucα1,3)GlcNAcβ-R
Neu5Gcα2,3Galβ1,4GlcNAc6Sβ-R
Neu5Gcα2,3Galβ1,4GlcNAcβ-R
Neu5Gcα2,3Galβ1,4Glcβ-R
Neu5Gcα2,3Galβ-R
Neu5Gcα2,6GalNAcα-R
Neu5Gcα2,6Galβ1,4GlcNAcβ-R
Neu5Gcα2,6Galβ1,4Glcβ-R
Neu5Gcα2,6Galβ-R
Neu5Gcα2,8Neu5Acα2,3Galβ1,4Glcβ-R
Neu5Gcα2,8Neu5Gcα2,3Galβ1,4Glcβ-R

The following abbreviations are used herein: Glc—glucose, Gal—galactose, GlcNAc—N-acetylglucosamine, GalNAc—N-acetylgalactosamine, GlcNAc6S—6-Sulfo-N-acetylglucosamine, KDN—2-keto-3-deoxy-D-glycero-D-galactononic acid, Neu-5,9Ac2—N-acetyl-9-O-acetylneuraminic acid, Fuc—fucose and Neu5GcOMe—2-O-methyl-N-glycolylneuraminic acid. O-glycosidic bonds are present between each residue in the glycans listed with α and β indicating the relative stoichiometry between the two residues joined by the bond, wherein a indicates an axial orientation and β indicates an equatorial orientation. The numbers following α and/or β, in the format x,x, indicated the carbon number of each of the carbons from each of the adjoined residues that participate in bond formation. While the glycans listed in Table 1 represent individual glycan target antigens contemplated, the present invention also includes embodiments wherein the above presented glycans comprise different combinations of α and β-oriented O-glycosidic bonds than the ones presented. Also in Table 1, R represents an entity that the glycan may be coupled with. In some embodiments, R is a protein wherein the glycan is linked typically to a serine or threonine residue. In some embodiments, R is a linker molecule used to join the glycan to a substrate, such as in a glycan array. In some embodiments, R may be a linker comprising —(CH$_2$)$_2$CH$_2$NH$_2$ or —(CH$_2$)$_3$NHCOCH$_2$(OCH$_2$CH$_2$)$_6$NH$_2$. In some embodiments, R may be biotin, albumin, ProNH$_2$, —CH—, —OH, —OCH$_3$, —OCH$_2$CH$_3$, —H, hydrido, hydroxy, alkoxyl, oxygen, carbon, sulfur, nitrogen, polyacrylamide, phosphorus, NH$_2$, ProNH$_2$=O(CH$_2$)$_2$CH$_2$NH$_2$, (OCH$_2$CH$_2$)$_6$NH$_2$, O(CH$_2$)$_3$NHCOCH$_2$ (OCH$_2$CH$_2$)$_6$NH$_2$, the fluorescent labels 2-aminobenzamide (AB) and/or 2-aminobenzoid acid (AA), 2-aminobenzamide analog that contains an alkyl amine (AEAB), aminooxy-groups, methylaminooxygroups, hydrazide groups, amino lipid 1,2-dihexadecyl-sn-glycero-3-phosphoethanolamine (DHPE), aminooxy (AO) functionalized DHPE and glycosylphosphatidylinositol (GPI). Without intending to limit the source or nature of R, this may include structures that affect the physical spacing of glycan residue. In some embodiments, the R group may comprise a combination of the R groups presented here, e.g. a biotinylated polyacrylamide. In some embodiments, the R group in combination with underlying substrates effect glycan residue spacing.

Glycan targets of the present invention may comprise regions of antibody recognition. As used herein, the term "region of antibody recognition" refers to one or more regions located on any part of the molecule, an attached group or located on a region of interaction between the glycan and another molecule, including, but not limited to another glycan. In some embodiments, regions of antibody recognition are located at interchain target sites, wherein the term interchain means within the present polymeric chain. Interchain target sites may comprise regions of antibody recognition comprising 1, 2, 3, 4, 5, 6, 7, 8, 9 or at least 10 residues, bonds between residues or combinations of residues and bonds. In some embodiments, regions of antibody recognition are located at regions of interaction between one or more glycan chains. Such regions may be between 2, 3, 4 or at least 5 glycan chains. In some embodiments, regions of antibody recognition are located at regions of interaction between glycan branch chains connected to a common parent chain. In some embodiments, regions of antibody recognition are located at regions of interaction between a glycan branch chain and a parent chain. In some embodiments, regions of antibody recognition are located at regions of interaction between glycans and proteins. Such regions of interaction may comprise chemical bonds between the glycan and the protein, including, but not limited to covalent bonds, ionic bonds, hydrostatic bonds, hydrophobic bonds and hydrogen bonds. In some embodiments, regions of antibody recognition are located at regions of interaction between glycans and other biomolecules including, but not limited to lipids and nucleic acids. Such regions of interaction may comprise chemical bonds between the glycan and the biomolecule, including, but not limited to covalent bonds, ionic bonds, hydrostatic bonds, hydrophobic bonds and hydrogen bonds.

In some embodiments, glycan targets of the present invention are components of glycoconjugates. As used herein, the term "glycoconjugate" refers to any entity comprising a glycan moiety. In some embodiments, glycoconjugates are glycolipids. As used herein, the term "glycolipid" refers to a class of lipids wherein a carbohydrate moiety is covalently attached. In some embodiments, carbohydrate moieties present on glycolipids comprise glycans. In some embodiments, lipid components of glycolipids comprise ceramide moieties. Examples of glycolipids contemplated as targets of the present invention include, but are not limited to glyceroglycolipids (including, but not limited to galactolipids and sulfolipids), glycosphingolipids (including, but not limited to cerebrosides (e.g., galactocerebrosides, glucocerebrosides and sulfatides), gangliosides, globosides and glycophosphosphingolipids) and glycosylphosphatidylinositols. When located within cell membranes, glycan moieties of glycolipids are located on the extracellular side of the membrane where they may interact with other cells as well as cell signaling ligands (Maccioni, H. J. et al., Organization of the synthesis of glycolipid oligosaccharides in the Golgi complex. FEBS Lett. 2011 Jun. 6; 585(11):1691-8).

In some embodiments, glycoconjugate targets of the present invention are glycoprotein and/or proteoglycans. Glycoproteins refer to any proteins that are covalently bonded with glycans. Proteoglycans are a class of proteins that are heavily glycosylated with glycans that often carry a negative charge. This property makes them very hydrophilic and important components of connective tissue.

Cancer-Related Targets

In some embodiments, targets of the present invention are cancer-related antigens or epitopes. As used herein, the term "cancer-related" is used to describe entities that may be in some way associated with cancer, cancerous cells and/or cancerous tissues. Many antigens comprising glycans have been identified that are expressed in correlation with cancer (Heimburg-Molinaro, J. et al., Cancer vaccines and carbohydrate epitopes. Vaccine. 2011 Nov. 8; 29(48):8802-26). These cancer-related antigens include, but are not limited to mucin-related antigens [including, but not limited to Tn, Sialyl Tn (STn) and Thomsen-Friedenreich antigen], blood group Lewis related antigens [including, but not limited to Lewis$^Y$ (Le$^Y$), Lewis$^X$ (Le$^X$), Sialyl Lewis$^X$ (SLe$^X$) and Sialyl Lewis$^A$ (SLe$^A$)], glycosphingolipid-related antigens [including, but not limited to Globo H, stage-specific embryonic antigen-3 (SSEA-3) and glycosphingolipids comprising sialic acid], ganglioside-related antigens [including, but not limited to gangliosides GD2, GD3, GM2, fucosyl GM1 and Neu5GcGM3] and polysialic acid-related antigens. Many of such antigens are described in co-pending and co-owned application number PCT/US2011/021387, herein incorporated by reference in its entirety.

In some embodiments, cancer-related targets of the present invention include Lewis blood group antigens. Lewis blood group antigens comprise a fucose residue linked to GlcNAc by an α1-3 linkage or an α1-4 linkage. They may be found on both glycolipids and glycoproteins. Lewis blood group antigens may be found in the body fluid of individuals that are secretors of these antigens. Their appearance on red cells is due to absorption of Lewis antigens from the serum by the red cells.

In some embodiments, cancer-related targets of the present invention comprise Le$^Y$. Le$^Y$ (also known as CD174) is made up of Galβ1,4GlcNAc comprising α1,2- as well as α1,3-linked fucose residues yielding the Fucα(1,2)Galβ(1,4)Fucα(1,3)GlcNAc epitope. It is synthesized from the H antigen by α-1,3 fucosyltransferases which attach the α1,3 fucose to the GlcNAc residue of the parent chain. Le$^Y$ may be expressed in a variety of cancers including, but not limited to ovarian, breast, prostate, colon, lung and epithelial. Due to its low expression level in normal tissues and elevated expression level in many cancers, the Le$^Y$ antigen is an attractive target for therapeutic antibodies.

In some embodiments, cancer-related targets of the present invention comprise Le$^X$. Le$^X$ comprises the epitope Galβ1-4(Fucα1-3)GlcNAcβ-R. It is also known as CD15 and stage-specific embryonic antigen-1 (SSEA-1). This antigen was first recognized as being immunoreactive with sera taken from a mouse subjected to immunization with F9 teratocarcinoma cells. Le$^X$ was also found to correlate with embryonic development at specific stages. It is also expressed in a variety of tissues both in the presence and absence of cancer, but can also be found in breast and ovarian cancers where it is only expressed by cancerous cells.

In some embodiments, cancer-related targets of the present invention comprise SLe$^A$ and/or SLe$^X$. SLe$^A$ and SLe$^X$ comprise the structures [Neu5Acα2-3Galβ1-3(Fucα1-4)GlcNAcβ-R] and [Neu5Acα2-3Galβ1-4(Fucα1-3)GlcNAcβ-R] respectively. Their expression is upregulated in cancer cells. The presence of these antigens in serum correlates with malignancy and poor prognosis. SLe$^X$ is mostly found as a mucin terminal epitope. It is expressed in a number of different cancers including breast, ovarian, melanoma, colon, liver, lung and prostate. In some embodiments of the present invention, SLe$^A$ and SLe$^X$ targets comprise Neu5Gc (referred to herein as GcSLe$^A$ and GcSLe$^X$, respectively).

In some embodiments, cancer-related targets of the present invention comprise glycolipids and/or epitopes present on glycolipids, including, but not limited to glycosphingolipids. Glycosphingolipids comprise the lipid ceramide linked to a glycan by the ceramide hydroxyl group. On the cell membrane, glycosphingolipids form clusters referred to as "lipid rafts".

In some embodiments, cancer-related targets of the present invention comprise Globo H. Globo H is a cancer-related glycosphingolipid first identified in breast cancer cells. The glycan portion of Globo H comprises Fucα(1-2)Galβ(1-3)GalNAcβ(1-3)Galα(1-4)Galβ(1-4)Glcβ(1). Although found in a number of normal epithelial tissues, Globo H has been identified in association with many tumor tissues including, but not limited to, small cell lung, breast, prostate, lung, pancreatic, gastric, ovarian and endometrial tumors.

In some embodiments, cancer-related glycosphingolipid targets of the present invention include gangliosides. Gangliosides are glycosphingolipids comprising sialic acid. According to ganglioside nomenclature, G is used as an abbreviation for ganglioside. This abbreviation is followed by the letters M, D or T referring to the number of sialic acid residues attached (1, 2 or 3 respectively). Finally the numbers 1, 2 or 3 are used to refer to the order of the distance each migrates when analyzed by thin layer chromatography (wherein 3 travels the greatest distance, followed by 2 and then 1). Gangliosides are known to be involved in cancer-related growth and metastasis and are expressed on the cell surface of tumor cells. Gangliosides expressed on tumor cells include, but are not limited to GD2, GD3, GM2 and fucosyl GM1 (also referred to herein as Fuc-GM1). In some embodiments of the present invention, glycan-interacting antibodies are directed toward GD3. GD3 is a regulator of cell growth. In some embodiments, GD3-directed antibodies are used to modulate cell growth and/or angiogenesis. In some embodiments, GD3-directed antibodies are used to modulate cell attachment. In some embodiments of the present invention, glycan interacting antibodies are directed toward GM2. In some embodiments, GM2-directed antibodies are used to modulate cell to cell contact. In some embodiments, ganglioside targets of the present invention comprise Neu5Gc. In some embodiments, such targets may include a GM3 variant comprising Neu5Gc (referred to herein as GcGM3). The glycan component of GcGM3 is Neu5Gcα2-3Galβ1-4Glc. GcGM3 is a known component of tumor cells.

In some embodiments, cancer-related antigens of the present invention comprise Neu5Gc.

Immunogenic Hosts

In some embodiments, glycan-interacting antibodies of the present invention may be developed through the use of non-human animals as hosts for immunization, referred to herein as "immunogenic hosts". In some embodiments, immunogenic hosts are mammals. In some embodiments, immunogenic hosts are transgenic knockout mice. Antigens comprising target sites and/or epitope targets of glycan-interacting antibodies may be to contact immunogenic hosts in order to stimulate an immune response and produce antibodies in the immunogenic host that specifically bind the target sites and/or epitope targets present on the antigens introduced. Antibodies produced in this manner may be isolated from serum of the immunogenic hosts. Antibody producing cells from the immunogenic hosts may also be used to generate cell lines that produce the desired antibody. In some embodiments, screening for antibodies and/or antibody producing cells from the immunogenic host may be carried out through the use of enzyme-linked immunosorbent assays (ELISAs) and/or glycan arrays.

Glycan Arrays

In some embodiments, glycan-interacting antibodies of the present invention may be developed through the use of glycan arrays. As used herein, the term "glycan array" refers to a tool used to identify agents that interact with any of a number of different glycans linked to the array substrate. In some embodiments, glycan arrays comprise a number of chemically-synthesized glycans, referred to herein as "glycan probes". In some embodiments, glycan arrays comprise at least 2, at least 5, at least 10, at least 20, at least 30, at least 40, at least 50, at least 60, at least 70, at least 80, at least 90, at least 100, at least 150, at least 350, at least 1000 or at least 1500 glycan probes. In some embodiments, glycan arrays may be customized to present a desired set of glycan probes. In some embodiments, glycan probes may be attached to the array substrate by a linker molecule. Such linkers may comprise molecules including, but not limited to —O(CH$_2$)$_2$CH$_2$)NH$_2$ and O(CH$_2$)$_3$NHCOCH$_2$(OCH$_2$CH$_2$)$_6$NH$_2$.

Proteins and Variants

Glycan-interacting antibodies of the present invention may exist as a whole polypeptide, a plurality of polypeptides or fragments of polypeptides, which independently may be encoded by one or more nucleic acids, a plurality of nucleic acids, fragments of nucleic acids or variants of any of the aforementioned. As used herein, "polypeptide" means a polymer of amino acid residues (natural or unnatural) linked together most often by peptide bonds. The term, as used herein, refers to proteins, polypeptides, and peptides of any size, structure, or function. In some instances the polypeptide encoded is smaller than about 50 amino acids and the polypeptide is then termed a peptide. If the polypeptide is a peptide, it will be at least about 2, 3, 4, or at least 5 amino acid residues long. Thus, polypeptides include gene products, naturally occurring polypeptides, synthetic polypeptides, homologs, orthologs, paralogs, fragments and other equivalents, variants, and analogs of the foregoing. A polypeptide may be a single molecule or may be a multi-molecular complex such as a dimer, trimer or tetramer. They may also comprise single chain or multichain polypeptides and may be associated or linked. The term polypeptide may also apply to amino acid polymers in which one or more amino acid residues are an artificial chemical analogue of a corresponding naturally occurring amino acid.

The term "polypeptide variant" refers to molecules which differ in their amino acid sequence from a native or reference sequence. The amino acid sequence variants may possess substitutions, deletions, and/or insertions at certain positions within the amino acid sequence, as compared to a native or reference sequence. Ordinarily, variants will possess at least about 50% identity (homology) to a native or reference sequence, and preferably, they will be at least about 80%, more preferably at least about 90% identical (homologous) to a native or reference sequence.

In some embodiments "variant mimics" are provided. As used herein, the term "variant mimic" is one which contains one or more amino acids which would mimic an activated sequence. For example, glutamate may serve as a mimic for phosphoro-threonine and/or phosphoro-serine. Alternatively, variant mimics may result in deactivation or in an inactivated product containing the mimic, e.g., phenylalanine may act as an inactivating substitution for tyrosine; or alanine may act as an inactivating substitution for serine. The amino acid sequences of the glycan-interacting antibodies of the invention may comprise naturally occurring amino acids and as such may be considered to be proteins, peptides, polypeptides, or fragments thereof. Alternatively, the glycan-interacting antibodies may comprise both naturally and non-naturally occurring amino acids.

The term "amino acid sequence variant" refers to molecules with some differences in their amino acid sequences as compared to a native or starting sequence. The amino acid sequence variants may possess substitutions, deletions, and/or insertions at certain positions within the amino acid sequence. "Native" or "starting" sequence should not be confused with a wild type sequence. As used herein, a native or starting sequence is a relative term referring to an original molecule against which a comparison may be made. "Native" or "starting" sequences or molecules may represent the wild-type (that sequence found in nature) but do not have to be the wild-type sequence.

Ordinarily, variants will possess at least about 70% homology to a native sequence, and preferably, they will be at least about 80%, more preferably about 90% homologous to a native sequence.

"Homology" as it applies to amino acid sequences is defined as the percentage of residues in the candidate amino acid sequence that are identical with the residues in the amino acid sequence of a second sequence after aligning the sequences and introducing gaps, if necessary, to achieve the maximum percent homology. Methods and computer programs for the alignment are well known in the art. It is understood that homology depends on a calculation of percent identity but may differ in value due to gaps and penalties introduced in the calculation.

By "homologs" as it applies to amino acid sequences is meant the corresponding sequence of other species having substantial identity to a second sequence of a second species.

"Analogs" is meant to include polypeptide variants which differ by one or more amino acid alterations, e.g., substitutions, additions or deletions of amino acid residues that still maintain the properties of the parent polypeptide.

The present invention contemplates several types of glycan-interacting antibodies which are amino acid based including variants and derivatives. These include substitutional, insertional, deletion and covalent variants and derivatives. As such, included within the scope of this invention are glycan-interacting antibody molecules containing substitutions, insertions and/or additions, deletions and covalently modifications. For example, sequence tags or amino acids, such as one or more lysines, can be added to the peptide sequences of the invention (e.g., at the N-terminal or C-terminal ends). Sequence tags can be used for peptide purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence which is soluble, or linked to a solid support.

"Substitutional variants" when referring to proteins are those that have at least one amino acid residue in a native or starting sequence removed and a different amino acid inserted in its place at the same position. The substitutions may be single, where only one amino acid in the molecule has been substituted, or they may be multiple, where two or more amino acids have been substituted in the same molecule.

As used herein the term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine and leucine for another non-polar residue. Likewise, examples of conservative substitutions include the substitution of one polar (hydrophilic) residue for another such as between arginine and lysine, between glutamine and asparagine, and between glycine and serine. Additionally, the substitution of a basic residue such as lysine, arginine or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue.

"Insertional variants" when referring to proteins are those with one or more amino acids inserted immediately adjacent to an amino acid at a particular position in a native or starting sequence. "Immediately adjacent" to an amino acid means connected to either the alpha-carboxy or alpha-amino functional group of the amino acid.

"Deletional variants" when referring to proteins, are those with one or more amino acids in the native or starting amino acid sequence removed. Ordinarily, deletional variants will have one or more amino acids deleted in a particular region of the molecule.

As used herein, the term "derivative" is used synonymously with the term "variant" and refers to a molecule that has been modified or changed in any way relative to a reference molecule or starting molecule. In some embodiments, derivatives include native or starting proteins that have been modified with an organic proteinaceous or non-proteinaceous derivatizing agent, and post-translational modifications. Covalent modifications are traditionally introduced by reacting targeted amino acid residues of the protein with an organic derivatizing agent that is capable of reacting with selected side-chains or terminal residues, or by harnessing mechanisms of post-translational modifications that function in selected recombinant host cells. The resultant covalent derivatives are useful in programs directed at identifying residues important for biological activity, for immunoassays, or for the preparation of anti-protein antibodies for immunoaffinity purification of the recombinant glycoprotein. Such modifications are within the ordinary skill in the art and are performed without undue experimentation.

Certain post-translational modifications are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Either form of these residues may be present in the proteins used in accordance with the present invention.

Other post-translational modifications include hydroxylation of proline and lysine, phosphorylation of hydroxyl groups of seryl or threonyl residues, methylation of the alpha-amino groups of lysine, arginine, and histidine side chains (T. E. Creighton, Proteins: Structure and Molecular Properties, W.H. Freeman & Co., San Francisco, pp. 79-86 (1983)).

Covalent derivatives specifically include fusion molecules in which proteins of the invention are covalently bonded to a non-proteinaceous polymer. The non-proteinaceous polymer ordinarily is a hydrophilic synthetic polymer, i.e. a polymer not otherwise found in nature. However, polymers which exist in nature and are produced by recombinant or in vitro methods are useful, as are polymers which are isolated from nature. Hydrophilic polyvinyl polymers fall within the scope of this invention, e.g. polyvinylalcohol and polyvinylpyrrolidone. Particularly useful are polyvinylalkylene ethers such a polyethylene glycol, polypropylene glycol. The proteins may be linked to various non-proteinaceous polymers, such as polyethylene glycol, polypropylene glycol or polyoxyalkylenes, in the manner set forth in U.S. Pat. No. 4,640,835; 4,496,689; 4,301,144; 4,670,417; 4,791,192 or 4,179,337.

"Features" when referring to proteins are defined as distinct amino acid sequence-based components of a molecule. Features of the proteins of the present invention include surface manifestations, local conformational shape, folds, loops, half-loops, domains, half-domains, sites, termini or any combination thereof.

As used herein when referring to proteins the term "surface manifestation" refers to a polypeptide based component of a protein appearing on an outermost surface.

As used herein when referring to proteins the term "local conformational shape" means a polypeptide based structural manifestation of a protein which is located within a definable space of the protein.

As used herein when referring to proteins the term "fold" means the resultant conformation of an amino acid sequence upon energy minimization. A fold may occur at the secondary or tertiary level of the folding process. Examples of secondary level folds include beta sheets and alpha helices. Examples of tertiary folds include domains and regions formed due to aggregation or separation of energetic forces. Regions formed in this way include hydrophobic and hydrophilic pockets, and the like.

As used herein the term "turn" as it relates to protein conformation means a bend which alters the direction of the backbone of a peptide or polypeptide and may involve one, two, three or more amino acid residues.

As used herein when referring to proteins the term "loop" refers to a structural feature of a peptide or polypeptide which reverses the direction of the backbone of a peptide or polypeptide and comprises four or more amino acid residues. Oliva et al. have identified at least 5 classes of protein loops (J. Mol. Biol 266 (4): 814-830; 1997).

As used herein when referring to proteins the term "half-loop" refers to a portion of an identified loop having at least half the number of amino acid resides as the loop from which it is derived. It is understood that loops may not always contain an even number of amino acid residues. Therefore, in those cases where a loop contains or is identified to comprise an odd number of amino acids, a half-loop of the odd-numbered loop will comprise the whole number portion or next whole number portion of the loop (number of amino acids of the loop/2+/−0.5 amino acids). For example, a loop identified as a 7 amino acid loop could produce half-loops of 3 amino acids or 4 amino acids (7/2=3.5+/−0.5 being 3 or 4).

As used herein when referring to proteins the term "domain" refers to a motif of a polypeptide having one or more identifiable structural or functional characteristics or properties (e.g., binding capacity, serving as a site for protein-protein interactions.

As used herein when referring to proteins the term "half-domain" means portion of an identified domain having at least half the number of amino acid resides as the domain from which it is derived. It is understood that domains may not always contain an even number of amino acid residues. Therefore, in those cases where a domain contains or is identified to comprise an odd number of amino acids, a half-domain of the odd-numbered domain will comprise the whole number portion or next whole number portion of the domain (number of amino acids of the domain/2+/−0.5 amino acids). For example, a domain identified as a 7 amino acid domain could produce half-domains of 3 amino acids or 4 amino acids (7/2=3.5+/−0.5 being 3 or 4). It is also understood that sub-domains may be identified within domains or half-domains, these subdomains possessing less than all of the structural or functional properties identified in the domains or half domains from which they were derived. It is also understood that the amino acids that comprise any of the domain types herein need not be contiguous along the backbone of the polypeptide (i.e., nonadjacent amino acids may fold structurally to produce a domain, half-domain or subdomain).

As used herein when referring to proteins the terms "site" as it pertains to amino acid based embodiments is used synonymous with "amino acid residue" and "amino acid side chain". A site represents a position within a peptide or polypeptide that may be modified, manipulated, altered, derivatized or varied within the polypeptide based molecules of the present invention.

As used herein the terms "termini or terminus" when referring to proteins refers to an extremity of a peptide or polypeptide. Such extremity is not limited only to the first or final site of the peptide or polypeptide but may include additional amino acids in the terminal regions. The polypeptide based molecules of the present invention may be characterized as having both an N-terminus (terminated by an amino acid with a free amino group (NH2)) and a C-terminus (terminated by an amino acid with a free carboxyl group (COOH)). Proteins of the invention are in some cases made up of multiple polypeptide chains brought together by disulfide bonds or by non-covalent forces (multimers, oligomers). These sorts of proteins will have multiple N- and C-termini. Alternatively, the termini of the polypeptides may be modified such that they begin or end, as the case may be, with a non-polypeptide based moiety such as an organic conjugate.

Once any of the features have been identified or defined as a component of a molecule of the invention, any of several manipulations and/or modifications of these features may be performed by moving, swapping, inverting, deleting, randomizing or duplicating. Furthermore, it is understood that manipulation of features may result in the same outcome as a modification to the molecules of the invention. For example, a manipulation which involved deleting a domain would result in the alteration of the length of a molecule just as modification of a nucleic acid to encode less than a full length molecule would.

Modifications and manipulations can be accomplished by methods known in the art such as site directed mutagenesis. The resulting modified molecules may then be tested for activity using in vitro or in vivo assays such as those described herein or any other suitable screening assay known in the art.

Isotopic Variations

The glycan-interacting antibodies of the present invention may contain one or more atoms that are isotopes. As used herein, the term "isotope" refers to a chemical element that has one or more additional neutron. In one embodiment, compounds of the present invention may be deuterated. As used herein, the term "deuterated" refers to a substance that has had one or more hydrogen atoms replaced by deuterium isotopes. Deuterium isotopes are isotopes of hydrogen. The nucleus of hydrogen contains one proton while deuterium nuclei contain both a proton and a neutron. The glycan-interacting antibodies may be deuterated in order to change a physical property of the compound, such as stability, or to allow the compounds to be used in diagnostic and experimental applications.

Conjugates and Combinations

It is contemplated by the present invention that the glycan-interacting antibodies of the present invention may be complexed, conjugated or combined with one or more homologous or heterologous molecules. As used herein, "homologous molecule" means a molecule which is similar in at least one of structure or function relative to a starting molecule while a "heterologous molecule" is one that differs in at least one of structure or function relative to a starting molecule. Structural homologs are therefore molecules which are substantially structurally similar. They can be identical. Functional homologs are molecules which are substantially functionally similar. They can be identical.

Glycan-interacting antibodies of the invention may comprise conjugates. Such conjugates of the invention may include a naturally occurring substance or ligand, such as a protein (e.g., human serum albumin (HSA), low-density lipoprotein (LDL), high-density lipoprotein (HDL), or globulin); a carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid, an oligonucleotide (e.g. an aptamer). Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl) methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

The conjugates can also include targeting groups, e.g., a cell or tissue targeting agent or group, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer.

Targeting groups can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Targeting groups may also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, multivalent fucose, or aptamers.

The targeting group can be any ligand that is capable of targeting a specific receptor. Examples include, without limitation, folate, GalNAc, galactose, mannose, mannose-6P, apatamers, integrin receptor ligands, chemokine receptor ligands, transferrin, biotin, serotonin receptor ligands, PSMA, endothelin, GCPII, somatostatin, LDL, and HDL ligands. In particular embodiments, the targeting group is an aptamer. The aptamer can be unmodified or have any combination of modifications disclosed herein.

In still other embodiments, glycan-interacting antibodies are covalently conjugated to a cell penetrating polypeptide. The cell-penetrating peptide may also include a signal sequence. The conjugates of the invention can be designed to have increased stability; increased cell transfection; and/or altered biodistribution (e.g., targeted to specific tissues or cell types).

Conjugating moieties may be added to glycan-interacting antibodies such that they allow labeling or flagging targets for clearance. Such tagging/flagging molecules include, but are not limited to ubiquitin, fluorescent molecules, human influenza hemaglutinin (HA), c-myc (a 10 amino acid segment of the human protooncogene myc with sequence EQKLISEEDL (SEQ ID NO: 5)), histidine (His), flag (a short peptide of sequence DYKDDDDK (SEQ ID NO: 6)), glutathione S-transferase (GST), V5 (a paramyxovirus of simian virus 5 epitope), biotin, avidin, streptavidin, horse radish peroxidase (HRP) and digoxigenin.

In some embodiments, glycan-interacting antibodies may be combined with one another or other molecule in the treatment of a disease or condition.

Nucleic Acids

The present invention embraces nucleic acid molecules. In some embodiments, nucleic acids encode glycan-interacting antibodies. Such nucleic acid molecules include, without limitation, DNA molecules, RNA molecules, polynucleotides, oligonucleotides, mRNA molecules, vectors, plasmids and the like. The present invention also embraces cell programmed or generated to express nucleic acid molecules encoding glycan-interacting antibodies.

II. Methods and Uses

Therapeutics

Oncocology-Related Applications

Aberrant glycosylation is a hallmark of cancer cell transformation. MUC1 is a key cell surface glycoprotein that is normally extensively glycosylated but is underglycosylated in tumor cells. Sparse glycosylation of MUC1 leads to exposure of immunogenic antigens, also referred to herein as "cancer-related antigens". These may be along the MUC1 core peptide sequence or along core carbohydrate residues. These antigens include, but are not limited to N-acetylgalactosamine (Tn), sialyl($\alpha$2-6)N-acetylgalactosamine (STn) and galactose($\beta$1-3)N-acetylgalactosamine (also known as Thomsen-Friedenreich antigen or TF). It has been estimated that about 80% of all carcinomas express Tn among the core carbohydrates of MUC1 with STn being strongly expressed on human carcinoma cells and linked to cancer progression and metastasis. With few exceptions, Tn and STn are not expressed in normal healthy tissues. Sialic acid forms a prominent epitope on STn. The invention takes advantage of the fact that aberrant Neu5Gc-STn (GcSTn) glycan expression appears to be highly specific to various carcinomas.

In the case of MUC1, Neu5Gc incorporation into STn yields a tumor-specific target, a site that is an attractive target for antibody-based therapies to treat tumor tissue. In some embodiments of the present invention, glycan-interacting antibodies target MUC1 expressing cancer cells comprising Neu5Gc. To date, Neu5Gc has been detected in glycoconjugates from a number of human cancer tissues including, but not limited to colon cancer, retinoblastoma tissue, melanoma, breast cancer and yolk sac tumor tissue. In some embodiments of the present invention, methods are contemplated for glycan-interacting antibody treatment of these forms of cancer as well as other forms of cancer, not specifically listed here, characterized by the presence of cancer cells comprising Neu5Gc.

Additional antigens comprising glycans have been identified that are expressed in correlation with cancer (Heimburg-Molinaro, J. et al., Cancer vaccines and carbohydrate epitopes. Vaccine. 2011 Nov. 8; 29(48):8802-26). These cancer-related antigens include, but are not limited to blood group Lewis related antigens [including, but not limited to Lewis$^Y$ (Le$^Y$), Lewis$^X$ (Le$^X$), Sialyl Lewis$^X$ (SLe$^X$) and Sialyl Lewis$^A$ (SLe$^A$)], glycosphingolipid-related antigens [including, but not limited to Globo H, stage-specific embryonic antigen-3 (SSEA-3) and glycosphingolipids comprising sialic acid], ganglioside-related antigens [including, but not limited to gangliosides GD2, GD3, GM2, fucosyl GM1 and Neu5GcGM3] and polysialic acid-related antigens.

In some embodiments, therapeutics of the present invention may be directed toward Lewis blood group antigens. Lewis blood group antigens comprise a fucose residue linked to GlcNAc by an $\alpha$1-3 linkage or an $\alpha$1-4 linkage. They may be found on both glycolipids and glycoproteins. Lewis blood group antigens may be found in the body fluid of individuals that are secretors of these antigens. Their appearance on red cells is due to absorption of Lewis antigens from the serum by the red cells.

In some embodiments, therapeutics of the present invention may be directed toward Le$^Y$. Le$^Y$ (also known as CD174) is made up of Gal$\beta$1,4GlcNAc comprising $\alpha$1,2- as well as $\alpha$1,3-linked fucose residues yielding the Fuc$\alpha$(1,2)Gal$\beta$(1,4) Fuc$\alpha$(1,3)GlcNAc epitope. It is synthesized from the H antigen by $\alpha$1,3 fucosyltransferases which attach the $\alpha$1,3 fucose to the GlcNAc residue of the parent chain. Le$^Y$ may be expressed in a variety of cancers including, but not limited to ovarian, breast, prostate, colon, lung and epithelial. Due to its low expression level in normal tissues and elevated expression level in many cancers, the Le$^Y$ antigen is an attractive target for therapeutic antibodies.

In some embodiments, therapeutics of the present invention may be directed toward Le$^X$. Le$^X$ comprises the epitope Galβ1-4(Fucα1-3)GlcNAcβ-R. It is also known as CD15 and stage-specific embryonic antigen-1 (SSEA-1). This antigen was first recognized as being immunoreactive with sera taken from a mouse subjected to immunization with F9 teratocarcinoma cells. Le$^X$ was also found to correlate with embryonic development at specific stages. It is also expressed in a variety of tissues both in the presence and absence of cancer, but can also be found in breast and ovarian cancers where it is only expressed by cancerous cells.

In some embodiments, therapeutics of the present invention may be directed toward SLe$^A$ and/or SLe$^X$. SLe$^A$ and SLe$^X$ comprise the structures [Neu5Acα2-3Galβ1-3(Fucα1-4)GlcNAcβ-R] and [Neu5Acα2-3Galβ1-4(Fucα1-3)GlcNAcβ-R] respectively. Their expression is upregulated in cancer cells. The presence of these antigens in serum correlates with malignancy and poor prognosis. SLe$^X$ is mostly found as a mucin terminal epitope. It is expressed in a number of different cancers including breast, ovarian, melanoma, colon, liver, lung and prostate. In some embodiments of the present invention, SLe$^A$ and SLe$^X$ targets comprise Neu5Gc (referred to herein as GcSLe$^A$ and GcSLe$^X$, respectively).

In some embodiments, therapeutics of the present invention may be directed toward glycolipids and/or epitopes present on glycolipids, including, but not limited to glycosphingolipids. Glycosphingolipids comprise the lipid ceramide linked to a glycan by the ceramide hydroxyl group. On the cell membrane, glycosphingolipids form clusters referred to as "lipid rafts".

In some embodiments, therapeutics of the present invention may be directed toward Globo H. Globo H is a cancer-related glycosphingolipid first identified in breast cancer cells. The glycan portion of Globo H comprises Fucα(1-2)Galβ(1-3)GalNAcβ(1-3)Galα(1-4)Galβ(1-4)Glcβ(1). Although found in a number of normal epithelial tissues, Globo H has been identified in association with many tumor tissues including, but not limited to, small cell lung, breast, prostate, lung, pancreatic, gastric, ovarian and endometrial tumors.

In some embodiments, therapeutics of the present invention may be directed toward gangliosides. Gangliosides are glycosphingolipids comprising sialic acid. According to ganglioside nomenclature, G is used as an abbreviation for ganglioside. This abbreviation is followed by the letters M, D or T referring to the number of sialic acid residues attached (1, 2 or 3 respectively). Finally the numbers 1, 2 or 3 are used to refer to the order of the distance each migrates when analyzed by thin layer chromatography (wherein 3 travels the greatest distance, followed by 2 and then 1). Gangliosides are known to be involved in cancer-related growth and metastasis and are expressed on the cell surface of tumor cells. Gangliosides expressed on tumor cells include, but are not limited to GD2, GD3, GM2 and fucosyl GM1 (also referred to herein as Fuc-GM1). In some embodiments of the present invention, glycan-interacting antibodies are directed toward GD3. GD3 is a regulator of cell growth. In some embodiments, GD3-directed antibodies are used to modulate cell growth and/or angiogenesis. In some embodiments, GD3-directed antibodies are used to modulate cell attachment. In some embodiments of the present invention, glycan interacting antibodies are directed toward GM2. In some embodiments, GM2-directed antibodies are used to modulate cell to cell contact. In some embodiments, ganglioside targets of the present invention comprise Neu5Gc. In some embodiments, such targets may include a GM3 variant comprising Neu5Gc (referred to herein as GcGM3). The glycan component of GcGM3 is Neu5Gcα2-3Galβ1-4Glc. GcGM3 is a known component of tumor cells.

Immune-Related Targets

Many bacterial glycans are known to comprise sialic acid. In some cases, such glycans allow bacteria to evade the innate immune system of hosts, including, but not limited to humans. In one example, bacterial glycans inhibit alternate complement pathway activation through factor H recognition. In another example, bacterial glycans mask underlying residues that may be antigenic. Some bacterial glycans participate in cell signaling events through activation of inhibitory sialic acid binding Ig-like lectins (Siglecs) that dampen the immune response to entities comprising certain sialylated moieties (Chen, X. et al., Advances in the biology and chemistry of sialic acids. ACS Chem. Biol. 2010 Feb. 19; 5(2):163-76). In some embodiments, glycan-interacting antibodies of the present invention may be used to treat immune complications related to bacterial glycans.

Due to the foreign nature of Neu5Gc as described herein, some Neu5Gc glycans are immunogenic resulting in immune related destruction of cells and other entities where these glycans may be expressed. Such autoimmune destruction may be pathogenic. In some embodiments, glycan-interacting antibodies may be used to treat patients suffering from autoimmune disorders related to Neu5Gc glycans.

Anti-Viral Applications

In some embodiments, glycan-interacting antibodies of the invention may target viruses. Viral coat proteins and viral envelopes often comprise glycans, referred to herein as viral surface glycans. Such glycans may be targets of glycan-interacting antibodies. In some embodiments, viral surface glycans comprise sialyl-STn. In a further embodiment, viral surface glycans comprise GcSTn. Viruses that may be targeted by glycan-interacting antibodies include, but are not limited to HIV, influenza, rhinovirus, varicella-zoster, rotavirus, herpes (e.g. types 1 and 2), hepatitis (e.g. types A, B, C, D and E), yellow fever and human papillomavirus.

Other Therapeutic Applications

In some embodiments, glycan-interacting antibodies of the invention may act to alter or control proteolytic events. In some embodiments, glycan-interacting antibodies of the present invention may be internalized into cells prior to binding to targets.

Veterinary Applications

It is contemplated that glycan-interacting antibodies of the invention will find utility in the area of veterinary care including the care and treatment of non-human vertebrates. As described herein, the term "non-human vertebrate" includes all vertebrates with the exception of *Homo sapiens*, including wild and domesticated species such as companion animals and livestock. Non-human vertebrates include mammals, such as alpaca, banteng, bison, camel, cat, cattle, deer, dog, donkey, gayal, goat, guinea pig, horse, llama, mule, pig, rabbit, reindeer, sheep water buffalo, and yak. Livestock includes domesticated animals raised in an agricultural setting to produce materials such as food, labor, and derived products such as fiber and chemicals. Generally, livestock includes all mammals, avians and fish having potential agricultural significance. In particular, four-legged slaughter animals include steers, heifers, cows, calves, bulls, cattle, swine and sheep.

Bioprocessing

In some embodiments of the invention are methods for producing biological products in host cells by contacting the cells with one or more glycan-interacting antibody (such as an antibody or fusion protein) capable of modulating gene expression, or altering levels and/or types of glycans produced wherein such modulation or alteration enhances production of biological products. According to the present invention, bioprocessing methods may be improved by using one or more of the glycan-interacting antibodies of the present invention. They may also be improved by supplementing, replacing or adding one or more glycan-interacting antibodies.

III. Pharmaceutical Compositions

The pharmaceutical compositions described herein can be characterized by one or more of bioavailability, therapeutic window and/or volume of distribution.

Bioavailability

Glycan-interacting antibodies, when formulated into a composition with a delivery/formulation agent or vehicle as described herein, can exhibit an increase in bioavailability as compared to a composition lacking a delivery agent as described herein. As used herein, the term "bioavailability" refers to the systemic availability of a given amount of glycan-interacting antibodies administered to a mammal. Bioavailability can be assessed by measuring the area under the curve (AUC) or the maximum serum or plasma concentration ($C_{max}$) of the unchanged form of a compound following administration of the compound to a mammal. AUC is a determination of the area under the curve plotting the serum or plasma concentration of a compound along the ordinate (Y-axis) against time along the abscissa (X-axis). Generally, the AUC for a particular compound can be calculated using methods known to those of ordinary skill in the art and as described in G. S. Banker, Modern Pharmaceutics, Drugs and the Pharmaceutical Sciences, v. 72, Marcel Dekker, New York, Inc., 1996, herein incorporated by reference.

The $C_{max}$ value is the maximum concentration of the compound achieved in the serum or plasma of a mammal following administration of the compound to the mammal. The $C_{max}$ value of a particular compound can be measured using methods known to those of ordinary skill in the art. The phrases "increasing bioavailability" or "improving the pharmacokinetics," as used herein mean that the systemic availability of a glycan-interacting antibody, measured as AUC, $C_{max}$, or $C_{min}$ in a mammal is greater, when co-administered with a delivery agent as described herein, than when such co-administration does not take place. In some embodiments, the bioavailability of the glycan-interacting antibody can increase by at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%.

Therapeutic Window

Glycan-interacting antibodies, when formulated into a composition with a delivery agent as described herein, can exhibit an increase in the therapeutic window of the administered glycan-interacting antibody composition as compared to the therapeutic window of the administered glycan-interacting antibody composition lacking a delivery agent as described herein. As used herein "therapeutic window" refers to the range of plasma concentrations, or the range of levels of therapeutically active substance at the site of action, with a high probability of eliciting a therapeutic effect. In some embodiments, the therapeutic window of the glycan-interacting antibody when co-administered with a delivery agent as described herein can increase by at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%.

Volume of Distribution

Glycan-interacting antibodies, when formulated into a composition with a delivery agent as described herein, can exhibit an improved volume of distribution ($V_{dist}$), e.g., reduced or targeted, relative to a composition lacking a delivery agent as described herein. The volume of distribution ($V_{dist}$) relates the amount of the drug in the body to the concentration of the drug in the blood or plasma. As used herein, the term "volume of distribution" refers to the fluid volume that would be required to contain the total amount of the drug in the body at the same concentration as in the blood or plasma: $V_{dist}$ equals the amount of drug in the body/concentration of drug in blood or plasma. For example, for a 10 mg dose and a plasma concentration of 10 mg/L, the volume of distribution would be 1 liter. The volume of distribution reflects the extent to which the drug is present in the extravascular tissue. A large volume of distribution reflects the tendency of a compound to bind to the tissue components compared with plasma protein binding. In a clinical setting, $V_{dist}$ can be used to determine a loading dose to achieve a steady state concentration. In some embodiments, the volume of distribution of the glycan-interacting antibody when co-administered with a delivery agent as described herein can decrease at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%.

In some embodiments, glycan-interacting antibodies comprise compositions and/or complexes in combination with one or more pharmaceutically acceptable excipients. Pharmaceutical compositions may optionally comprise one or more additional active substances, e.g. therapeutically and/or prophylactically active substances. General considerations in the formulation and/or manufacture of pharmaceutical agents may be found, for example, in Remington: The Science and Practice of Pharmacy 21$^{st}$ ed., Lippincott Williams & Wilkins, 2005 (incorporated herein by reference).

In some embodiments, compositions are administered to humans, human patients or subjects. For the purposes of the present disclosure, the phrase "active ingredient" generally refers to glycan-interacting antibodies to be delivered as described herein.

Although the descriptions of pharmaceutical compositions provided herein are principally directed to pharmaceutical compositions which are suitable for administration to humans, it will be understood by the skilled artisan that such compositions are generally suitable for administration to any other animal, e.g., to non-human animals, e.g. non-human mammals. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as poultry, chickens, ducks, geese, and/or turkeys.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product into a desired single- or multi-dose unit.

A pharmaceutical composition in accordance with the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the invention will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, or at least 80% (w/w) active ingredient. In one embodiment, active ingredients are antibodies directed toward regulatory elements and/or GPCs.

Formulation

Glycan-interacting antibodies of the invention can be formulated using one or more excipients to: (1) increase stability; (2) increase cell permeability; (3) permit the sustained or delayed release (e.g., from a formulation of the glycan-interacting antibody); and/or (4) alter the biodistribution (e.g., target the glycan-interacting antibody to specific tissues or cell types). In addition to traditional excipients such as any and all solvents, dispersion media, diluents, or other liquid vehicles, dispersion or suspension aids, surface active agents, isotonic agents, thickening or emulsifying agents, preservatives, formulations of the present invention can include, without limitation, liposomes, lipid nanoparticles, polymers, lipoplexes, core-shell nanoparticles, peptides, proteins, cells transfected with the glycan-interacting antibodies (e.g., for transplantation into a subject) and combinations thereof.

Excipients

As used herein, the term "excipient" refers to any substance combined with a compound and/or composition of the invention before use. In some embodiments, excipients are inactive and used primarily as a carrier, diluent or vehicle for a compound and/or composition of the present invention. Various excipients for formulating pharmaceutical compositions and techniques for preparing the composition are known in the art (see Remington: The Science and Practice of Pharmacy, 21$^{st}$ Edition, A. R. Gennaro, Lippincott, Williams & Wilkins, Baltimore, Md., 2006; incorporated herein by reference).

The use of a conventional excipient medium is contemplated within the scope of the present disclosure, except insofar as any conventional excipient medium may be incompatible with a substance or its derivatives, such as by producing any undesirable biological effect or otherwise interacting in a deleterious manner with any other component(s) of the pharmaceutical composition.

Formulations of the pharmaceutical compositions described herein may be prepared by any method known or hereafter developed in the art of pharmacology. In general, such preparatory methods include the step of associating the active ingredient with an excipient and/or one or more other accessory ingredients.

A pharmaceutical composition in accordance with the present disclosure may be prepared, packaged, and/or sold in bulk, as a single unit dose, and/or as a plurality of single unit doses.

Relative amounts of the active ingredient, the pharmaceutically acceptable excipient, and/or any additional ingredients in a pharmaceutical composition in accordance with the present disclosure may vary, depending upon the identity, size, and/or condition of the subject being treated and further depending upon the route by which the composition is to be administered.

In some embodiments, a pharmaceutically acceptable excipient is at least 95%, at least 96%, at least 97%, at least 98%, at least 99%, or 100% pure. In some embodiments, an excipient is approved for use in humans and for veterinary use. In some embodiments, an excipient is approved by United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in pharmaceutical compositions.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (VEEGUM®), sodium lauryl sulfate, quaternary ammonium compounds, etc., and/or combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and VEEGUM® [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [TWEEN®20], polyoxyethylene sorbitan [TWEENn®60], polyoxyethylene sorbitan monooleate [TWEEN®80], sorbitan monopalmitate [SPAN®40], sorbitan monostearate [Span®60], sorbitan tristearate [Span® 65], glyceryl monooleate, sorbitan monooleate [SPAN®80]), polyoxyethylene esters (e.g. polyoxyethylene monostearate [MYRJ®45], polyoxyethylene hydrogenated castor oil, polyethoxylated castor oil, polyoxymethylene stearate, and SOLUTOL®), sucrose fatty acid esters, polyethylene glycol fatty acid esters (e.g. CREMOPHOR®), polyoxyethylene ethers, (e.g. polyoxyethylene lauryl ether [BRIJ®30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, PLUORINC®F 68, POLOXAMER 188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include, but are not limited to, antioxidants, chelating agents, antimicrobial preservatives, antifungal preservatives, alcohol preservatives, acidic preservatives, and/or other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and/or sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and/or trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and/or thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and/or sorbic acid. Exemplary alcohol preservatives include, but are not limited to, ethanol, polyethylene glycol, phenol, phenolic compounds, bisphenol, chlorobutanol, hydroxybenzoate, and/or phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and/or phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, GLYDANT PLUS®, PHENONIP®, methylparaben, GERMALL®115, GERMABEN®II, NEOLONE™, KATHON™, and/or EUXYL®.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and/or combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and/or combinations thereof.

Excipients such as cocoa butter and suppository waxes, coloring agents, coating agents, sweetening, flavoring, and/or perfuming agents can be present in the composition, according to the judgment of the formulator.

Vehicles

Liposomes, Lipoplexes and Lipid Nanoparticles

Glycan-interacting antibodies of the present invention may be formulated using one or more liposomes, lipoplexes, or lipid nanoparticles. In one embodiment, pharmaceutical compositions comprising glycan-interacting antibodies further comprise liposomes. Liposomes are artificially-prepared vesicles which may primarily comprise one or more lipid bilayers and may be used as a delivery vehicle for the administration of nutrients and pharmaceutical formulations. Liposomes can be of different sizes such as, but not limited to, a multilamellar vesicle (MLV) which may be hundreds of nanometers in diameter and may contain a series of concentric bilayers separated by narrow aqueous compartments, a small unicellular vesicle (SUV) which may be smaller than 50 nm in diameter, and a large unilamellar vesicle (LUV) which may be between 50 and 500 nm in diameter. Liposome design may include, but is not limited to, opsonins or ligands in order to improve the attachment of liposomes to unhealthy tissue or to activate events such as, but not limited to, endocytosis. Liposomes may contain a low or a high pH in order to improve the delivery of the pharmaceutical formulations.

The formation of liposomes may depend on the physicochemical characteristics such as, but not limited to, the pharmaceutical formulation entrapped and the liposomal ingredients, the nature of the medium in which the lipid vesicles are dispersed, the effective concentration of the entrapped substance and its potential toxicity, any additional processes involved during the application and/or delivery of the vesicles, the optimization size, polydispersity and the shelf-life of the vesicles for the intended application, and the batch-to-batch reproducibility and possibility of large-scale production of safe and efficient liposomal products.

In one embodiment such formulations may also be constructed or compositions altered such that they passively or actively are directed to different cell types in vivo.

Formulations can also be selectively targeted through expression of different ligands on their surface as exemplified by, but not limited by, folate, transferrin, N-acetylgalactosamine (GalNAc), and antibody targeted approaches.

Liposomes, lipoplexes, or lipid nanoparticles may be used to improve the efficacy of glycan-interacting antibody function as these formulations may be able to increase cell transfection with glycan-interacting antibodies. The liposomes, lipoplexes, or lipid nanoparticles may also be used to increase the stability of glycan-interacting antibodies.

Liposomes that are specifically formulated for antibody cargo are prepared according to techniques known in the art, such as described by Eppstein et al. (Eppstein, D. A. et al., *Biological activity of liposome-encapsulated murine interferon gamma is mediated by a cell membrane receptor*. Proc Natl Acad Sci USA. 1985 June; 82(11):3688-92); Hwang et al. (Hwang, K. J. et al., *Hepatic uptake and degradation of unilamellar sphingomyelin/cholesterol liposomes: a kinetic study*. Proc Natl Acad Sci USA. 1980 July; 77(7):4030-4); U.S. Pat. No. 4,485,045 and U.S. Pat. No. 4,544,545. Production of liposomes with sustained circulation time is also described in U.S. Pat. No. 5,013,556.

Liposomes comprising glycan-interacting antibodies of the present invention may be generated using reverse phase evaporation utilizing lipids such as phosphatidylcholine, cholesterol as well as phosphatidylethanolamine that has been polyethylene glycol-derivatized. Filters with defined pore size are used to extrude liposomes of the desired diameter. In another embodiment, glycan-interacting antibodies of the present invention can be conjugated to the external surface of liposomes by disulfide interchange reaction as is described by Martin et al. (Martin, F. J. et al., *Irreversible coupling of immunoglobulin fragments to preformed vesicles. An improved method for liposome targeting*. J Biol. Chem. 1982 Jan. 10; 257(1):286-8).

Polymers and Nanoparticles

Glycan-interacting antibodies of the invention can be formulated using natural and/or synthetic polymers. Non-limiting examples of polymers which may be used for delivery include, but are not limited to DMRI/DOPE, poloxamer, chitosan, cyclodextrin, and poly(lactic-co-glycolic acid) (PLGA) polymers. These may be biodegradable.

The polymer formulation can permit the sustained or delayed release of glycan-interacting antibodies (e.g., following intramuscular or subcutaneous injection). The altered release profile for glycan-interacting antibodies can result in, for example, release of the glycan-interacting antibodies over an extended period of time. The polymer formulation may also be used to increase the stability of glycan-interacting antibodies.

Polymer formulations can also be selectively targeted through expression of different ligands as exemplified by, but not limited by, folate, transferrin, and N-acetylgalactosamine (GalNAc) (Benoit et al., Biomacromolecules. 2011 12:2708-2714; Rozema et al., Proc Natl Acad Sci USA. 2007 104: 12982-12887; Davis, Mol. Pharm. 2009 6:659-668; Davis, Nature 2010 464:1067-1070; herein incorporated by reference in its entirety).

Glycan-interacting antibodies of the invention can also be formulated as nanoparticles using a combination of polymers, lipids, and/or other biodegradable agents, such as, but not limited to, calcium phosphate. Components may be combined in a core-shell, hybrid, and/or layer-by-layer architecture, to allow for fine-tuning of the nanoparticle so delivery of glycan-interacting antibodies may be enhanced. For glycan-interacting antibodies, systems based on poly(2-(methacryloyloxy)ethyl phosphorylcholine)-block-(2-(diisopropylamino)ethyl methacrylate), (PMPC-PDPA), a pH sensitive diblock copolymer that self-assembles to form nanometer-sized vesicles, also known as polymersomes, at physiological pH may be used. These polymersomes have been shown to successfully deliver relatively high antibody payloads within live cells. (Massignani, et al, Cellular delivery of antibodies: effective targeted subcellular imaging and new therapeutic tool. Nature Proceedings, May, 2010.)

In one embodiment, a PEG-charge-conversional polymer (Pitella et al., Biomaterials. 2011 32:3106-3114) may be used to form a nanoparticle to deliver glycan-interacting antibodies of the present invention. The PEG-charge-conversional polymer may improve upon the PEG-polyanion block copolymers by being cleaved into a polycation at acidic pH, thus enhancing endosomal escape.

The use of core-shell nanoparticles has additionally focused on a high-throughput approach to synthesize cationic cross-linked nanogel cores and various shells (Siegwart et al., Proc Natl Acad Sci USA. 2011 108:12996-13001). The complexation, delivery, and internalization of the polymeric nanoparticles can be precisely controlled by altering the chemical composition in both the core and shell components of the nanoparticle.

In one embodiment, matrices of poly(ethylene-co-vinyl acetate), are used to deliver glycan-interacting antibodies of the invention. Such matrices are described in Nature Biotechnology 10, 1446-1449 (1992).

Antibody Formulations

Glycan-interacting antibodies of the invention may be formulated for intravenous administration or extravascular administration (Daugherty, et al., *Formulation and delivery issues for monoclonal antibody therapeutics*. Adv Drug Deliv Rev. 2006 Aug. 7; 58(5-6):686-706, US patent publication number 2011/0135570, all of which are incorporated herein in their entirety). Extravascular administration routes may include, but are not limited to subcutaneous administration, intraperitoneal administration, intracerebral administration, intraocular administration, intralesional administration, topical administration and intramuscular administration.

Antibody structures may be modified to improve their effectiveness as therapeutics. Improvements may include, but are not limited to improved thermodynamic stability, reduced Fc receptor binding properties and improved folding efficiency. Modifications may include, but are not limited to amino acid substitutions, glycosylation, palmitoylation and protein conjugation.

Glycan-interacting antibodies may be formulated with antioxidants to reduce antibody oxidation. glycan-interacting antibodies may also be formulated with additives to reduce protein aggregation. Such additives may include, but are not limited to albumin, amino acids, sugars, urea, guanidinium chloride, polyalchohols, polymers (such as polyethylene glycol and dextrans), surfactants (including, but not limited to polysorbate 20 and polysorbate 80) or even other antibodies.

Glycan-interacting antibodies of the present invention may be formulated to reduce the impact of water on antibody structure and function. Antibody preparations in such formulations may be may be lyophilized. Formulations subject to lyophilization may include carbohydrates or polyol compounds to protect and stabilize antibody structure. Such compounds include, but are not limited to sucrose, trehalose and mannitol.

Glycan-interacting antibodies of the present invention may be formulated with polymers. In one embodiment, polymer formulations may contain hydrophobic polymers. Such polymers may be microspheres formulated with polylactide-co-glycolide through a solid-in-oil-in-water encapsulation method. Microspheres comprising ethylene-vinyl acetate copolymer are also contemplated for antibody delivery and may be used to extend the time course of antibody release at the site of delivery. In another embodiment, polymers may be aqueous gels. Such gels may, for example, comprise carboxymethylcellulose. Aqueous gels may also comprise hyaluronic acid hydrogel. Antibodies may be covalently linked to such gels through a hydrazone linkage that allows for sustained delivery in tissues, including but not limited to the tissues of the central nervous system.

Peptide and Protein Formulations

Glycan-interacting antibodies of the invention may be formulated with peptides and/or proteins. In one embodiment, peptides such as, but not limited to, cell penetrating peptides and proteins and peptides that enable intracellular delivery may be used to deliver pharmaceutical formulations. A non-limiting example of a cell penetrating peptide which may be used with the pharmaceutical formulations of the present invention includes a cell-penetrating peptide sequence attached to polycations that facilitates delivery to the intracellular space, e.g., HIV-derived TAT peptide, penetratins, transportans, or hCT derived cell-penetrating peptides (see, e.g., Caron et al., Mol. Ther. 3(3):310-8 (2001); Langel, Cell-Penetrating Peptides: Processes and Applications (CRC Press, Boca Raton Fla., 2002); El-Andaloussi et al., Curr. Pharm. Des. 11(28):3597-611 (2003); and Deshayes et al., Cell. Mol. Life. Sci. 62(16):1839-49 (2005), all of which are incorporated herein by reference). The compositions can also be formulated to include a cell penetrating agent, e.g., liposomes, which enhance delivery of the compositions to the intracellular space. Glycan-interacting antibodies of the invention may be complexed to peptides and/or proteins such as, but not limited to, peptides and/or proteins from Aileron Therapeutics (Cambridge, Mass.) and Permeon Biologics (Cambridge, Mass.) in order to enable intracellular delivery (Cronican et al., ACS Chem. Biol. 2010 5:747-752; McNaughton et al., Proc. Natl. Acad. Sci. USA 2009 106: 6111-6116; Sawyer, Chem Biol Drug Des. 2009 73:3-6; Verdine and Hilinski, Methods Enzymol. 2012; 503:3-33; all of which are herein incorporated by reference in their entirety).

In one embodiment, the cell-penetrating polypeptide may comprise a first domain and a second domain. The first domain may comprise a supercharged polypeptide. The second domain may comprise a protein-binding partner. As used herein, "protein-binding partner" includes, but are not limited to, antibodies and functional fragments thereof, scaffold proteins, or peptides. The cell-penetrating polypeptide may further comprise an intracellular binding partner for the protein-binding partner. The cell-penetrating polypeptide may be capable of being secreted from a cell where glycan-interacting antibodies may be introduced.

In formulations of the present invention, peptides or proteins may be incorporated to increase cell transfection by glycan-interacting antibodies or alter the biodistribution of glycan-interacting antibodies (e.g., by targeting specific tissues or cell types).

Cell Formulations

Cell-based formulations of glycan-interacting antibody compositions of the invention may be used to ensure cell transfection (e.g., in the cellular carrier) or alter the biodistribution of the compositions (e.g., by targeting the cell carrier to specific tissues or cell types).

Cell Transfer Methods

A variety of methods are known in the art and are suitable for introduction of nucleic acids or proteins, such as glycan-interacting antibodies, into a cell, including viral and non-viral mediated techniques. Examples of typical non-viral mediated techniques include, but are not limited to, electroporation, calcium phosphate mediated transfer, nucleofection, sonoporation, heat shock, magnetofection, liposome mediated transfer, microinjection, microprojectile mediated transfer (nanoparticles), cationic polymer mediated transfer (DEAE-dextran, polyethylenimine, polyethylene glycol (PEG) and the like) or cell fusion.

The technique of sonoporation, or cellular sonication, is the use of sound (e.g., ultrasonic frequencies) for modifying the permeability of the cell plasma membrane. Sonoporation methods are known to those in the art and are used to deliver nucleic acids in vivo (Yoon and Park, Expert Opin Drug Deliv. 2010 7:321-330; Postema and Gilja, Curr Pharm Biotechnol. 2007 8:355-361; Newman and Bettinger, Gene Ther. 2007 14:465-475; all herein incorporated by reference in their entirety). Sonoporation methods are known in the art and are also taught for example as it relates to bacteria in US Patent Publication 20100196983 and as it relates to other cell types in, for example, US Patent Publication 20100009424, each of which are incorporated herein by reference in their entirety.

Electroporation techniques are also well known in the art and are used to deliver nucleic acids in vivo and clinically (Andre et al., Curr Gene Ther. 2010 10:267-280; Chiarella et al., Curr Gene Ther. 2010 10:281-286; Hojman, Curr Gene Ther. 2010 10:128-138; all herein incorporated by reference in their entirety). In one embodiment, glycan-interacting antibodies may be delivered by electroporation.

Administration and Delivery

The compositions of the present invention may be administered by any of the standard methods or routes known in the art.

Glycan-interacting antibodies of the present invention may be administered by any route which results in a therapeutically effective outcome. These include, but are not limited to enteral, gastroenteral, epidural, oral, transdermal, epidural (peridural), intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection, (into the base of the penis), intravaginal administration, intrauterine, extra-amniotic administration, transdermal (diffusion through the intact skin for systemic distribution), transmucosal (diffusion through a mucous membrane), insufflation (snorting), sublingual, sublabial, enema, eye drops (onto the conjunctiva), or in ear drops. In specific embodiments, compositions may be administered in a way which allows them cross the blood-brain barrier, vascular barrier, or other epithelial barrier. Non-limiting routes of administration for glycan-interacting antibodies of the present invention are described below.

Parenteral and Injectable Administration

Liquid dosage forms for oral and parenteral administration include, but are not limited to, pharmaceutically acceptable emulsions, microemulsions, solutions, suspensions, syrups, and/or elixirs. In addition to active ingredients, liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include adjuvants such as wetting agents, emulsifying and suspending agents, sweetening, flavoring, and/or perfuming agents. In certain embodiments for parenteral administration, compositions are mixed with solubilizing agents such as CREMOPHOR®, alcohols, oils, modified oils, glycols, polysorbates, cyclodextrins, polymers, and/or combinations thereof. In other embodiments, surfactants are included such as hydroxypropylcellulose.

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In order to prolong the effect of an active ingredient, it is often desirable to slow the absorption of the active ingredient from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are prepared by entrapping the drug in liposomes or microemulsions which are compatible with body tissues.

Rectal and Vaginal Administration

Compositions for rectal or vaginal administration are typically suppositories which can be prepared by mixing compositions with suitable non-irritating excipients such as cocoa butter, polyethylene glycol or a suppository wax which are solid at ambient temperature but liquid at body temperature and therefore melt in the rectum or vaginal cavity and release the active ingredient.

Oral Administration

Solid dosage forms for oral administration include capsules, tablets, pills, powders, and granules. In such solid dosage forms, an active ingredient is mixed with at least one inert, pharmaceutically acceptable excipient such as sodium citrate or dicalcium phosphate and/or fillers or extenders (e.g. starches, lactose, sucrose, glucose, mannitol, and silicic acid), binders (e.g. carboxymethylcellulose, alginates, gelatin, polyvinylpyrrolidinone, sucrose, and acacia), humectants (e.g. glycerol), disintegrating agents (e.g. agar, calcium carbonate, potato or tapioca starch, alginic acid, certain silicates, and sodium carbonate), solution retarding agents (e.g. paraffin), absorption accelerators (e.g. quaternary ammonium compounds), wetting agents (e.g. cetyl alcohol and glycerol monostearate), absorbents (e.g. kaolin and bentonite clay), and lubricants (e.g. talc, calcium stearate, magnesium stearate, solid polyethylene glycols, sodium lauryl sulfate), and mixtures thereof. In the case of capsules, tablets and pills, the dosage form may comprise buffering agents.

Topical or Transdermal Administration

As described herein, compositions containing glycan-interacting antibodies of the invention may be formulated for administration topically. The skin may be an ideal target site for delivery as it is readily accessible. Gene expression may be restricted not only to the skin, potentially avoiding non-specific toxicity, but also to specific layers and cell types within the skin.

The site of cutaneous expression of the delivered compositions will depend on the route of nucleic acid delivery. Three routes are commonly considered to deliver glycan-interacting antibodies to the skin. (i) topical application (e.g. for local/regional treatment and/or cosmetic applications); (ii) intradermal injection (e.g. for local/regional treatment and/or cosmetic applications); and (iii) systemic delivery (e.g. for treatment of dermatologic diseases that affect both cutaneous and extracutaneous regions). glycan-interacting antibodies can be delivered to the skin by several different approaches known in the art.

In one embodiment, the invention provides for a variety of dressings (e.g., wound dressings) or bandages (e.g., adhesive bandages) for conveniently and/or effectively carrying out methods of the present invention. Typically dressing or bandages may comprise sufficient amounts of pharmaceutical compositions and/or glycan-interacting antibodies described herein to allow a user to perform multiple treatments of a subject(s).

In one embodiment, the invention provides for compositions comprising glycan-interacting antibodies to be delivered in more than one injection.

Dosage forms for topical and/or transdermal administration of a composition may include ointments, pastes, creams, lotions, gels, powders, solutions, sprays, inhalants and/or patches. Generally, an active ingredient is admixed under sterile conditions with a pharmaceutically acceptable excipient and/or any needed preservatives and/or buffers as may be required. Additionally, the present invention contemplates the use of transdermal patches, which often have the added advantage of providing controlled delivery of a compound to the body. Such dosage forms may be prepared, for example, by dissolving and/or dispensing the compound in the proper medium. Alternatively or additionally, rate may be controlled by either providing a rate controlling membrane and/or by dispersing the compound in a polymer matrix and/or gel.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions.

Topically-administrable formulations may, for example, comprise from about 1% to about 10% (w/w) active ingredient, although the concentration of active ingredient may be as high as the solubility limit of the active ingredient in the solvent. Formulations for topical administration may further comprise one or more of the additional ingredients described herein.

Depot Administration

As described herein, in some embodiments, compositions of the present invention are formulated in depots for extended release. Generally, a specific organ or tissue (a "target tissue") is targeted for administration.

In some aspects of the invention, glycan-interacting antibodies are spatially retained within or proximal to a target tissue. Provided are methods of providing compositions to one or more target tissue of a mammalian subject by contacting the one or more target tissue (comprising one or more target cells) with compositions under conditions such that the compositions, in particular glycan-interacting antibody component(s) of the compositions, are substantially retained in the target tissue, meaning that at least 10, 20, 30, 40, 50, 60, 70, 80, 85, 90, 95, 96, 97, 98, 99, 99.9, 99.99 or greater than 99.99% of the composition is retained in the target tissue. Advantageously, retention is determined by measuring the level of glycan-interacting antibodies present in the compositions entering the target tissues and/or cells. For example, at least 1, 5, 10, 20, 30, 40, 50, 60, 70, 80, 85, 90, 95, 96, 97, 98, 99, 99.9, 99.99 or greater than 99.99% of glycan-interacting antibodies administered to the subject are present intracellularly at a period of time following administration. For example, intramuscular injection to a mammalian subject is performed using an aqueous composition comprising one or more glycan-interacting antibody and a transfection reagent, and retention of the composition is determined by measuring the level of glycan-interacting antibodies present in the muscle cells.

Certain aspects of the invention are directed to methods of providing compositions to target tissues of mammalian subjects, by contacting the target tissues (containing one or more target cells) with compositions under conditions such that the compositions are substantially retained in the target tissue. Compositions contain an effective amount of glycan-interacting antibodies such that the effect of interest is produced in at least one target cell. Compositions generally contain cell penetration agents and a pharmaceutically acceptable carrier, although "naked" glycan-interacting antibodies (such as glycan-interacting antibodies without cell penetration agents or other agents) are also contemplated.

In some embodiments, compositions include a plurality of different glycan-interacting antibodies, where one or more than one of the glycan-interacting antibodies targets a glycan of interest. Optionally, compositions also contain cell penetration agents to assist in the intracellular delivery of compositions. A determination is made of the composition dose required to target glycans of interest in a substantial percentage of cells contained within a predetermined volume of the target tissue (generally, without targeting glycans in tissue adjacent to the predetermined volume, or distally to target tissues). Subsequent to this determination, the determined dose may be introduced directly into the tissue of the mammalian subject.

In one embodiment, the invention provides for glycan-interacting antibodies to be delivered in more than one injection or by split dose injections.

Pulmonary Administration

Pharmaceutical compositions may be prepared, packaged, and/or sold in formulations suitable for pulmonary administration via the buccal cavity. Such formulations may comprise dry particles further comprising active ingredients and having a diameter in the range from about 0.5 nm to about 7 nm or from about 1 nm to about 6 nm. Such compositions are suitably in the form of dry powders for administration using a device comprising a dry powder reservoir to which a stream of propellant may be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nm and at least 95% of the particles by number have a diameter less than 7 nm. Alternatively, at least 95% of the particles by weight have a diameter greater than 1 nm and at least 90% of the particles by number have a diameter less than 6 nm. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50% to 99.9% (w/w) of the composition, and active ingredient may constitute 0.1% to 20% (w/w) of the composition. A propellant may further comprise additional ingredients such as a liquid non-ionic and/or solid anionic surfactant and/or a solid diluent (which may have a particle size of the same order as particles comprising the active ingredient).

Pharmaceutical compositions formulated for pulmonary delivery may provide an active ingredient in the form of droplets of a solution and/or suspension. Such formulations may be prepared, packaged, and/or sold as aqueous and/or dilute alcoholic solutions and/or suspensions, optionally sterile, comprising active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. Droplets provided by this route of administration may have an average diameter in the range from about 0.1 nm to about 200 nm.

Intranasal, Nasal and Buccal Administration

Formulations described herein as being useful for pulmonary delivery are useful for intranasal delivery of a pharmaceutical composition. Another formulation suitable for intranasal administration is a coarse powder comprising the active ingredient and having an average particle from about 0.2 µm to 500 µm. Such a formulation is administered in the manner in which snuff is taken, i.e. by rapid inhalation through the nasal passage from a container of the powder held close to the nose.

Formulations suitable for nasal administration may, for example, comprise from about as little as 0.1% (w/w) and as much as 100% (w/w) of active ingredient, and may comprise one or more of the additional ingredients described herein. A pharmaceutical composition may be prepared, packaged, and/or sold in a formulation suitable for buccal administration. Such formulations may, for example, be in the form of tablets and/or lozenges made using conventional methods, and may, for example, 0.1% to 20% (w/w) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising active ingredient. Such powdered, aerosolized, and/or aerosolized formulations, when dispersed, may have an average particle and/or droplet size in the range from about 0.1 nm to about 200 nm, and may further comprise one or more of any additional ingredients described herein.

Ophthalmic or Otic Administration

A pharmaceutical composition may be prepared, packaged, and/or sold in a formulation suitable for ophthalmic or otic administration. Such formulations may, for example, be in the form of eye or ear drops including, for example, a 0.1/1.0% (w/w) solution and/or suspension of the active ingredient in an aqueous or oily liquid excipient. Such drops may further comprise buffering agents, salts, and/or one or more other of any additional ingredients described herein. Other ophthalmically-administrable formulations which are useful include those which comprise the active ingredient in microcrystalline form and/or in a liposomal preparation. Subretinal inserts may also be used as a form of administration.

Payload Administration

Glycan-interacting antibodies described herein may be used in a number of different scenarios in which delivery of a substance (the "payload") to a biological target is desired, for example delivery of detectable substances for detection of the target, or delivery of a therapeutic or diagnostic agent. Detection methods can include, but are not limited to, both imaging in vitro and in vivo imaging methods, e.g., immunohistochemistry, bioluminescence imaging (BLI), Magnetic Resonance Imaging (MRI), positron emission tomography (PET), electron microscopy, X-ray computed tomography, Raman imaging, optical coherence tomography, absorption imaging, thermal imaging, fluorescence reflectance imaging, fluorescence microscopy, fluorescence molecular tomographic imaging, nuclear magnetic resonance imaging, X-ray imaging, ultrasound imaging, photoacoustic imaging, lab assays, or in any situation where tagging/staining/imaging is required.

Glycan-interacting antibodies can be designed to include both a linker and a payload in any useful orientation. For example, a linker having two ends is used to attach one end to the payload and the other end to the glycan-interacting antibody. The glycan-interacting antibodies of the invention can include more than one payload as well as a cleavable linker. In another example, a drug that may be attached to glycan-interacting antibodies via a linker and may be fluorescently labeled can be used to track the drug in vivo, e.g. intracellularly.

Other examples include, but are not limited to, the use of glycan-interacting antibodies in reversible drug delivery into cells.

Glycan-interacting antibodies described herein can be used in intracellular targeting of a payload, e.g., detectable or therapeutic agents, to specific organelles. In addition, glycan-interacting antibodies described herein may be used to deliver therapeutic agents to cells or tissues, e.g., in living animals. For example, glycan-interacting antibodies described herein may be used to deliver chemotherapeutic agents to kill cancer cells. glycan-interacting antibodies attached to therapeutic agents through linkers can facilitate member permeation allowing the therapeutic agent to travel into a cell to reach an intracellular target.

In some embodiments, the payload may be a therapeutic agent such as a cytotoxin, radioactive ion, chemotherapeutic, or other therapeutic agent. A cytotoxin or cytotoxic agent includes any agent that may be detrimental to cells. Examples include, but are not limited to, taxol, cytochalasin B, gramicidin D, ethidium bromide, emetine, mitomycin, etoposide, teniposide, vincristine, vinblastine, colchicine, doxorubicin, daunorubicin, dihydroxyanthracinedione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020 incorporated herein in its entirety), rachelmycin (CC-1065, see U.S. Pat. Nos. 5,475,092, 5,585,499, and 5,846,545, all of which are incorporated herein by reference), and analogs or homologs thereof. Radioactive ions include, but are not limited to iodine (e.g., iodine 125 or iodine 131), strontium 89, phosphorous, palladium, cesium, iridium, phosphate, cobalt, yttrium 90, samarium 153, and praseodymium. Other therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thiotepa chlorambucil, rachelmycin (CC-1065), melphalan, carmustine (BSNU), lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids).

In some embodiments, the payload may be a detectable agent, such as various organic small molecules, inorganic compounds, nanoparticles, enzymes or enzyme substrates, fluorescent materials, luminescent materials (e.g., luminol), bioluminescent materials (e.g., luciferase, luciferin, and aequorin), chemiluminescent materials, radioactive materials (e.g., $^{18}F_5$ $^{67}Ga$, $^{81m}Kr$, $^{82}Rb$, $^{111}In$, $^{123}I$, $^{133}Xe$, $^{201}Tl$, $^{125}I$, $^{35}S$, $^{14}C$, $^{3}H$ or $^{99m}Tc$ (e.g., as pertechnetate (technetate(VII), $TcO_4^-$)), and contrast agents (e.g., gold (e.g., gold nanoparticles), gadolinium (e.g., chelated Gd), iron oxides (e.g., superparamagnetic iron oxide (SPIO), monocrystalline iron oxide nanoparticles (MIONs), and ultrasmall superparamagnetic iron oxide (USPIO)), manganese chelates (e.g., Mn-DPDP), barium sulfate, iodinated contrast media (iohexyl), microbubbles, or perfluorocarbons). Such optically-detectable labels include for example, without limitation, 4-acetamido-4'-isothiocyanatostilbene-2,2' disulfonic acid; acridine and derivatives (e.g., acridine and acridine isothiocyanate); 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives (e.g., coumarin, 7-amino-4-methylcoumarin (AMC, Coumarin 120), and 7-amino-4-trifluoromethylcoumarin (Coumarin 151)); cyanine dyes; cyanosine; 4',6-diaminidino-2-phenylindole (DAPI); 5' 5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]-naphthalene-1-sulfonyl chloride (DNS, dansylchloride); 4-dimethylaminophenylazophenyl-4'-isothiocyanate (DABITC); eosin and derivatives (e.g., eosin and eosin isothiocyanate); erythrosin and derivatives (e.g., erythrosin B and erythrosin isothiocyanate); ethidium; fluorescein and derivatives (e.g., 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, X-rhodamine-5-(and-6)-isothiocyanate (QFITC or XRITC), and fluorescamine); 2-[2-[3-[[1,3-dihydro-1,1-dimethyl-3-(3-sulfopropyl)-2H-benz[e]indol-2-ylidene]ethylidene]-2-[4-(ethoxycarbonyl)-1-piperazinyl]-1-cyclopenten-1-yl]ethenyl]-1,1-dimethyl-3-(3-sulforpropyl)-1H-benz[e]indolium hydroxide, inner salt, compound with n,n-diethylethanamine(1:1) (IR144); 5-chloro-2-[2-[3-[(5-chloro-3-ethyl-2(3H)-benzothiazol-ylidene)ethylidene]-2-(diphenylamino)-1-cyclopenten-1-yl] ethenyl]-3-ethyl benzothiazolium perchlorate (IR140); Malachite Green isothiocyanate; 4-methylumbelliferone orthocresolphthalein; nitrotyrosine; pararosaniline; Phenol Red; B-phycoerythrin; o-phthaldialdehyde; pyrene and derivatives (e.g., pyrene, pyrene butyrate, and succinimidyl 1-pyrene); butyrate quantum dots; Reactive Red 4 (CIBACRON™ Brilliant Red 3B-A); rhodamine and derivatives (e.g., 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N, N',N letramethyl-6-carboxyrhodamine (TAMRA) tetramethyl rhodamine, and tetramethyl rhodamine isothiocyanate (TRITC)); riboflavin; rosolic acid; terbium chelate derivatives; Cyanine-3 (Cy3); Cyanine-5 (Cy5); cyanine-5.5 (Cy5.5), Cyanine-7 (Cy7); IRD 700; IRD 800; Alexa 647; La Jolta Blue; phthalo cyanine; and naphthalo cyanine.

In some embodiments, the detectable agent may be a non-detectable precursor that becomes detectable upon activation (e.g., fluorogenic tetrazine-fluorophore constructs (e.g., tetrazine-BODIPY FL, tetrazine-Oregon Green 488, or tetrazine-BODIPY TMR-X) or enzyme activatable fluorogenic agents (e.g., PROSENSE® (V isEn Medical))). In vitro assays in which the enzyme labeled compositions can be used include, but are not limited to, enzyme linked immunosorbent assays (ELISAs), immunoprecipitation assays, immunofluorescence, enzyme immunoassays (EIA), radioimmunoassays (RIA), and Western blot analysis.

Combinations

Glycan-interacting antibodies may be used in combination with one or more other therapeutic, prophylactic, diagnostic, or imaging agents. By "in combination with," it is not intended to imply that the agents must be administered at the same time and/or formulated for delivery together, although these methods of delivery are within the scope of the present disclosure. Compositions can be administered concurrently with, prior to, or subsequent to, one or more other desired therapeutics or medical procedures. In general, each agent will be administered at a dose and/or on a time schedule determined for that agent. In some embodiments, the present disclosure encompasses the delivery of pharmaceutical, prophylactic, diagnostic, and/or imaging compositions in combination with agents that may improve their bioavailability, reduce and/or modify their metabolism, inhibit their excretion, and/or modify their distribution within the body.

Dosage

The present disclosure encompasses delivery of glycan-interacting antibodies for any of therapeutic, pharmaceutical, diagnostic or imaging by any appropriate route taking into consideration likely advances in the sciences of drug delivery. Delivery may be naked or formulated.

Naked Delivery

Glycan-interacting antibodies of the present invention may be delivered to cells, tissues, organs or organisms in naked form. As used herein in, the term "naked" refers to glycan-interacting antibodies delivered free from agents or modifications which promote transfection or permeability. Naked glycan-interacting antibodies may be delivered to cells, tissues, organs and/or organisms using routes of administration known in the art and described herein. Naked delivery may include formulation in a simple buffer such as saline or PBS.

Formulated Delivery

Glycan-interacting antibodies of the present invention may be formulated, using methods described herein. Formulations may comprise glycan-interacting antibodies which may be modified and/or unmodified. Formulations may further include, but are not limited to, cell penetration agents, pharmaceutically acceptable carriers, delivery agents, bioerodible or biocompatible polymers, solvents, and sustained-release delivery depots. Formulated glycan-interacting antibodies may be delivered to cells using routes of administration known in the art and described herein.

Compositions may also be formulated for direct delivery to organs or tissues in any of several ways in the art including, but not limited to, direct soaking or bathing, via a catheter, by gels, powder, ointments, creams, gels, lotions, and/or drops, by using substrates such as fabric or biodegradable materials coated or impregnated with compositions, and the like.

Dosing

The present invention provides methods comprising administering one or more glycan-interacting antibodies in accordance with the invention to a subject in need thereof. Nucleic acids encoding glycan-interacting antibodies, proteins or complexes comprising glycan-interacting antibodies, or pharmaceutical, imaging, diagnostic, or prophylactic compositions thereof, may be administered to a subject using any amount and any route of administration effective for preventing, treating, diagnosing, or imaging a disease, disorder, and/or condition. The exact amount required will vary from subject to subject, depending on the species, age, and general condition of the subject, the severity of the disease, the particular composition, its mode of administration, its mode of activity, and the like. Compositions in accordance with the invention are typically formulated in dosage unit form for ease of administration and uniformity of dosage. It will be understood, however, that the total daily usage of the compositions of the present invention will be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In certain embodiments, compositions in accordance with the present invention may be administered at dosage levels sufficient to deliver from about 0.0001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic, diagnostic, prophylactic, or imaging effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

According to the present invention, glycan-interacting antibodies may be administered in split-dose regimens. As used herein, a "split dose" is the division of single unit dose or total daily dose into two or more doses, e.g., two or more administrations of the single unit dose. As used herein, a "single unit dose" is a dose of any therapeutic administered in one dose/at one time/single route/single point of contact, i.e., single administration event. As used herein, a "total daily dose" is an amount given or prescribed in a 24 hr period. It may be administered as a single unit dose. In one embodiment, glycan-interacting antibodies of the present invention are administered to a subject in split doses. Glycan-interacting antibodies may be formulated in buffer only or in a formulation described herein. Pharmaceutical compositions comprising glycan-interacting antibodies as described herein may be formulated into a dosage form described herein, such as a topical, intranasal, intratracheal, or injectable (e.g., intravenous, intraocular, intravitreal, intramuscular, intracardiac, intraperitoneal or subcutaneous). General considerations in the formulation and/or manufacture of pharmaceutical agents may be found, for example, in Remington: The Science and Practice of Pharmacy 21$^{st}$ ed., Lippincott Williams & Wilkins, 2005 (incorporated herein by reference).

Coatings or Shells

Solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

IV. Kits and Devices

Kits

Any of the compositions described herein may be comprised in a kit. In a non-limiting example, reagents for generating glycan-interacting antibodies, including antigen molecules are included in a kit. The kit may further include reagents or instructions for creating or synthesizing glycan-interacting antibodies. It may also include one or more buffers. Other kits of the invention may include components for making glycan-interacting antibody protein or nucleic acid arrays or libraries and thus, may include, for example, a solid support.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit (labeling reagent and label may be packaged together), the kit also will generally contain a second, third or other additional container into which the additional components may be separately placed. The kits may also comprise a second container means for containing a sterile, pharmaceutically acceptable buffer and/or other diluent. However, various combinations of components may be comprised in a vial. The kits of the present invention also will typically include a means for containing the glycan-interacting antibodies, e.g., proteins, nucleic acids, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. However, the components of the kit may be provided as dried powder(s). When reagents and/or components are provided as a dry powder, the powder can be reconstituted by the addition of a suitable solvent. It is envisioned that the solvent may also be provided in another container means. In some embodiments, labeling dyes are provided as a dried powder. It is contemplated that 10, 20, 30, 40, 50, 60, 70, 80, 90, 100, 120, 120, 130, 140, 150, 160, 170, 180, 190, 200, 300, 400, 500, 600, 700, 800, 900, 1000 micrograms or at least 1000 micrograms or at most 10 g of dried dye are provided in kits of the invention. The dye may then be resuspended in any suitable solvent, such as DMSO.

A kit may include instructions for employing the kit components as well the use of any other reagent not included in the kit. Instructions may include variations that can be implemented.

Devices

Any of the compositions described herein may be combined with, coated onto or embedded in a device. Devices include, but are not limited to, dental implants, stents, bone replacements, artificial joints, valves, pacemakers or other implantable therapeutic devices.

V. Equivalents and Scope

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context.

The invention includes embodiments in which exactly one member of the group is present in, employed in, or otherwise relevant to a given product or process. The invention includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

EXAMPLES

Example 1

Monoclonal Anti-GcSTn, Methods for Generation and Myeloma Cell Production

GcSTn-containing porcine submaxillary mucin (PSM) is extracted from porcine submaxillary glands, and injected into Cmah$^{-/-}$ mouse. Wild type mice possess a functional Cmah gene, and biosynthesize high level of endogenous Neu5Gc. Therefore, without wishing to be held by theory, using Cmah$^{-/-}$ mouse increases the immune response against GcSTn. The mouse serum is evaluated for the production of anti-GcSTn antibodies using EIA (a modified ELISA that specifically identifies Neu5Gc and other sialic acids). The serum of the mice that are positive for the expression of GcSTn are further evaluated for anti-GcSTn specificity of the antibodies produced by use of our unique glycan microarray, which includes two different forms of STn, GcSTn and AcSTn. The mice are selected for establishment of anti-GcSTn-producing hybridoma, following standard procedures.

Development of Cmah–/– Mouse Myeloma, and Establishment of Hybridoma

A Cmah$^{-/-}$ mouse myeloma fusion partner for the production of a non-Neu5Gc producing hybridoma is provided. Cmah$^{-/-}$ myeloma cell line(s) are useful not only in the production of anti-GcSTn antibody, but any other antibodies intended for human use, resulting in products that will not contain the non-human immunogenic glycan, Neu5Gc. Further, other genes can be knocked out in the background of Cmah$^{-/-}$ NS0 cells. An example is the removal of the alpha1, 3-galactosyltransferase gene which results in an enzyme critical for the formation of an epitope highly-immunogenic to humans (alpha-gal), eliminating alpha-gal by the same method.

A monoclonal antibody directed against GcSTn can be used as a screening tool for a large number of cancer samples to determine the presence and evaluate the potential of anti-GcSTn antibodies as a biomarker in early cancer diagnosis. Such xeno-autoantigen (GcSTn), and antibodies (anti-GcSTn), can be used as therapeutics for human carcinomas. Prior to therapy, the binding of anti-GcSTn to malignant tissues can be assessed by antibody staining of cancer biopsy samples, or by in vivo imaging.

Cmah–/– Mice for Immunization

Neu5Gc-deficient Cmah$^{-/-}$ mice (as described in application PCT/US2006/022282, herein incorporated by reference) are used for immunization. While not wishing to be held by theory, the lack of endogenous Neu5Gc-containing glycans in such mice combined with an antigen rich in GcSTn [porcine submaxillary mucins, (Brinkman-Van der Linden, E. C. et al., New aspects of siglec binding specificities, including the significance of fucosylation and of the sialyl-Tn epitope. Sialic acid-binding immunoglobulin superfamily lectins. J Biol. Chem. 2000 Mar. 24; 275(12):8625-32)] generates a strong anti-GcSTn immune response.

Cmah Gene In Vitro Knockout from Murine Myeloma

Provide herein is a murine myeloma fusion partner lacking the expression of Neu5Gc. In an embodiment, this is accomplished by using Zinc Finger Nuclease (ZFN) technology to knock out the Cmah gene.

Zinc Finger Nucleases are artificial restriction enzymes generated by fusing a zinc finger DNA-binding domain to a DNA-cleavage domain (Kim, Y. G. et al., Hybrid restriction enzymes: zinc finger fusions to Fok I cleavage domain. Proc Natl Acad Sci USA. 1996 Feb. 6; 93(3):1156-60). The Zinc finger domains can be engineered to target desired DNA sequences, and so directs the ZFN to a specific locus in the genome. ZFN introduces a recombinogenic double-strand break into the targeted gene, which stimulates the cell's natural DNA-repair processes, non-homologous end joining (NHEJ). Due to the imperfect nature of NHEJ, a percentage of double-strand breaks within the ZFN-treated cellular population will be mis-repaired by the addition and/or deletion of nucleotides. Modified cell lines can be created by using ZFN with targeted gene deletions, gene insertions, etc (Cathomen, T. et al., Zinc-finger nucleases: the next generation emerges. Mol. Ther. 2008 July; 16(7):1200-7). This technology has been successfully used to engineer a wide variety of different gene targets, in a wide range of different species (Porteus, M. H. et al., Chimeric nucleases stimulate gene targeting in human cells. Science. 2003 May 2; 300(5620):763; Bibikova, M. et al., Enhancing gene targeting with designed zinc finger nucleases. Science. 2003 May 2; 300(5620):764; Carroll, D., Progress and prospects: zinc-finger nucleases as gene therapy agents. Gene Ther. 2008 November; 15(22):1463-8; Doyon, Y. et al., Heritable targeted gene disruption in zebrafish using designed zinc-finger nucleases. Nat. Biotechnol. 2008 June; 26(6):702-8; Geurts, A. M. et al., Knockout rats via embryo microinjection of zinc-finger nucleases. Science. 2009 Jul. 24; 325(5939):433; Meng, X. et al., Targeted gene inactivation in zebrafish using engineered zinc-finger nucleases. Nat. Biotechnol. 2008 June; 26(6):695-701; Urnov, F. D. et al., Highly efficient endogenous human gene correction using designed zinc-finger nucleases. Nature. 2005 Jun. 2; 435 (7042):646-51; Townsend, J. A. et al., High-frequency modification of plant genes using engineered zinc-finger nucleases. Nature. 2009 May 21; 459(7245):442-5). ZFNs have also been applied to targeting glycosylation pathways, such as O-glycan elongation (Steentoft, C. et al., Mining the O-glycoproteome using zinc-finger nuclease-glycoengineered SimpleCell lines. Nat. Methods. 2011 Oct. 9; 8(11): 977-82), and fucosylation (Malphettes, L. et al., Highly efficient deletion of FUT8 in CHO cell lines using zinc-finger nucleases yields cells that produce completely nonfucosylated antibodies. Biotechnol Bioeng. 2010 Aug. 1; 106(5): 774-83) providing evidence that the production of a $Cmah^{-/-}$ cell line is highly likely. With this approach, permanent and heritable knockout in any cell line where transfection is possible can be achieved much more rapidly and efficiently than with traditional knockout methods. Sigma Aldrich has been identified as capable of producing and supplying ZFNs to target any genes in human and mouse genome, and the ZFNs are designed to a sequence within the first two-thirds of the open reading frame ensuring that the gene disruption will lead to a knockout. This can provide a rapid, highly specific, and cost-effective method to generate a $Cmah^{-/-}$ NS0 cell line, which can then be used as a fusion partner for production of mouse monoclonal antibodies against any Neu5Gc-containing epitopes.

In addition to being a fusion partner, the NS0 cell can be used for the production of therapeutic monoclonal antibodies. A key issue regarding the use of therapeutic antibodies in patients remains the potential presence of immunogenic Neu5Gc-containing glycans, as antibodies are themselves glycoproteins. The presence of anti-Neu5Gc xeno-autoantibodies in all humans tested so far (Varki, N. M. et al., Biomedical differences between human and nonhuman hominids: potential roles for uniquely human aspects of sialic acid biology. Annu Rev Pathol. 2011. 6: 365-393; Padler-Karavani, V. et al., Diversity in specificity, abundance, and composition of anti-Neu5Gc antibodies in normal humans: potential implications for disease. Glycobiology. 2008. 18: 818-830) might therefore result in increased immunogenicity and/or decreased efficacy of the Neu5Gc-containing biotherapeutic antibody. It has been previously shown that upon contact with Neu5Gc-containing biotherapeutics, an anti-Neu5Gc immune response is induced in $Cmah^{-/-}$ mice, which have the human-like Neu5Gc-deficiency. Notably, the presence of anti-Neu5Gc antibodies also increased the clearance of a Neu5Gc-presenting biotherapeutic glycoprotein (Ghaderi, D. et al., Implications of the presence of N-glycolylneuraminic acid in recombinant therapeutic glycoproteins. Nat. Biotechnol. 2010. 28: 863-867). To overcome this drawback, in the present invention $Cmah^{-/-}$ NS0 cells are cultured under Neu5Gc-free conditions to produce anti-GcSTn antibody. Fusion of splenocytes from immunized $Cmah^{-/-}$ mice with $Cmah^{-/-}$ hybridoma cells yield a production platform for Neu5Gc-free biotherapeutic antibodies, which possess reduced immunogenicity and increased efficacy in humans.

Glycan Array for Antibody Specificity Evaluation

In one embodiment, the present invention provides an antibody that is GcSTn-specific. The antibody has little cross-reactivity to Neu5Ac-STn or Tn. The antibody can bind GcSTn but has reduced affinity for AcSTn.

A glycan array has more than 70 chemically-synthesized glycans, most of which are presented as Neu5Ac and Neu5Gc-containing glycan pairs. Some examples of glycan probes include: Neu5Ac-α-2-6-GalNAc (AcSTn); Neu5Gc-α-2-6-GalNAc (GcSTn); Neu-5,9Ac2-α-2,6-GalNAc; Neu9Ac5Gc-α-2,6-GalNAc, and GalNAc (Tn). The antibody binding specificity to AcSTn vs. GcSTn can be determined using the array or other methods of determining specificity known in the art. In addition, the binding profile to O-acetylated STn can be determined—as the loss of O-acetylation on STn is relevant to its cancer-associated expression, and correlates with increased STn recognition by antibodies (Ogata, S. et al., Tumor-associated sialylated antigens are constitutively expressed in normal human colonic mucosa. Cancer Res. 1995 May 1; 55(9):1869-74) and furthermore, determine STn vs. Tn recognition.

The specificity of an antibody was determined by glycan array and the results are shown in FIG. 1. This anti-STn antibody (clone STn 219, Abcam, Cambridge, Mass.) is a mouse monoclonal antibody that was produced using OSM (ovine submaxillary mucin) as the immunogen. The binding epitope is purported to be Neu5Ac-α-GalNAc (manufacturer's datasheet). STn 219 was tested on our unique glycan array. The results showed that STn 219 recognized multiple STn-related oligosaccharides including Neu5Ac-α-2-6-GalNAc (AcSTn) probe #5; Neu5Gc-α-2-6-GalNAc (GcSTn) probe #6; Neu-5,9Ac2-α-2,6-GalNAc probe #23; Neu9Ac5Gc-α-2,6-GalNAc probe#24, and GalNAc probe #47 (Tn). Furthermore, there was no binding to the remaining glycans on the array. Probes #25 and #26 (Neu5Ac-α-2,3-Gal and Neu5Gc-α-2,3-Gal, respectively) are shown as an example of non-binding controls. This particular antibody is cross-reactive with GalNAc, and does not detect the Neu5Ac/Neu5Gc difference.

Preparation of GcSTn-Containing Immunogen, and Immunization of Cmah−/− Mice

In an embodiment, porcine submaxillary mucin (PSM) can be used to prevent a pan-anti-Neu5Gc response and induce a more specific immune response against GcSTn. PSM is rich in Neu5Gc-containing mucin-type, glycoproteins that are decorated with GcSTn, the immunogen of interest. Among the currently known sources of high Neu5Gc content is red meat; especially submaxillary glands were previously described as a rich source of Neu5Gc due to the high expression of the CMAH enzyme, which catalyzes the reaction to produce the Neu5Gc precursor, CMP-Neu5Ac.

Preparation of Immunogen

Porcine submaxillary glands (Cat#: 59443-2; Pel-Freez Biologicals, Rogers, Ark.) are homogenized in 5 volumes of water. Homogenates are centrifuged, and the supernatant then filtered through glass wool. This mucin is precipitated by gradual acidification (to pH 3.5) at 4° C. and mixed overnight at 4° C., then left to settle. The supernatant is removed by siphoning and the precipitated mucin is centrifuged, washed with water, and centrifuged again. Mucin pellets are adjusted to pH 8.0 and dialyzed using a 10,000 MWCO CE membrane (Spectrum Labs, Rancho Dominguez, Calif.) against 20 volumes of water, with at least 5 volume changes. The purified PSM are lyophilized for stable, long-term storage and its Neu5Gc content is characterized by DMB-HPLC. Sialic acids in PSM (or other biological samples) are released by mild acid treatment (2M acetic acid, 80° C., 3 Hours), purified by Microcon10 filter tubes and measured by high performance liquid chromatography (HPLC) on a Ultima3000 HPLC (Dionex) by tagging sialic acids with the fluorophor, 1,2-diamino-4,5-methylene-dioxybenzene (DMB, Sigma) using previously described methods (Diaz, S. L. et al., Sensitive and specific detection of the non-human sialic Acid N-glycolylneuraminic acid in human tissues and biotherapeutic products. PLoS One. 2009. 4: e4241). HPLC runs are performed at 0.9 mL/min in 85% $H_2O$, 7% MeOH, 8% $CH_3CN$. Fluorescent signals are excited at 373 nm and acquired at 448 nm.

Immunization of Mice with GcSTn and Mouse Serum Screening for Anti-GcSTn $Cmah^{-/-}$ mice are bled and then immunized with 100 μg PSM in Complete Freund's adjuvant (CFA) at day 0, and with 100 μg PSM in Incomplete Freund's adjuvant (IFA) at days 14, 28, and 42, generating IgG antibodies that specifically recognize GcSTn. To determine the titer of anti-GcSTn antibodies, mouse sera is collected at day 36 and analyzed by a specific enzyme immunoassay (EIA). Bovine submaxillary mucin (BSM) is used as the target in the EIA to specifically detect anti-GcSTn antibodies, which is comparable to PSM with two differences: the protein backbone of porcine and bovine submaxillary mucin is not identical and BSM is known to have high levels of 9-O-acetylated sialic acids. To establish a target that does not contain the same protein backbone as PSM but that does contain the same desired glycan epitope GcSTn, 9-O-acetylation of BSM is removed with mild base treatment (0.1 M NaOH) before immobilization on EIA plate.

Where the anti-GcSTn titer in the mouse sera is sufficient, the final boost is i.v. injected PSM at day 56, 3 days prior the harvest of the spleen, otherwise, where the titer is still too low, immunization of the Cmah$^{-/-}$ mice with 100 μg PSM in Incomplete Freund's adjuvant (IFA) is repeated in 14-day intervals until the titer is satisfactory. The final boost is i.v. injected PSM 3 days prior to the harvest of the spleen.

Development of Cmah$^{-/-}$ Mouse Myeloma

NS0 cells are cultured in EX-CELL NS0 media (Sigma Aldrich, St. Louis, Mo.), free of serum and other animal components including proteins. The absence of Neu5Gc in the media is reconfirmed by western blot. Specific ZFNs targeting the mouse Cmah gene are transfected in the form of a plasmid or mRNA, via lipofection. After 7-10 days of cell expansion, the clone selection for Cmah deletion is performed. Transformed NS0 cells are harvested, washed, and stained with the primary anti-Neu5Gc antibody, followed by secondary Cy3-labeled anti-chicken IgY antibody incubation, and interrogated by flow cytometry. NS0 cells with an intact Cmah gene bind to anti-Neu5Gc antibody (Kilgore, B. R. et al., Comparability and monitoring immunogenic N-linked oligosaccharides from recombinant monoclonal antibodies from two different cell lines using HPLC with fluorescence detection and mass spectrometry. Methods Mol. Biol. 2008; 446:333-46), while those with the gene being successfully deleted show reduced staining. The cells are sorted, cultured one cell per well in 96-well plates, and expanded. The selected cells are interrogated once more by flow cytometry after expansion. The genotype is confirmed by genomic DNA extraction and sequencing. After the genotype is confirmed, the Cmah knock-out NS0 subclones are cultured and cryopreserved.

The resulting Cmah$^{-/-}$ hybridoma is useful not only in the production of this particular antibody, but any other antibodies intended for human use, resulting in products that do not contain the non-human immunogenic glycan, Neu5Gc. Other genes can be knocked out in the background of Cmah$^{-/-}$ NS0 cells. For example, the alpha1,3-galactosyltransferase gene, which encodes an enzyme critical for the formation of an epitope highly-immunogenic to humans (Chung, C. H. et al., Cetuximab-induced anaphylaxis and IgE specific for galactose-alpha-1,3-galactose. N Engl J. Med. 2008 Mar. 13; 358 (11):1109-17), can be knocked out in the background of Cmah$^{-/-}$ NS0 cells.

Alternate strategies to ZFNs mutagenesis can be used. Alternate transfection methods known in the art can be used. Other mouse myeloma cell lines may be used to replace the NS0 cell line. For example, Sp2/0-Ag14 can be an alternative cell line for hybridoma development. Transcription Activator-Like Effector Nucleases (TALENs)—induced gene editing provides an alternative gene knock out method. TALENs are artificial restriction enzymes generated by fusing the TAL effector DNA binding domain to a DNA cleavage domain. Similar to ZFNs, TALENs induce double-strand breaks at desired loci that can be repaired by error-prone NHEJ to yield insertions/deletions at the break sites (Wood, A. J. et al., Targeted genome editing across species using ZFNs and TALENs. Science. 2011 Jul. 15; 333(6040):307). Cellectis Bioresearch (Cambridge, Mass.) provides the service of TALEN design and plasmid construction.

Establishment of Hybridoma

The hybridoma fusion is performed with the NS0 cells genetically modified as Cmah$^{-/-}$. Cmah$^{-/-}$ NS0 cells and the splenocytes are mixed at a ratio of 1:2. Fifty percent PEG (Polyethylene glycol 1500) is added to induce fusion. Cells are cultured in HAT selection media (hypoxanthine, aminopterin, and thymidine), and distributed in 96-well plates. Hybridoma growth and tumor cell death are checked regularly using an inverted microscope. After 10-14 d, the hybridomas are fed with HT medium (hypoxanthine, and thymidine) at which point hybridoma selection is performed by selecting isolated colonies and culturing them.

Clone Selection

Cells are screened for desired antibody secretion after about 15 days, or when some wells just begin to turn yellowish. All wells are screened with EIA as described earlier. Candidate hybridomas are transferred to 24-well plates and allowed to expand. The specificity of the antibody towards Neu5Gc-STn is tested on microarray, in which the pair of GcSTn and AcSTn probes is contained. The hybridomas producing antibodies against GcSTn, but not AcSTn, nor both, are selected and tested with flow cytometry, using Jurkat cells fed with Neu5Ac or Neu5Gc (Padler-Karavani, V. et al., Human xeno-autoantibodies against a non-human sialic acid serve as novel serum biomarkers and immunotherapeutics in cancer. Cancer Res. 2011 May 1; 71(9):3352-63). Selected cells then undergo limiting dilution. The same assays used in the initial identification of the master well are performed. The desired cells are expanded and frozen as for the primary hybridomas. Positive hybridoma clones are recloned (by seeding at 0.3 cells/well). The resulting hybridoma is monoclonal, and stable as a cell line.

Alternative methods to clone the hybridomas include such as those provided by kits from STEMCELL Technologies (Vancouver, BC, Canada), e.g. ClonaCell™-HY kit, containing methylcellulose-based semi-solid medium and other media and reagents, to support the selection and growth of hybridoma clones. However, the media in this kit contain FCS, which provides an exogenous source for Neu5Gc incorporation. Though the machinery for endogenous Neu5Gc synthesis is destroyed in Cmah$^{-/-}$ hybridoma, Neu5Gc incorporated from the culture media may also pose a problem (Bardor, M. et al., Mechanism of uptake and incorporation of the non-human sialic acid N-glycolylneuraminic acid into human cells. J Biol. Chem. 2005. 280: 4228-4237). In this case, one can supplement Neu5Ac to the culture media to eliminate Neu5Gc incorporation by metabolism competition (Ghaderi, D. et al., Implications of the presence of N-glycolylneuraminic acid in recombinant therapeutic glycoproteins. Nat. Biotechnol. 2010. 28: 863-867).

In addition to the potential cytotoxic properties of the inventive antibodies, tumor killing can be boosted by the conjugation of a toxin to the anti-GcSTn antibody. The antibody can be humanized using standard methods in the art. The humanized antibody can be characterized for its binding specificity, complement-dependent cytotoxicity, and antibody-dependent cellular-mediated cytotoxicity, etc.

Example 2

Porcine Submaxillary (PSM) Mucus Production 150 cryoground submaxillary glands (Pelfreeze Biologicals, Rogers, Ark.) were purchased and kept frozen at −20° C. until use. 700 g of cryoground glands were weighed and added to a 4 L beaker with 3.5 L of purified water. The solution was stirred at 4° C. for 6-8 hours using a magnetic stir bar. Stirring was then halted and the solution was allowed to settle overnight at 4° C. A funnel (10 inch diameter) was prepared by fluffing about 2 inches of glass wool and softly plugging the bottom of the funnel. About 4 inches of glass wool was then fluffed and layed on top of the plug. Next, a mesh (Home Depot, Atlanta, Ga.) with 0.25 mm pores was placed on top. Supernatant from the submaxillary gland solution was collected at 4° C. by slowly filtering through the padded funnel. Solid waste caught in the filter was discarded. The filtered supernatant was acidified to pH 3.5 by slowly adding 40-50 ml of 1 M HCl while stirring. The solution was stirred at 4° C. for 8 hours and then allowed to settle overnight at 4° C. The settled material, containing mucins, was collected by siphoning off the supernatant. Mucins were prepared by spinning at 400×g for 15 min at 4° C. in a Sorvall centrifuge (Thermo Fisher Scientific, Waltham, Mass.). The supernatant was discarded and the pellet was resuspended in purified water and spun again at 400×g for 15 min at 4° C. in a Sorvall centrifuge. The supernatant was again discarded and the pellet was collected by resuspension in a minimal volume of purified water. The pH of the pellet solution was adjusted to pH 8.0 using 1.5 M NaOH before stirring the solution overnight at 4° C. to homogenize the solution. The mucin solution was then dialyzed against distilled water using 140 mm wide dialysis tubing. 0.2 L batches were dialyzed in a large bucket with 5 changes of water. A freezing bath was then prepared by mixing ethanol with dry ice in a styrofoam box. Clean lyophilizer bottles were placed into the freezing bath and dialyzed mucin solution was poured slowly into each bottle to allow for freezing. Lyophilizer bottles containing frozen mucin solution were then transferred to a lyophilizer and dried for about 7 days. Bottle weights were recorded and bottles were stored at −20° C. in vacuum-sealed bags until use.

Example 3

Mouse Immunization

Mouse immunization was carried out by Explora Biolabs (San Diego, Calif.). 16 male Cmah −/− mice, ages 8-12 weeks were obtained and allowed to acclimate at least 3 days. Mice were given ad libitum access to standard diet (2920X.10, Global 18% Protein Rodent Diet from Harlan, San Diego, Calif.) and acidified water (pH 2.7-3.0) throughout the study period. The 16 mice were divided into two groups (Group 1 and Group 2, 8 mice/group), randomized based on body weight. During the study, animals were monitored for health and weighed twice per week (for a total of 8 time points).

Group 1 mice were vaccinated by subcutaneous injections of 100 μg of porcine submaxillary mucin (PSM) with Titermax adjuvant (CytRx Corporation, Los Angeles, Calif.). Each vaccination comprised 50 μl injections at 4 sites (200 μl total volume) located on each animal around armpits and inguinal regions. Animals were vaccinated on days 0, 7, 14, 21 and 25. Blood was collected from Group 1 animals prior to immunization on days 0, 21 and 25. Blood collected on day 0 included approximately 0.2 ml of whole blood taken via facial vein bleed. Blood was collected into serum separator tubes and kept at room temperature for at least 30 minutes to allow clotting. The blood was processed to serum and stored at −80° C. until use.

Group 2 mice were vaccinated by subcutaneous injection of 100 μg of PSM with either Complete Freund's adjuvant (CFA), Incomplete Freund's adjuvant (IFA) or without adjuvant. Each vaccination comprised 50 μl injections at 4 sites (200 μl total volume) located on each animal around armpits and inguinal regions. Animals were vaccinated on days 0, 14, 28, 42 and 56. CFA was included with the vaccination on day 0 while IFA was included with the vaccinations on days 14, 28 and 42. No adjuvant was included with the vaccination on day 56. Blood was collected from Group 2 animals prior to immunization on days 0, 42 and 56. Blood collected on day 0 included approximately 0.2 ml of whole blood taken via facial vein bleed. Blood was collected into serum separator tubes and kept at room temperature for at least 30 minutes to allow clotting. The blood was processed to serum and stored at −80° C. until use.

At the termination of the study, mice were euthanized and blood and tissue were harvested for analysis. Group 1 mice were euthanized on day 28 of the study, while Group 2 mice were euthanized on day 59 of the study. Terminal blood samples were collected via cardiac puncture into serum separator tubes and kept at room temperature for at least 30 minutes to allow clotting. The blood was processed to serum and stored at −80° C. until use. Spleens were harvested and flash frozen in liquid nitrogen before storage at −80° C. until use.

Example 4

Analysis of Group 1 Mouse Samples by Glycan Microarray

Glycan microarray slides were scanned prior to and after ethanolamine blocking to look for changes in background signal. Ethanolamine blocking was carried out by first preparing a blocking solution comprising 0.1 M Tris, 0.05 M ethanolamine and a pH of 9.0. The solution, as well as a 1.5 L beaker of double-distilled water (for washes) were heated to 50° C. The slides were arranged in the slide holder and quickly submerged in staining tubs with blocking buffer at 50° C. (slides were shaken lightly to dislodge bubbles from the slides). Staining tubs were placed on a shaker for 60 minutes. Washing tubs were prepared with pre-warmed (50° C.) double-distilled water. Slides were rinsed by submersion in the first tub of water with gentle shaking and then transferred to the second tub where they were placed on a shaker for 10 minutes or more. 2 additional washing tubs were prepared and slides were transferred to the first and then to the second tub for 1 minute. Slides were then removed and dried by centrifugation at 200×g for 5 min and stored in an airtight bag in the dark until use.

For slide development, an appropriate volume of blocking and washing solutions were prepared. Blocking solution was prepared by combining phosphate buffered saline (PBS) with ovalbumin (at 1% of final volume). Washing solution 1 was PBST [PBS (pH 7.3) with 0.1% Tween-20]. Washing solution 2 was PBS (pH 7.3). Washing solution 3 was double-distilled water.

Next, each slide was placed into the ArrayIt hybridization tool (Arrayit corporation, Sunnyvale, Calif.). Each microarray well was filled with 200 μl of blocking solution and incubated for 1 hour in a humid chamber at room temperature with gentle shaking before dumping out the solution. Group 1 mouse (as described in example 3) serum samples were prepared in blocking solution at a ratio of 1:250 and added to individual microarray wells (200 μl/well). Wells were incubated for 1 hour at room temperature in a humid chamber with shaking 200 μl of PBS was next added to each well, slides were shaken for 1 min and then emptied. Slides were then immediately washed with washing solution 1, quickly emptied and filled again with washing solution 1 before shaking for 10 minutes at room temperature. Washing solution 1 was discarded from the wells, wells were refilled with washing solution 2 and then emptied. Remaining washing solution in wells was aspirated before proceeding to the next step.

For detection of bound antibodies, 200 μl of secondary antibody solution [Cy3-conjugated anti-mouse IgG antibody (Jackson Laboratories, Bar Harbor, Me.) diluted 1:500 in blocking solution] was added to each well and incubated for 1 hour in the dark at room temperature in a humid chamber with shaking 200 μl of PBS was then added, the wells were shaken for an additional minute and wells were emptied. Wells were then washed quickly with washing solution 1, emptied and washed again with washing solution 1 for 10 minutes with shaking Wells were then emptied and rinsed in a tub of PBS followed by rinsing in a tub of double-distilled water.

Additional washes were carried out by submerging slides in a tub of PBS for 10 minutes at room temperature with shaking, followed by a quick submersion in a tub of double-distilled water and 10 minute incubation in a tub of double-distilled water at room temperature with shaking After washing, slides were spun at 200×g for at least 5 minutes to remove all excess water and avoid water stains.

Slides were scanned using GenePix 4000b (Molecular Devices, Sunnyvale, Calif.) immediately for fluorescent signal at 532 nm and 635 nm wavelength under 100% laser power, a 350 gain setting and 10 μm pixel resolution [laser set using GenPixPro 7 software (Molecular Devices, Sunnyvale, Calif.)]. Results from a representative mouse are shown in Table 2. Intensity values were calculated by subtracting raw fluorescence (532 nm) intensity values for each replicate (4 replicates in total) from background fluorescence (532 nm) levels, then averaging the resulting replicate groups to generate an intensity value for each replicate group.

TABLE 2

Glycan microarray results for Group 1 samples

| Glycan | Array ID No | Intensity | Standard Deviation |
|---|---|---|---|
| Neu5Gcα2,6GalNAcαO(CH2)2CH2NH2 | 6 | 550 | 100 |
| Neu5Gcα2,3Galβ1,4GlcNAc6SβO(CH2)2CH2NH2 | 63 | 450 | 0 |
| Neu5Gc9Acα2,6GalNAcαO(CH2)2CH2NH2 | 24 | 400 | 50 |
| Neu5Gcα2,3Galβ1,4(Fucα1,3)GlcNAc6SβO(CH2)2CH2NH2 | 58 | 400 | 0 |
| Neu5Gcα2,6GalβO(CH2)2CH2NH2 | 28 | 350 | 100 |
| Neu5Gc9Acα2,6GalβO(CH2)2CH2NH2 | 32 | 250 | 100 |
| Neu5Gcα2,3GalβO(CH2)2CH2NH2 | 26 | 250 | 100 |
| Neu5Acα2,6(Neu5Gcα2,3)Galβ1,4GlcβO(CH2)2CH2NH2 | 67 | 250 | 0 |
| Neu5Gc9Acα2,3Galβ1,4GlcβO(CH2)2CH2NH2 | 40 | 200 | 0 |
| Neu5Gc9Acα2,6Galβ1,4GlcβO(CH2)2CH2NH2 | 38 | 200 | 0 |
| Neu5Gc9Acα2,3Galβ1,3GalNAcβO(CH2)2CH2NH2 | 36 | 200 | 50 |
| Neu5Gcα2,3Galβ1,4GlcNAcβO(CH2)2CH2NH2 | 12 | 150 | 50 |
| Neu5Gc9Acα2,3Galβ1,4GlcNAcβO(CH2)2CH2NH2 | 2 | 150 | 50 |
| Neu5Gc9Acα2,3GalβO(CH2)2CH2NH2 | 30 | 150 | 0 |
| Neu5Gc9Acα2,3Galβ1,3GlcNAcβO(CH2)2CH2NH2 | 8 | 150 | 0 |
| Neu5Gcα2,3Galβ1,4(Fucα1,3)GlcNAcβO(CH2)2CH2NH2 | 56 | 150 | 50 |
| Neu5Gc9Acα2,6Galβ1,4GlcNAcβO(CH2)2CH2NH2 | 4 | 150 | 50 |
| Neu5Gcα2,3Galβ1,3GlcNAcβO(CH2)2CH2NH2 | 14 | 100 | 50 |
| Neu5Gcα2,6Galβ1,4GlcβO(CH2)2CH2NH2 | 20 | 100 | 100 |
| Neu5Gcα2,3Galβ1,4GlcβO(CH2)2CH2NH2 | 22 | 100 | 50 |
| Neu5Gcα2,6Galβ1,4GlcNAcβO(CH2)2CH2NH2 | 18 | 100 | 50 |
| Neu5Gcα2,3Galβ1,3GalNAcβO(CH2)2CH2NH2 | 34 | 100 | 0 |
| Neu5Gc9Acα2,3Galβ1,3GalNAcαO(CH2)2CH2NH2 | 10 | 100 | 0 |
| Neu5Acα2,6GalβO(CH2)2CH2NH2 | 27 | 50 | 50 |
| Neu5Gcα2,3Galβ1,3GalNAcαO(CH2)2CH2NH2 | 16 | 50 | 0 |
| GalNAcαO(CH2)2CH2NH2 | 47 | 50 | 0 |
| Neu5Acα2,6GalNAcαO(CH2)2CH2NH2 | 5 | 50 | 0 |
| Neu5Gcα2,3Galβ1,3GlcNAcβ1,3Galβ1,4GlcβO(CH2)2CH2NH2 | 61 | 0 | 0 |
| Neu5Acα2,8Neu5Acα2,6Galβ1,4GlcβO(CH2)2CH2NH2 | 76 | 0 | 0 |
| Neu5,9Ac2α2,6GalNAcαO(CH2)2CH2NH2 | 23 | 0 | 0 |
| Neu5Acα2,3Galβ1,3GalNAcβO(CH2)2CH2NH2 | 33 | 0 | 0 |
| Neu5Gcα2,8Neu5Acα2,3Galβ1,4GlcβO(CH2)2CH2NH2 | 69 | 0 | 0 |
| Galβ1,4GlcβO(CH2)2CH2NH2 | 43 | 0 | 0 |
| Neu5,9Ac2α2,3Galβ1,4GlcβO(CH2)2CH2NH2 | 39 | 0 | 0 |
| Neu5Acα2,8Neu5Gcα2,6Galβ1,4GlcβO(CH2)2CH2NH2 | 73 | 0 | 0 |
| Neu5Acα2,3Galβ1,3GlcNAcβO(CH2)2CH2NH2 | 13 | 0 | 0 |
| Galβ1,3GlcNAcβO(CH2)2CH2NH2 | 53 | 0 | 0 |
| Neu5,9Ac2α2,6Galβ1,4GlcβO(CH2)2CH2NH2 | 31 | 0 | 0 |
| Neu5Acα2,6Galβ1,4GlcβO(CH2)2CH2NH2 | 19 | 0 | 0 |
| Neu5,9Ac2α2,3GalβO(CH2)2CH2NH2 | 29 | 0 | 0 |
| KDNα2,8Neu5Gcα2,3Galβ1,4GlcβO(CH2)2CH2NH2 | 74 | 0 | 0 |
| Neu5Acα2,3GalβO(CH2)2CH2NH2 | 25 | 0 | 0 |
| Galβ1,4GlcNAcβO(CH2)2CH2NH2 | 45 | 0 | 0 |
| Galβ1,3GalNAcβO(CH2)2CH2NH2 | 51 | 0 | 0 |
| Neu5,9Ac2α2,6Galβ1,4GlcβO(CH2)2CH2NH2 | 37 | 0 | 0 |
| Galβ1,3GlcNAcαO(CH2)2CH2NH2 | 52 | 0 | 0 |
| Neu5,9Ac2α2,3Galβ1,4GlcNAcβO(CH2)2CH2NH2 | 1 | 0 | 0 |
| Neu5Acα2,3Galβ1,4GlcβO(CH2)2CH2NH2 | 21 | 0 | 0 |

TABLE 2-continued

Glycan microarray results for Group 1 samples

| Glycan | Array ID No | Intensity | Standard Deviation |
|---|---|---|---|
| Neu5Acα2,8Neu5Acα2,3Galβ1,4GlcβO(CH2)2CH2NH2 | 41 | 0 | 0 |
| Galβ1,4GlcNAc6SβO(CH2)2CH2NH2 | 54 | 0 | 0 |
| Neu5Acα2,3Galβ1,3GlcNAcβ1,3Galβ1,4GlcβO(CH2)2CH2NH2 | 60 | 0 | 0 |
| Neu5Acα2,8Kdnα2,6Galβ1,4GlcβO(CH2)2CH2NH2 | 71 | 0 | 0 |
| Neu5Acα2,8Neu5Acα2,8Neu5Acα2,3Galβ1,4GlcβO(CH2)2CH2NH2 | 42 | 0 | 0 |
| Neu5,9Ac2α2,3Galβ1,3GalNAcβO(CH2)2CH2NH2 | 35 | 0 | 0 |
| Neu5,9Ac2α2,3Galβ1,3GlcNAcβO(CH2)2CH2NH2 | 7 | 0 | 0 |
| Neu5Acα2,6Galβ1,4GlcNAcβO(CH2)2CH2NH2 | 17 | 0 | 0 |
| Neu5Acα2,3Galβ1,4(Fucα1,3)GlcNAc6SβO(CH2)2CH2NH2 | 57 | 0 | 0 |
| KDNα2,8Neu5Acα2,3Galβ1,4GlcβO(CH2)2CH2NH2 | 70 | 0 | 0 |
| Neu5Acα2,3Galβ1,4(Fucα1,3)GlcNAcβO(CH2)2CH2NH2 | 55 | 0 | 0 |
| Galβ1,3GlcNAcβ1,3Galβ1,4GlcβO(CH2)2CH2NH2 | 59 | 0 | 0 |
| Neu5Acα2,6(Neu5Acα2,3)Galβ1,4GlcβO(CH2)2CH2NH2 | 66 | 0 | 0 |
| Neu5,9Ac2α2,6Galβ1,4GlcNAcβO(CH2)2CH2NH2 | 3 | 0 | 0 |
| Neu5Acα2,3Galβ1,3GalNAcαO(CH2)2CH2NH2 | 15 | 0 | 0 |
| Neu5Acα2,8Neu5Gcα2,3Galβ1,4GlcβO(CH2)2CH2NH2 | 72 | 0 | 0 |
| Neu5Gcα2,8Neu5Gcα2,3Galβ1,4GlcβO(CH2)2CH2NH2 | 75 | 0 | 0 |
| Neu5,9Ac2α2,3Galβ1,3GalNAcαO(CH2)2CH2NH2 | 9 | 0 | 0 |
| Neu5Acα2,6(KDNα2,3)Galβ1,4GlcβO(CH2)2CH2NH2 | 68 | 0 | 0 |
| Neu5Acα2,3Galβ1,4GlcNAc6SβO(CH2)2CH2NH2 | 62 | 0 | 0 |
| Neu5Acα2,3Galβ1,4GlcNAcβO(CH2)2CH2NH2 | 11 | 0 | 0 |
| Neu5Acα2,8Neu5Acα2,8Neu5Acα2,3Galβ1,4GlcβO(CH2)3NHCOCH2(OCH2CH2)6NH2 | 65 | −50.00 | 50 |
| Neu5Acα2,8Neu5Acα2,3Galβ1,4GlcβO(CH2)3NHCOCH2(OCH2CH2)6NH2 | 64 | −50 | 0 |

Of the glycans that displayed an affinity for the immunized mouse serum, all glycans displaying an intensity value greater than 250 comprised Neu5Gc, with GcSTn (attached to a carbohydrate linker) displaying the greatest affinity. The high affinity glycans identified by the array correlate with the Neu5Gc-rich glycans known to be associated with PSM.

Example 5

Analysis of Group 2 Mouse Samples

Sera collected from Group 2 mice (as described in example 3) were screened by enzyme-linked immunoassay (ELISA) to identify which mice had the strongest immune response to PSM vaccinations. Screening was carried out using de-O-acetylated bovine submaxillary mucin (BSM) as a target. BSM was chosen due to the presence of an antigenically different protein core from that of PSM. This prevents protein-specific antibodies from interfering with the assay. The glycan portion of BSM is similar to that of PSM with the exception of increased levels of 9-O-acetylated sialic acid.

ELISA Protocol

The following materials were used to conduct the ELISA: Coating buffer (1 μg of BSM in 100 μl of 50 mM sodium carbonate/bicarbonate, pH 9.5); washing buffer 1 (WB1) [phosphate buffered saline (PBS), pH 7.3]; washing buffer 2 (WB2) (PBS, pH 7.3 with 0.1% Tween20); blocking buffer (BB) (PBS, pH 7.3 with 1% chicken ovalbumin); citrate/phosphate buffer, pH 5.5 (water with 1.95% citric acid and 3.5% $Na_2HPO_4$); horseradish peroxidase (HRP) substrate [20 ml water, 10 mg o-phenylenediamine dihydrochloride (OPD), 50 μl hydrogen peroxide, 20 μl citrate/phosphate buffer, pH 5.5]; periodate pretreatment buffer (PBS, pH 6.5); washing buffer 3 (WB3) [50 mM sodium acetate, pH 5.5 and 100 mM NaCl (Fisher Scientific, Pittsburgh, Pa.)]; periodate quenching buffer (20 mM $NaBH_4$ in PBS, pH 6.5); periodate treatment buffer (2 mM $NaIO_4$ in PBS, pH 6.5); and control buffer (20 mM $NaBH_4$ and 2 mM $NaIO_4$ in PBS, pH 6.5). Except where otherwise indicated, all chemicals were obtained from Sigma Aldrich (St. Louis, Mo.).

ELISA plate (Corning Life Sciences, Tewksbury, Mass.) wells were BSM coated with coating buffer or coated with mouse IgG standard (Jackson Immunoresearch Laboratories, West Grove, Pa.) overnight at 4° C. Wells were then treated with 0.1 M NaOH for 30 minutes at 37° C. to destroy 9-O-acetylation of BSM. Wells were washed 3 times (200 μl/well) with WB1 before being treated with periodate treatment buffer (to destroy the C6 side chain of sialic acids and reveal whether or not binding in untreated samples is sialic acid-specific) or control buffer for 20 minutes at 4° C. in the dark. IgG standard-treated wells were incubated with PBS, pH 6.5 in place of periodate treatment or control buffer. Wells treated with periodate treatment buffer were then quenched by incubating with periodate quenching buffer for 10 minutes at 4° C. in the dark. Wells were then washed with WB3 for 10 minutes (each wash) at room temperature. Wells were washed again, this time in WB 1 (200 μl/well). Next, wells were blocked with blocking buffer (200 μl/well) for 1 hour at room temperature. Blocking solution was then removed and wells were incubated with a 1:100 dilution of mouse serum in blocking buffer (100 μl/well) with or without 20 mM Neu5Ac or 20 mM Neu5Gc as competitors (to look for the ability of these sialic acids to compete for binding of sera components). Plates were incubated for 2 hours at room temperature before removal of serum and washing 3 times with WB2 (200 μl/well). Wells were next incubated with secondary antibody [100 μl/well of 1:5,000 goat anti-mouse IgG-HRP (Jackson Immunoresearch Laboratories, West Grove, Pa.) in PBS] for one hour at room temperature. Plates were washed 3 times with WB2. Finally, wells were incubated with HRP substrate for 5 minutes at room temperature before stopping the peroxidase reaction with 40 μl of 4 M sulfuric acid. Wells were analyzed spectrophotometrically for absorbance at 490 nm. Absorbance values were adjusted for background readings obtained from control wells containing secondary antibody control only. Adjusted values were compared against IgG standards and used to extrapolate the detectable amount (ng/μl) of antibody in each sample under each condition (see Table 3).

TABLE 3

ELISA analysis of Group 2 mice

| Mouse ID # | Concentration of Reactive Antibody (ng/µl) | | | |
|---|---|---|---|---|
| | +IO$_4$ | −IO$_4$ | +IO$_4$, +20 mM Neu5Gc | −IO$_4$, +20 mM Neu5Gc |
| #1601 | 0.2 | 11.6 | −0.2 | 20.6 |
| #1602 | 0.4 | 76.6 | 0.7 | 79.5 |
| #1603 | 0.9 | 5.6 | 1.0 | 5.3 |
| #1604 | 1.3 | 21.0 | 1.5 | 4.5 |
| #1613 | 2.2 | 19.2 | 1.8 | 17.9 |
| #1614 | 0.6 | 71.1 | 0.8 | 26.3 |
| #1615 | 1.6 | 4.8 | 1.3 | 6.2 |
| #1616 | 2.4 | 41.4 | 14.3 | 41.4 |

Reactivity of all mouse sera were diminished by mild periodate (IO$_4$) treatment, indicating that antibodies specific for glycans comprising sialic acid were detected. Reactivity of mouse serum obtained from mouse #1604 and #1614 was found to be inhibited by the presence of 20 mM Neu5Gc indicating the presence of antibodies specific for glycans comprising Neu5Gc.

Specificity of the mouse sera for Neu5Gc over Neu5Ac was determined through analysis of ELISA results from samples that were subjected to competition with free Neu5Ac. The detectable amount (ng/µl) of antibody in each sample under each condition are listed in Table 4.

TABLE 4

ELISA analysis with Neu5Ac competition

| Mouse ID # | +IO$_4$ | −IO$_4$ | +IO$_4$, +20 mM Neu5Ac | −IO$_4$, +20 mM Neu5Ac |
|---|---|---|---|---|
| #1601 | 0.77 | 13.57 | 14.6 | 26.8 |
| #1602 | 2.24 | 81.82 | 11.3 | 75.6 |
| #1603 | 4.00 | 5.79 | 12.3 | 18.2 |
| #1604 | 4.34 | 23.19 | 16.8 | 31.2 |
| #1613 | 2.02 | 20.89 | 9.8 | 29.2 |
| #1614 | 0.60 | 69.93 | 15.0 | 65.0 |
| #1615 | 0.96 | 3.68 | 21.5 | 28.0 |
| #1616 | 1.52 | 59.82 | 14.3 | 36.9 |

Reactivity of mouse serum from mouse #1604 and #1614 was not inhibited by competition with Neu5Ac. Based on these results, mouse #1604 and #1614 were identified as having a strong immune response to glycans comprising Neu5Gc.

Group 2 serum samples were also analyzed by glycan microarray according to the protocol disclosed in example 4. Results are shown in Table 5 as average intensity values calculated by subtracting sample fluorescence levels from background fluorescence levels for each of four replicates and then averaging the resulting values.

TABLE 5

Glycan microarray results for Group 2 mice

| Glycan ID | Glycan | Intensity by Mouse ID # | | | | | | | |
|---|---|---|---|---|---|---|---|---|---|
| | | #1616 | #1615 | #1614 | #1613 | #1604 | #1603 | #1602 | #1601 |
| 1 | Neu5,9Ac2α2,3Galβ1,4GlcNAcβO(CH2)2CH2NH2 | 0 | 0 | 0 | 0 | 0 | 0 | 0 | 0 |
| 2 | Neu5Gc9Acα2,3Galβ1,4GlcNAcβO(CH2)2CH2NH2 | 0 | 50 | 400 | 50 | 50 | 0 | 0 | 50 |
| 3 | Neu5,9Ac2α2,6Galβ1,4GlcNAcβO(CH2)2CH2NH2 | 0 | 0 | 0 | 0 | 0 | 0 | 0 | 0 |
| 4 | Neu5Gc9Acα2,6Galβ1,4GlcNAcβO(CH2)2CH2NH2 | 0 | 0 | 1250 | 100 | 50 | 0 | 50 | 0 |
| 5 | Neu5Acα2,6GalNAcαO(CH2)2CH2NH2 | 0 | 100 | 0 | 0 | 50 | 0 | 0 | 0 |
| 6 | Neu5Gcα2,6GalNAcαO(CH2)2CH2NH2 | 650 | 50 | 5000 | 950 | 550 | 0 | 50 | 550 |
| 7 | Neu5,9Ac2α2,3Galβ1,GlcNAcβO(CH2)2CH2NH2 | 0 | 0 | 0 | 0 | 0 | 0 | 0 | 0 |
| 8 | Neu5Gc9Acα2,3Galβ1,3GlcNAcβO(CH2)2CH2NH2 | −50 | 0 | 250 | 100 | 100 | 0 | 50 | 300 |
| 9 | Neu5,9Ac2α2,3Galβ1,3GalNAcαO(CH2)2CH2NH2 | 0 | 0 | 0 | 0 | 0 | 0 | 0 | 0 |
| 10 | Neu5Gc9Acα2,3Galβ1,3GalNAcαO(CH2)2CH2NH2 | 0 | 50 | 150 | 0 | 0 | 0 | 0 | 50 |
| 11 | Neu5Acα2,3Galβ1,4GlcNAcβO(CH2)2CH2NH2 | 0 | 50 | 0 | 0 | 0 | 0 | 0 | 0 |
| 12 | Neu5Gcα2,3Galβ1,4GlcNAcβO(CH2)2CH2NH2 | 50 | 0 | 400 | 50 | 100 | 0 | 0 | 550 |
| 13 | Neu5Acα2,3Galβ1,3GlcNAcβO(CH2)2CH2NH2 | 0 | 0 | 0 | 0 | 0 | 0 | 0 | 0 |
| 14 | Neu5Gcα2,3Galβ1,3GlcNAcβO(CH2)2CH2NH2 | 0 | 0 | 150 | 0 | 0 | 0 | 0 | 350 |
| 15 | Neu5Acα2,3Galβ1,3GalNAcαO(CH2)2CH2NH2 | 0 | 0 | 0 | 0 | 0 | 0 | 0 | 0 |
| 16 | Neu5Gcα2,3Galβ1,3GalNAcαO(CH2)2CH2NH2 | 0 | 0 | 100 | 50 | 50 | 0 | 50 | 100 |
| 17 | Neu5Acα2,6Galβ1,4GlcNAcβO(CH2)2CH2NH2 | 0 | 0 | 0 | 0 | 0 | 0 | 0 | 0 |
| 18 | Neu5Gcα2,6Galβ1,4GlcNAcβO(CH2)2CH2NH2 | 50 | 0 | 450 | 100 | 50 | 0 | 0 | 50 |
| 19 | Neu5Acα2,6Galβ1,4GlcβO(CH2)2CH2NH2 | 0 | 0 | 0 | 0 | 0 | 0 | 0 | 0 |
| 20 | Neu5Gcα2,6Galβ1,4GlcβO(CH2)2CH2NH2 | 50 | 0 | 350 | 100 | 250 | 0 | 50 | 0 |
| 21 | Neu5Acα2,3Galβ1,4GlcβO(CH2)2CH2NH2 | 0 | 0 | 0 | 0 | 0 | 0 | 0 | 0 |
| 22 | Neu5Gcα2,3Galβ1,4GlcβO(CH2)2CH2NH2 | 0 | 0 | 200 | 50 | 150 | 0 | 0 | 150 |
| 23 | Neu5,9Ac2α2,6GalNAcαO(CH2)2CH2NH2 | 50 | 50 | 0 | 0 | 50 | 0 | 50 | 0 |
| 24 | Neu5Gc9Acα2,6GalNAcαO(CH2)2CH2NH2 | 250 | 50 | 3050 | 250 | 400 | 0 | 100 | 350 |
| 25 | Neu5Acα2,3GalβO(CH2)2CH2NH2 | 0 | 0 | 100 | 0 | 0 | 0 | 0 | 0 |
| 26 | Neu5Gcα2,3GalβO(CH2)2CH2NH2 | 50 | 0 | 650 | 150 | 400 | 0 | 50 | 1150 |
| 27 | Neu5Acα2,6GalβO(CH2)2CH2NH2 | 0 | 0 | 0 | 0 | 50 | 0 | 0 | 0 |
| 28 | Neu5Gcα2,6GalβO(CH2)2CH2NH2 | 50 | 0 | 550 | 250 | 400 | 0 | 50 | 50 |
| 29 | Neu5,9Ac2α2,3GalβO(CH2)2CH2NH2 | 0 | 0 | 0 | 0 | 0 | 0 | 0 | 0 |
| 30 | Neu5Gc9Acα2,3GalβO(CH2)2CH2NH2 | 0 | 0 | 100 | 0 | 0 | 0 | 50 | 50 |
| 31 | Neu5,9Ac2α2,6GalβO(CH2)2CH2NH2 | 0 | 0 | 0 | 0 | 50 | 0 | 0 | 0 |

TABLE 5-continued

Glycan microarray results for Group 2 mice

| Glycan ID | Glycan | Intensity by Mouse ID # | | | | | | | |
|---|---|---|---|---|---|---|---|---|---|
| | | #1616 | #1615 | #1614 | #1613 | #1604 | #1603 | #1602 | #1601 |
| 32 | Neu5Gc9Acα2,6GalβO(CH2)2CH2NH2 | 100 | 50 | 1450 | 200 | 550 | 0 | 50 | 100 |
| 33 | Neu5Acα2,3Galβ1,3GalNAcβO(CH2)2CH2NH2 | 0 | 0 | 0 | 0 | 0 | 0 | 0 | 0 |
| 34 | Neu5Gcα2,3Galβ1,3GalNAcβO(CH2)2CH2NH2 | 0 | 0 | 50 | 50 | 50 | 0 | 50 | 650 |
| 35 | Neu5,9Ac2α2,3Galβ1,3GalNAcβO(CH2)2CH2NH2 | 0 | 0 | 0 | 0 | 0 | 0 | 0 | 0 |
| 36 | Neu5Gc9Acα2,3Galβ1,3GalNAcβO(CH2)2CH2NH2 | 0 | 250 | 50 | 50 | 0 | 0 | 50 | 350 |
| 37 | Neu5,9Ac2α2,6Galβ1,4GlcβO(CH2)2CH2NH2 | 0 | 0 | 0 | 0 | 0 | 0 | 0 | 0 |
| 38 | Neu5Gc9Acα2,6Galβ1,4GlcβO(CH2)2CH2NH2 | 50 | 50 | 500 | 200 | 200 | 0 | 0 | 50 |
| 39 | Neu5,9Ac2α2,3Galβ1,4GlcβO(CH2)2CH2NH2 | 0 | 0 | 0 | 0 | 0 | 0 | 0 | 0 |
| 40 | Neu5Gc9Acα2,3Galβ1,4GlcβO(CH2)2CH2NH2 | 0 | 50 | 50 | 50 | 50 | 0 | 0 | 350 |
| 41 | Neu5Acα2,8Neu5Acα2,3Galβ1,4GlcβO(CH2)2CH2NH2 | 0 | 0 | 0 | 0 | 0 | 0 | 0 | 0 |
| 42 | Neu5Acα2,8Neu5Acα2,8Neu5Acα2,3Galβ1,4GlcβO(CH2)2CH2NH2 | 0 | 0 | 0 | 0 | 0 | 0 | 0 | 0 |
| 43 | Galβ1,4GlcβO(CH2)2CH2NH2 | 0 | 0 | 0 | 0 | 0 | 0 | 0 | 0 |
| 45 | Galβ1,4GlcNAcβO(CH2)2CH2NH2 | 0 | 0 | 0 | 0 | 0 | 0 | 0 | 0 |
| 47 | GalNAcαO(CH2)2CH2NH2 | 0 | 50 | 0 | 0 | 50 | 50 | 100 | 50 |
| 51 | Galβ1,3GalNAcβO(CH2)2CH2NH2 | 0 | 0 | 0 | 0 | 0 | 0 | 0 | 0 |
| 52 | Galβ1,3GlcNAcαO(CH2)2CH2NH2 | 0 | 0 | 0 | 0 | 0 | 0 | 0 | 0 |
| 53 | Galβ1,3GlcNAcβO(CH2)2CH2NH2 | 0 | 0 | 0 | 0 | 0 | 0 | 0 | 0 |
| 54 | Galβ1,4GlcNAc6SβO(CH2)2CH2NH2 | 50 | 0 | 0 | 0 | 0 | 0 | 0 | 0 |
| 55 | Neu5Acα2,3Galβ1,4(Fucα1,3)GlcNAcβO(CH2)2CH2NH2 | 0 | 0 | 0 | 0 | 0 | 0 | 0 | 0 |
| 56 | Neu5Gcα2,3Galβ1,4(Fucα1,3)GlcNAcβO(CH2)2CH2NH2 | 0 | 0 | 50 | 50 | 50 | 0 | 0 | 50 |
| 57 | Neu5Acα2,3Galβ1,4(Fucα1,3)GlcNAc6SβO(CH2)2CH2NH2 | 0 | 0 | 0 | 0 | 0 | 0 | 0 | 0 |
| 58 | Neu5Gcα2,3Galβ1,4(Fucα1,3)GlcNAc6SβO(CH2)2CH2NH2 | 100 | 0 | 550 | 350 | 450 | 0 | 50 | 50 |
| 59 | Galβ1,3GlcNAcβ1,3Galβ1,4GlcβO(CH2)2CH2NH2 | 0 | 0 | 0 | 0 | 0 | 0 | 0 | 0 |
| 60 | Neu5Acα2,3Galβ1,3GlcNAcβ1,3Galβ1,4GlcβO(CH2)2CH2NH2 | 0 | 0 | 0 | 0 | 0 | 0 | 0 | 0 |
| 61 | Neu5Gcα2,3Galβ1,3GlcNAcβ1,3Galβ1,4GlcβO(CH2)2CH2NH2 | 0 | 0 | 0 | 0 | 50 | 0 | 0 | 0 |
| 62 | Neu5Acα2,3Galβ1,4GlcNAc6SβO(CH2)2CH2NH2 | 0 | 0 | 0 | 0 | 0 | 0 | 0 | 0 |
| 63 | Neu5Gcα2,3Galβ1,4GlcNAc6SβO(CH2)2CH2NH2 | 150 | 0 | 1000 | 350 | 1300 | 0 | 50 | 900 |
| 64 | Neu5Acα2,8Neu5Acα2,3Galβ1,4GlcβO(CH2)3NHCOCH2(OCH2CH2)6NH2 | 0 | 0 | 0 | 0 | 0 | 0 | 0 | 0 |
| 65 | Neu5Acα2,8Neu5Acα2,8Neu5Acα2,3Galβ1,4GlcβO(CH2)3NHCOCH2(OCH2CH2)6NH2 | 0 | 0 | 0 | 0 | 0 | 0 | 0 | 0 |
| 66 | Neu5Acα2,6(Neu5Acα2,3)Galβ1,4GlcβO(CH2)2CH2NH2 | 0 | 0 | 0 | 0 | 0 | 0 | 0 | 0 |
| 67 | Neu5Acα2,6(Neu5Gcα2,3)Galβ1,4GlcβO(CH2)2CH2NH2 | 50 | 0 | 50 | 50 | 100 | 0 | 0 | 150 |
| 68 | Neu5Acα2,6(KDNα2,3)Galβ1,4GlcβO(CH2)2CH2NH2 | 0 | 0 | 0 | 0 | 0 | 0 | 0 | 0 |
| 69 | Neu5Gcα2,8Neu5Acα2,3Galβ1,4GlcβO(CH2)2CH2NH2 | 0 | 0 | 0 | 0 | 0 | 0 | 0 | 0 |
| 70 | KDNα2,8Neu5Acα2,3Galβ1,4GlcβO(CH2)2CH2NH2 | 0 | 0 | 0 | 0 | 0 | 0 | 0 | 0 |
| 71 | Neu5Acα2,8Kdnα2,6Galβ1,4GlcβO(CH2)2CH2NH2 | 0 | 0 | 0 | 0 | 0 | 0 | 0 | 0 |
| 72 | Neu5Acα2,8Neu5Gcα2,3Galβ1,4GlcβO(CH2)2CH2NH2 | 0 | 0 | 0 | 0 | 0 | 0 | 50 | 0 |
| 73 | Neu5Acα2,8Neu5Gcα2,6Galβ1,4GlcβO(CH2)2CH2NH2 | 0 | 0 | 0 | 0 | 0 | 0 | 0 | 0 |
| 74 | KDNα2,8Neu5Gcα2,3Galβ1,4GlcβO(CH2)2CH2NH2 | 0 | 0 | 0 | 0 | 0 | 0 | 50 | 0 |
| 75 | Neu5Gcα2,8Neu5Gcα2,3Galβ1,4GlcβO(CH2)2CH2NH2 | 0 | 0 | 0 | 0 | 0 | 0 | 50 | 0 |
| 76 | Neu5Acα2,8Neu5Acα2,6Galβ1,4GlcβO(CH2)2CH2NH2 | 0 | 0 | 0 | 0 | 0 | 0 | 0 | 0 |

Mouse sera from mouse numbers 1601, 1604, 1613, 1614 and 1616 demonstrated high affinity for GcSTn (Glycan ID #6) indicating an immune response against PSM. Sera from mouse #1614 demonstrated the highest affinity for GcSTn. Sera from mouse numbers 1602, 1603 and 1615 did not demonstrate an immune response against GcSTn. Standard deviations for each average intensity value are listed in Table 6.

TABLE 6

Standard deviation values for glycan microarray results listed in Table 5

| | | Standard Deviation for intensity levels by Mouse ID # | | | | | | | |
|---|---|---|---|---|---|---|---|---|---|
| Glycan ID | Glycan | #1616 | #1615 | #1614 | #1613 | #1604 | #1603 | #1602 | #1601 |
| 1 | Neu5,9Ac2α2,3Galβ1,4GlcNAcβO(CH2)2CH2NH2 | 0 | 0 | 0 | 0 | 0 | 0 | 0 | 0 |
| 2 | Neu5Gc9Acα2,3Galβ1,4GlcNAcβO(CH2)2CH2NH2 | 50 | 0 | 100 | 0 | 0 | 0 | 0 | 0 |
| 3 | Neu5,9Ac2α2,6Galβ1,4GlcNAcβO(CH2)2CH2NH2 | 0 | 0 | 0 | 0 | 0 | 0 | 0 | 0 |
| 4 | Neu5Gc9Acα2,6Galβ1,4GlcNAcβO(CH2)2CH2NH2 | 0 | 0 | 150 | 0 | 50 | 0 | 0 | 0 |
| 5 | Neu5Acα2,6GalNAcαO(CH2)2CH2NH2 | 50 | 0 | 0 | 0 | 0 | 0 | 0 | 0 |
| 6 | Neu5Gcα2,6GalNAcαO(CH2)2CH2NH2 | 300 | 0 | 650 | 200 | 150 | 0 | 0 | 50 |
| 7 | Neu5,9Ac2α2,3Galβ1,3GlcNAcβO(CH2)2CH2NH2 | 0 | 0 | 0 | 0 | 0 | 0 | 0 | 0 |
| 8 | Neu5Gc9Acα2,3Galβ1,3GlcNAcβO(CH2)2CH2NH2 | 50 | 0 | 50 | 0 | 0 | 0 | 0 | 100 |
| 9 | Neu5,9Ac2α2,3Galβ1,3GalNAcαO(CH2)2CH2NH2 | 0 | 0 | 0 | 0 | 0 | 0 | 0 | 0 |
| 10 | Neu5Gc9Acα2,3Galβ1,3GalNAcαO(CH2)2CH2NH2 | 0 | 0 | 50 | 0 | 0 | 0 | 0 | 0 |
| 11 | Neu5Acα2,3Galβ1,4GlcNAcβO(CH2)2CH2NH2 | 50 | 0 | 0 | 0 | 0 | 0 | 0 | 0 |
| 12 | Neu5Gcα2,3Galβ1,4GlcNAcβO(CH2)2CH2NH2 | 50 | 0 | 100 | 0 | 0 | 0 | 0 | 100 |
| 13 | Neu5Acα2,3Galβ1,3GlcNAcβO(CH2)2CH2NH2 | 0 | 0 | 0 | 0 | 0 | 0 | 0 | 0 |
| 14 | Neu5Gcα2,3Galβ1,3GlcNAcβO(CH2)2CH2NH2 | 0 | 0 | 0 | 0 | 0 | 0 | 0 | 150 |
| 15 | Neu5Acα2,3Galβ1,3GalNAcαO(CH2)2CH2NH2 | 0 | 0 | 0 | 0 | 0 | 0 | 0 | 0 |
| 16 | Neu5Gcα2,3Galβ1,3GalNAcαO(CH2)2CH2NH2 | 0 | 0 | 50 | 0 | 0 | 0 | 0 | 0 |
| 17 | Neu5Acα2,6Galβ1,4GlcNAcβO(CH2)2CH2NH2 | 0 | 0 | 0 | 0 | 0 | 0 | 0 | 0 |
| 18 | Neu5Gcα2,6Galβ1,4GlcNAcβO(CH2)2CH2NH2 | 0 | 0 | 50 | 50 | 0 | 0 | 0 | 0 |
| 19 | Neu5Acα2,6Galβ1,4GlcβO(CH2)2CH2NH2 | 0 | 0 | 0 | 0 | 0 | 0 | 0 | 0 |
| 20 | Neu5Gcα2,6Galβ1,4GlcβO(CH2)2CH2NH2 | 0 | 0 | 200 | 50 | 0 | 0 | 0 | 0 |
| 21 | Neu5Acα2,3Galβ1,4GlcβO(CH2)2CH2NH2 | 0 | 0 | 0 | 0 | 0 | 0 | 0 | 0 |
| 22 | Neu5Gcα2,3Galβ1,4GlcβO(CH2)2CH2NH2 | 0 | 0 | 0 | 0 | 50 | 0 | 0 | 50 |
| 23 | Neu5,9Ac2α2,6GalNAcαO(CH2)2CH2NH2 | 0 | 0 | 0 | 0 | 0 | 0 | 0 | 0 |
| 24 | Neu5Gc9Acα2,6GalNAcαO(CH2)2CH2NH2 | 0 | 0 | 100 | 50 | 50 | 0 | 0 | 50 |
| 25 | Neu5Acα2,3GalβO(CH2)2CH2NH2 | 0 | 0 | 0 | 0 | 0 | 0 | 0 | 0 |
| 26 | Neu5Gcα2,3GalβO(CH2)2CH2NH2 | 0 | 0 | 100 | 50 | 50 | 0 | 0 | 100 |
| 27 | Neu5Acα2,6GalβO(CH2)2CH2NH2 | 0 | 0 | 0 | 0 | 100 | 0 | 0 | 0 |
| 28 | Neu5Gcα2,6GalβO(CH2)2CH2NH2 | 0 | 0 | 250 | 150 | 250 | 0 | 0 | 0 |
| 29 | Neu5,9Ac2α2,3GalβO(CH2)2CH2NH2 | 0 | 0 | 0 | 0 | 0 | 0 | 0 | 0 |
| 30 | Neu5Gc9Acα2,3GalβO(CH2)2CH2NH2 | 0 | 0 | 50 | 0 | 0 | 0 | 100 | 50 |
| 31 | Neu5,9Ac2α2,6GalβO(CH2)2CH2NH2 | 0 | 0 | 0 | 0 | 0 | 0 | 0 | 0 |
| 32 | Neu5Gc9Acα2,6GalβO(CH2)2CH2NH2 | 0 | 0 | 300 | 100 | 100 | 0 | 50 | 50 |
| 33 | Neu5Acα2,3Galβ1,3GalNAcβO(CH2)2CH2NH2 | 0 | 0 | 0 | 0 | 0 | 0 | 0 | 0 |
| 34 | Neu5Gcα2,3Galβ1,3GalNAcβO(CH2)2CH2NH2 | 0 | 0 | 0 | 0 | 0 | 0 | 0 | 200 |
| 35 | Neu5,9Ac2α2,3Galβ1,3GalNAcβO(CH2)2CH2NH2 | 0 | 0 | 0 | 0 | 0 | 0 | 0 | 0 |
| 36 | Neu5Gc9Acα2,3Galβ1,3GalNAcβO(CH2)2CH2NH2 | 0 | 0 | 0 | 0 | 0 | 0 | 0 | 50 |
| 37 | Neu5,9Ac2α2,6Galβ1,4GlcβO(CH2)2CH2NH2 | 0 | 0 | 50 | 0 | 0 | 0 | 0 | 0 |
| 38 | Neu5Gc9Acα2,6Galβ1,4GlcβO(CH2)2CH2NH2 | 0 | 0 | 50 | 0 | 50 | 0 | 0 | 0 |
| 39 | Neu5,9Ac2α2,3Galβ1,4GlcIβO(CH2)2CH2NH2 | 0 | 0 | 0 | 0 | 0 | 0 | 0 | 0 |
| 40 | Neu5Gc9Acα2,3Galβ1,4GlcβO(CH2)2CH2NH2 | 0 | 0 | 0 | 0 | 0 | 0 | 0 | 50 |
| 41 | Neu5Acα2,8Neu5Acα2,3Galβ1,4GlcβO(CH2)2CH2NH2 | 0 | 0 | 0 | 0 | 0 | 0 | 0 | 0 |
| 42 | Neu5Acα2,8Neu5Acα2,8Neu5Acα2,3Galβ1,4GlcβO(CH2)2CH2NH2 | 0 | 0 | 0 | 0 | 0 | 0 | 0 | 0 |
| 43 | Galβ1,4GlcβO(CH2)2CH2NH2 | 0 | 0 | 0 | 0 | 0 | 0 | 0 | 0 |
| 45 | Galβ1,4GlcNAcβO(CH2)2CH2NH2 | 0 | 0 | 0 | 0 | 0 | 0 | 0 | 0 |
| 47 | GalNAcαO(CH2)2CH2NH2 | 0 | 0 | 0 | 0 | 0 | 50 | 100 | 0 |
| 51 | Galβ1,3GalNAcβO(CH2)2CH2NH2 | 0 | 0 | 0 | 0 | 0 | 0 | 0 | 0 |
| 52 | Galβ1,3GlcNAcαO(CH2)2CH2NH2 | 0 | 0 | 0 | 0 | 0 | 0 | 0 | 0 |
| 53 | Galβ1,3GlcNAcβO(CH2)2CH2NH2 | 0 | 0 | 0 | 0 | 0 | 0 | 0 | 0 |
| 54 | Galβ1,4GlcNAc6SβO(CH2)2CH2NH2 | 0 | 0 | 0 | 0 | 0 | 0 | 0 | 0 |
| 55 | Neu5Acα2,3Galβ1,4(Fucα1,3)GlcNAcβO(CH2)2CH2NH2 | 0 | 0 | 0 | 0 | 0 | 0 | 0 | 0 |

TABLE 6-continued

Standard deviation values for glycan microarray results listed in Table 5

| | | Standard Deviation for intensity levels by Mouse ID # | | | | | | | |
|---|---|---|---|---|---|---|---|---|---|
| Glycan ID | Glycan | #1616 | #1615 | #1614 | #1613 | #1604 | #1603 | #1602 | #1601 |
| 56 | Neu5Gcα2,3Galβ1,4(Fucα1,3)GlcNAcβO(CH2)2CH2NH2 | 0 | 0 | 0 | 0 | 0 | 0 | 0 | 0 |
| 57 | Neu5Acα2,3Galβ1,4(Fucα1,3)GlcNAc6SβO(CH2)2CH2NH2 | 0 | 0 | 0 | 0 | 0 | 0 | 0 | 0 |
| 58 | Neu5Gcα2,3Galβ1,4(Fucα1,3)GlcNAc6SβO(CH2)2CH2NH2 | 0 | 0 | 50 | 50 | 50 | 0 | 0 | 0 |
| 59 | Galβ1,3GlcNAcβ1,3Galβ1,4GlcβO(CH2)2CH2NH2 | 0 | 0 | 0 | 0 | 0 | 0 | 0 | 0 |
| 60 | Neu5Acα2,3Galβ1,3GlcNAcβ1,3Galβ1,4GlcβO(CH2)2CH2NH2 | 0 | 0 | 0 | 0 | 0 | 0 | 0 | 0 |
| 61 | Neu5Gcα2,3Galβ1,3GlcNAcβ1,3Galβ1,4GlcβO(CH2)2CH2NH2 | 0 | 0 | 0 | 0 | 0 | 0 | 0 | 0 |
| 62 | Neu5Acα2,3Galβ1,4GlcNAc6SβO(CH2)2CH2NH2 | 0 | 0 | 0 | 0 | 0 | 0 | 0 | 0 |
| 63 | Neu5Gcα2,3Galβ1,4GlcNAc6SβO(CH2)2CH2NH2 | 100 | 0 | 100 | 0 | 200 | 0 | 0 | 200 |
| 64 | Neu5Acα2,8Neu5Acα2,3Galβ1,4GlcβO(CH2)3NHCOCH2(OCH2CH2)6NH2 | 0 | 0 | 0 | 0 | 0 | 0 | 0 | 0 |
| 65 | Neu5Acα2,8Neu5Acα2,8Neu5Acα2,3Galβ1,4GlcβO(CH2)3NHCOCH2(OCH2CH2)6NH2 | 0 | 0 | 0 | 0 | 0 | 0 | 0 | 0 |
| 66 | Neu5Acα2,6(Neu5Acα2,3)Galβ1,4GlcβO(CH2)2CH2NH2 | 0 | 0 | 0 | 0 | 0 | 0 | 0 | 0 |
| 67 | Neu5Acα2,6(Neu5Gcα2,3)Galβ1,4GlcβO(CH2)2CH2NH2 | 0 | 0 | 0 | 0 | 0 | 0 | 0 | 50 |
| 68 | Neu5Acα2,6(KDNα2,3)Galβ1,4GlcβO(CH2)2CH2NH2 | 0 | 0 | 0 | 0 | 0 | 0 | 0 | 0 |
| 69 | Neu5Gcα2,8Neu5Acα2,3Galβ1,4GlcβO(CH2)2CH2NH2 | 0 | 0 | 0 | 0 | 0 | 0 | 0 | 0 |
| 70 | KDNα2,8Neu5Acα2,3Galβ1,4GlcβO(CH2)2CH2NH2 | 0 | 0 | 0 | 0 | 0 | 0 | 0 | 0 |
| 71 | Neu5Acα2,8Kdnα2,6Galβ1,4GlcβO(CH2)2CH2NH2 | 0 | 0 | 0 | 0 | 0 | 0 | 0 | 0 |
| 72 | Neu5Acα2,8Neu5Gcα2,3Galβ1,4GlcβO(CH2)2CH2NH2 | 0 | 0 | 0 | 0 | 0 | 0 | 0 | 0 |
| 73 | Neu5Acα2,8Neu5Gcα2,6Galβ1,4GlcβO(CH2)2CH2NH2 | 0 | 0 | 0 | 0 | 0 | 0 | 0 | 0 |
| 74 | KDNα2,8Neu5Gcα2,3Galβ1,4GlcβO(CH2)2CH2NH2 | 0 | 0 | 0 | 0 | 0 | 0 | 0 | 0 |
| 75 | Neu5Gcα2,8Neu5Gcα2,3Galβ1,4GlcβO(CH2)2CH2NH2 | 0 | 0 | 0 | 0 | 0 | 0 | 0 | 0 |
| 76 | Neu5Acα2,8Neu5Acα2,6Galβ1,4GlcβO(CH2)2CH2NH2 | 0 | 0 | 0 | 0 | 0 | 0 | 0 | 0 |

Based on the results of Group 2 serum analysis, mouse #1614 was determined to have demonstrated the most robust immune response to GcSTn present on PSM in the study group. This GcSTn reactivity could be inhibited with 20 mM Neu5Gc, but not with 20 mM Neu5Ac in the ELISA experiment highlighting the specificity of this immune response.

Example 6

Phage Library Construction and Selection

RNA is prepared from spleens harvested from mice with a strong immune response to GcSTn present in PSM. Mouse variable (V) regions are PCR amplified and assembled into scFv expression constructs. ScFv sequences are cloned into phagemid display vectors allowing for scFv display on the surface of M13 phage particles. The resulting library is transformed into E. coli (TG1). Bulk transformations of E. coli are grown and phage are prepared by phage rescue. In the first round of selection, phage from the culture medium are purified by PEG precipitation.

Candidate scFvs are selected using both negative and positive selection methods. For negative selection, the library is incubated with "destroyed" STn-negative mucin (e.g. chemically treated PSM). For positive selection, the library is incubated with GcSTn mucin (e.g. PSM and/or de-O-acetylated BSM) and a synthetic Neu5Gc glycan in the presence of Neu5Ac (or optionally, incubation with AcSTn mucin and synthetic Neu5Ac glycan in the presence of Neu5Gc in an additional analysis).

After 3-4 rounds of selection with reducing antigen concentrations, 1000 clones are analyzed by ELISA for binding to GcSTn (or AcSTn in the additional analysis) using synthetic and natural glycan targets. Lead phage/scFv candidates are tested in a secondary FACS-based cellular assay for binding to GcSTn and AcSTn using Jurkat cells with or without "induction" of GcSTn or AcSTn. Up to 20 selected scFv candidates of interest are subjected to further analysis.

Example 7

Conversion of scFvs to Whole IgG 3 lead scFv candidates are selected for conversion to IgG. V regions from each scFv are cloned into mammalian expression vectors between an upstream CMV promoter and a downstream immunoglobulin constant region. Heavy chain vector includes murine IgG1 and κ constant regions. Vectors are transiently transfected into HEK293/EBNA cells. Antibody samples are purified and characterized by binding to

Example 8

Antibody-Dependent Cell-Mediated Cytotoxicity Optimization

Genes encoding the variable regions of a selected IgG are cloned into mammalian expression vectors encoding human Fc regions (huIgG1κ) containing amino acid mutations known to enhance Fc-receptor binding and antibody-dependent cell-mediated cytotoxicity (ADCC). Vectors are transiently transfected into HEK293/EBNA cells. After 48 hours, IgG expression is quantified and samples of antibody are purified on protein A columns. Antibodies are then tested in ADCC assays. Neu5Gc and Neu5Ac-expressing Jurkat cell lines are used as the target cells and human peripheral blood mononuclear cells (PBMC) are used as a source of effector cells. Target cells are titrated using maximum cell lysis to determine the optimum cell density for use in multiwall plate format assay. ADCC-mutated antibody together with the non-mutated IgG are pre-incubated with target cells, effector cells are then added at varying target:effector cell ratios, and cultures are incubated at 37° C. Percentage viability is determined using Calcein-AM dye (BD Biosciences, San Jose, Calif.) release. Samples of up to 0.5 mg of ADCC-mutated IgG are subjected to further analysis.

Example 9

Production of Lead Antibody from Semi-Stable HEK Cell Line

V regions from IgG are cloned into mammalian expression vectors between an upstream CMV promoter and a downstream immunoglobulin constant region. Heavy chain vector includes murine IgG1 and κ constant regions. Vectors are transiently transfected into HEK293/EBNA cells and antibody titers are assessed at 72 hours. Transiently transfected HEK293/EBNA cells are selected with hygromycin to establish a semi-stable expression system. Semi-stable cells are expanded to 10 liters. Antibodies are purified from the culture supernatant by Protein A, dialyzed into PBS and the resulting preparation is analyzed for (1) aggregates by analytical size exclusion chromatography (SEC), (2) endotoxin levels by *Limulus amebocyte* lysate (LAL) testing (expressed as EU/mg), and (3) binding to antigen in the primary assay.

Example 10

Additional Assays for Screening scFv Candidates for Target Affinity

ScFv candidates are subjected to additional screening methods for GcSTn affinity using a variety of proposed targets.
Synthetic Glycan Target Screening
As used herein, the term "target screening" refers to the use of a target substance to identify binding partners for that substance. Synthetic glycan target screening is carried out using GcSTn bound to poly(acrylic acid) (PAA) with a biotin tag. AcSTn and Tn bound to PAA with a biotin tag are used as negative controls. Cells associated with candidate scFvs are isolated through precipitation with avidin-associated entities.

Natural Glycan Target Screening on Live Cells
Target screening using live cells is carried out using Jurkat cells fed with Neu5Gc or Jurkat cells fed with Neu5Ac as a negative control. Target screening using live cells is also carried out using MCF-7 or MDA-MB-231 cells fed with Neu5Gc (or Neu5Ac in negative control screening) and stable transfection. Flow cytometry is used in either case to isolate cells associated with scFv candidates.
Natural Glycan Target Screening on Tissue (Ex Vivo)
Target screening using ex vivo tissue is carried out using biopsy tissue samples. Binding of scFv candidates with ex vivo tissue is analyzed using standard immunohistochemical methods. Single tissue sections as well as tissue microarray sections are used. Samples are treated with or without sialidase and/or periodate in control experiments.

Example 11

Demonstration of In Vivo Tumor Killing Ability

In vivo tumor killing ability is demonstrated with mouse and/or human tumor cell lines. Tumor cell lines expressing GcSTn are transferred into mice and the ability of the antibody candidates to kill the resulting tumors is determined.

Mouse cell lines used in vivo in tumor killing assay include the mouse colon adenocarcinoma cell line, MC38, derived from C57BL/6 mice and stably transfected with ST6 (alpha-N-acetyl-neuraminyl-2,3-beta-galactosyl-1,3)-N-acetylgalactosaminide alpha2,6-sialyltransferase 1 (ST6GalNAc1). These cells are fed with Neu5Gc before their use in vivo tumor killing assays using syngeneic Cmah$^{-/-}$ mice.

Alternatively, for in vivo tumor killing assays human breast cancer cell lines (T47-D, MCF-7 or MDA-MB-231) induced to express a high level of GcSTn (after stable transfection of ST6GalNac1 and feeding with Neu5Gc) are transferred into immune-deficient FOXN1-/- (nude) cells, non-obese diabetic (NOD) cells, or severe immunodeficiency (SCID) mice.

In vivo ADCC is induced by passive transfer of human peripheral blood mononuclear cells (PBMCs) or purified natural killer (NK) cells. In cases where candidate antibodies bind unspecifically to wild-type mouse tissue, immune-deficient mice are bred into the Cmah -/- background.

Example 12

Antibody Humanization

Fully humanized heavy and light chains are designed. Protein models of the variable regions are generated using existing antibody structures as templates. Segments of starting heavy and light chain variable region amino acid sequences are compared with human sequences for possible inclusion in the fully humanized sequences. Series of humanized heavy and light chain variable regions are designed entirely from segments of human variable region sequences with the objective that T cell epitopes be avoided. Variant human sequence segments with significant incidence of potential T cell epitopes as determined by in silico technologies are discarded.

Humanized heavy and light chain variable region genes are constructed from overlapping oligonucleotides assembled into full length genes using the ligase chain reaction (LCR). LCR products are amplified and suitable restriction sites are added for cloning into expression vectors. PCR products are cloned into intermediate vectors and confirmed by sequencing.

For construction of expression plasmids encoding fully humanized antibodies with human constant regions, DNA sequences for each variable region are inserted into mammalian expression vectors between an upstream cytomegalovirus immediate/early promoter/enhancer (CMV IE) plus the immunoglobulin signal sequence and a downstream immunoglobulin constant region gene. DNA samples are prepared for transfection into mammalian cells.

For generation of cell lines and selection of lead fully humanized antibodies, heavy and light chain plasmid DNA pairs are transfected into mammalian cells (NS0). Cell lines producing humanized antibodies are expanded and antibody samples are purified. Antibodies are tested in primary and secondary binding assays to determine leading antibody candidates. The 3 leading candidates are used for further analysis.

Example 13

Immunogenicity Testing

Lead antibodies are subjected to EpiScreen (Antitope, Paradise Valley, Ariz.) whole antibody human T cell assays using a minimum of 20 blood samples from healthy volunteer donors. Immunogenicity of lead antibodies is compared with control chimeric antibodies with starting antibody variable regions and matched human constant regions. Data are benchmarked against EpiScreen whole protein data for clinical-stage biologics.

Example 14

Cell Line Development

Cell lines are developed with the ability to yield high levels of antibody with no non-human glycosylation due to knock down of the CMAH gene. Cell lines are glycoengineered to increase ADCC. These cell lines have the ability to perform in small and large scale production.

Example 15

Hybridoma Formation with Group 2 Mouse #1614

Prior to the generation of hybridoma cells, mouse #1614 is provided with a final immunization comprising PSM by intravenous injection without adjuvant. Spleen cells from #1604 are fused with myeloma cell line X63-Ag8.653. Cells are plated into 96 well plates and cultured in hypoxanthine-aminopterin-thymidine (HAT) selection medium (used to kill non-fused myeloma cells). Isolated colonies are selected from the fully-fused, HAT-resistant cells that remain.

ELISA Method for Screening

Screening is carried out using de-O-acetylated bovine submaxillary mucin (BSM) as a target. The protein part of BSM differs from the PSM antigen, ensuring that anti-protein antibodies do not interfere with the assay. The glycan part of BSM is similar to PSM but has high 9-O-acetylation. ELISA plates are coated with BSM and treated to destroy 9-O-acetyl groups. Treatment is carried out with or without mild periodate to destroy the C6 side chain of BSM sialic acid, enabling the measurement of sialic acid-specific binding in the assay. Culture medium supernatant harvested from the hybridoma cultures is added to the ELISA plates and allowed to incubate for 2 hours to allow secreted antibodies to bind with the BSM. Wells are washed and secondary antibody solution is added containing anti-mouse IgG conjugated to horse radish peroxidase (HRP). Wells are again washed and incubated with HRP substrate [100 µl of substrate (TMB)/well]. Reaction with the substrate is stopped with 100 µl of 1 M HCl and wells are read spectrophotometrically at 450 nm.

Isolation of Colonies and Further Characterization

Up to 48 anti-BSM antibody-secreting preclones are isolated and further characterized by glycan array and advanced ELISA. Ranking of the best hybridoma clones is established based on the data generated. Up to 5 anti-Neu5Gc-STn antibody secreting colonies are isolated. Clones are expanded. Frozen stocks are generated.

Example 16

Mouse Immunization from Various Antigenic Sources

48 Cmah −/− mice, males and females, 8-12 weeks old are used in the present study. Food and water are provided ad libitum throughout the study period. Food provided is standard diet (2920X.10, Global 18% Protein Rodent Diet, Harlan, San Diego, Calif.) and water provided is acidified water (pH 2.7-3.0). Mice are allowed to acclimate to their surroundings for at least 3 days prior to the study period.

Mice are divided into the treatment groups and immunization regimens detailed in Table 7. Each mouse receives five immunizations, once on days 0, 14, 28, 42 and 56 of the study. Antigens are injected subcutaneously around armpits and inguinal regions (50 µl per site, 4 sites of injection and 200 µl total volume per mouse). Antigens used in the study include porcine submaxillary mucin (PSM), bovine submaxillary mucin (BSM), synthetic Neu5Gc-SialylTn (GcSTn) and synthetic Neu5Ac-SialylTn (AcSTn). BSM is de-O-acetylated prior to use. All antigens are dissolved in phosphate buffered saline. Animals are weighed and monitored for health twice per week. Blood is collected from all animals prior to immunization on days 0, 42 and 56. Approximately 0.2 ml of whole blood are collected from each animal on day 0 via facial vein bleed. Blood is collected into serum separator tubes and kept at room temperature for at least 30 minutes to allow clotting. The blood is processed to serum and stored at −80° C. until analysis.

TABLE 7

Study design

| Group #: # of Animals | Sex (F/M) and ID | Vaccination and Adjuvant | Schedule (days) | | | | |
|---|---|---|---|---|---|---|---|
| | | | 0 | 14 | 28 | 42 | 56 |
| Group 1: 12 mice | F2429; F2430; F2431; F2447; F2448; F2456; F2457 M2432; M2438; M2439; M2445; M2446 | 100 µg PSM + CFA or IFA | Pre-B, V (CFA) | V (IFA) | V (IFA) | B, V (IFA) | B, V (no adjuvant) |

TABLE 7-continued

Study design

| Group #: # of Animals | Sex (F/M) and ID | Vaccination and Adjuvant | Schedule (days) | | | | |
|---|---|---|---|---|---|---|---|
| | | | 0 | 14 | 28 | 42 | 56 |
| Group 2: 6 mice | F2450; F2451; F2452 M2453; M2454; M2455 | 10 µg Synthetic GcSTn + CFA or IFA | Pre-B, V (CFA) | V (IFA) | V (IFA) | B, V (IFA) | B, V (no adjuvant) |
| Group 3: 6 mice | F2415; F2416; F2417 M2418; M2419; M2420 | First two V days: 100 µg PSM + CFA or IFA Last three V days: 10 µg Synthetic GcSTn + CFA or IFA | Pre-B, V (CFA) | V (IFA) | V (IFA) | B, V (IFA) | B, V (no adjuvant) |
| Group 4: 12 mice | F2440; F2441; F2442; F2443; F2444; F2437 M2449; M2410; M2411; M2412; M2413; M2414 | 100 µg BSM + CFA or IFA | Pre-B, V (CFA) | V (IFA) | V (IFA) | B, V (IFA) | B, V (no adjuvant) |
| Group 5: 6 mice | F2421; F2422; F2423; F2424 M2435; M2436 | 10 µg Synthetic AcSTn + CFA or IFA | Pre-B, V (CFA) | V (IFA) | V (IFA) | B, V (IFA) | B, V (no adjuvant) |
| Group 6: 6 mice | F2433; F2434 M2425; M2426; M2427; M2428 | First two V days: 100 µg BSM + CFA or IFA Last three V days: 10 µg Synthetic AcSTn + CFA or IFA | Pre-B, V (CFA) | V (IFA) | V (IFA) | B, V (IFA) | B, V (no adjuvant) |

In Table 7,
V = vaccination;
B = bleed;
CFA = Complete Freund's Adjuvant;
IFA = Incomplete Freund's Adjuvant.

PSM contains mostly GcSTn. BSM contains both AcSTn and GcSTn. Groups 1-3 are used to generate anti-GcSTn antibodies. Groups 4-6 are used to generate anti-AcSTn antibodies. All immunization strategies have the potential to generate a pan-anti-STn antibody, with Group 4 mice being the most likely.

Identification of Anti-GcSTn Antibodies

Mouse sera are screened using de-O-acetylated BSM (+/− periodate treatment) as a target. The protein part of BSM differs from that of PSM, ensuring that anti-PSM protein antibodies will not interfere with the assay. The glycan portion of BSM is similar to PSM, but has high 9-O-acetylation and higher Neu5Ac content. ELISA plates are coated with BSM and base treated to destroy 9-O-acetylation of BSM. Optionally, some wells receive mild periodate treatment to destroy (C6 side chains) of sialic acids. This is carried out to ensure sialic acid-specific binding. Mouse sera are applied with or without 20 mM Neu5Ac or Neu5Gc to observe whether or not these compounds can compete for binding with antibodies in the sera. Only Neu5Gc competes successfully with anti-GcSTn antibodies. Plates are washed and treated for 1 hour with secondary antibody (anti-mouse IgG) conjugated to horseradish peroxidase (HRP). Plates are washed again and treated with HRP substrate. Results are determined by spectrophotometric analysis.

Sera are further assessed by glycan array according to the methods described in example 4. Sera comprising antibodies specific for GcSTn display binding to glycans corresponding to array ID #6 [Neu5Gcα2,6GalNAcαO(CH2)2CH2NH2], but not to glycans corresponding to array ID #5 [Neu5Acα2,6GalNAcαO(CH2)2CH2NH2].

Identification of Anti-AcSTn Antibodies

Mouse sera are screened using PSM (+/− periodate treatment) as a target. The protein part of BSM differs from that of PSM, ensuring that anti-BSM protein antibodies will not interfere with the assay. The glycan portion of BSM is similar to PSM, but has high 9-O-acetylation and higher Neu5Ac content. ELISA plates are coated with PSM with some wells subjected to mild periodate treatment to destroy (C6 side chains) of sialic acids. This is carried out to ensure sialic acid-specific binding. Mouse sera are applied with or without 20 mM Neu5Ac or Neu5Gc to observe whether or not these compounds can compete for binding with antibodies in the sera. Only Neu5Ac competes successfully with anti-AcSTn specific antibodies. Plates are washed and treated for 1 hour with secondary antibody (anti-mouse IgG) conjugated to horseradish peroxidase (HRP). Plates are washed again and treated with HRP substrate. Results are determined by spectrophotometric analysis.

Sera are further assessed by glycan array according to the methods described in example 4. Sera comprising antibodies specific for AcSTn display binding to glycans corresponding to array ID #5 [Neu5Acα2,6GalNAcαO(CH2)2CH2NH2], but not to glycans corresponding to array ID #6 [Neu5Gcα2,6GalNAcαO(CH2)2CH2NH2].

Identification of Pan-Anti-STn Antibodies

Mouse sera are screened using PSM (+/− periodate treatment) as a target. ELISA plates are coated with PSM with some wells subjected to mild periodate treatment to destroy (C6 side chains) of sialic acids. This is carried out to ensure sialic acid-specific binding. Mouse sera are applied with or without 20 mM Neu5Ac or Neu5Gc to observe whether or not these compounds can compete for binding with antibodies in the sera. Neu5Ac and Neu5Gc are able to compete successfully with pan-anti-STn specific antibodies. Plates are washed and treated for 1 hour with secondary antibody (anti-mouse IgG) conjugated to horseradish peroxidase (HRP). Plates are washed again and treated with HRP substrate. Results are determined by spectrophotometric analysis.

Sera are further assessed by glycan array according to the methods described in example 4. Sera comprising antibodies capable of binding to both GcSTn and AcSTn display binding to glycans corresponding to both array ID #5 [Neu5Acα2,6GalNAcαO(CH2)2CH2NH2] and array ID #6 [Neu5Gcα2,6GalNAcαO(CH2)2CH2NH2].

Hybridoma Generation

Mice from each group yielding the greatest immune response are used in the generation of hybridoma cell lines. Hybridoma generation is carried out according to the methods of Example 15.

Example 17

Hybridoma Generation and Testing

Mouse serum was isolated from the mice participating in the study detailed in Example 16 on day 126 of the study. The serum was analyzed by BSM/PSM/OSM ELISA assay to determine serum titer. Serum with the highest serum titers were also analyzed by glycan array. Glycan arrays were carried out according to the procedure of Example 4. Glycan arrays used comprised the glycans and with corresponding glycan ID numbers shown in Table 8.

TABLE 8

Glycans used in glycan arrays

| Glycan ID | Glycan |
|---|---|
| 1 | Neu5,9Ac2α2,3Galβ1,4GlcNAcβO(CH2)2CH2NH2 |
| 2 | Neu5Gc9Acα2,3Galβ1,4GlcNAcβO(CH2)2CH2NH2 |
| 3 | Neu5,9Ac2α2,6Galβ1,4GlcNAcβO(CH2)2CH2NH2 |
| 4 | Neu5Gc9Acα2,6Galβ1,4GlcNAcβO(CH2)2CH2NH2 |
| 5 | Neu5Acα2,6GalNAcαO(CH2)2CH2NH2 |
| 6 | Neu5Gcα2,6GalNAcαO(CH2)2CH2NH2 |
| 7 | Neu5,9Ac2α2,3Galβ1,3GlcNAcβO(CH2)2CH2NH2 |
| 8 | Neu5Gc9Acα2,3Galβ1,3GlcNAcβO(CH2)2CH2NH2 |
| 9 | Neu5,9Ac2α2,3Galβ1,3GalNAcαO(CH2)2CH2NH2 |
| 10 | Neu5Gc9Acα2,3Galβ1,3GalNAcαO(CH2)2CH2NH2 |
| 11 | Neu5Acα2,3Galβ1,4GlcNAcβO(CH2)2CH2NH2 |
| 12 | Neu5Gcα2,3Galβ1,4GlcNAcβO(CH2)2CH2NH2 |
| 13 | Neu5Acα2,3Galβ1,3GlcNAcβO(CH2)2CH2NH2 |
| 14 | Neu5Gcα2,3Galβ1,3GlcNAcβO(CH2)2CH2NH2 |
| 15 | Neu5Acα2,3Galβ1,3GalNAcαO(CH2)2CH2NH2 |
| 16 | Neu5Gcα2,3Galβ1,3GalNAcαO(CH2)2CH2NH2 |
| 17 | Neu5Acα2,6Galβ1,4GlcNAcβO(CH2)2CH2NH2 |
| 18 | Neu5Gcα2,6Galβ1,4GlcNAcβO(CH2)2CH2NH2 |
| 19 | Neu5Acα2,6Galβ1,4GlcβO(CH2)2CH2NH2 |
| 20 | Neu5Gcα2,6Galβ1,4GlcβO(CH2)2CH2NH2 |
| 21 | Neu5Acα2,3Galβ1,4GlcβO(CH2)2CH2NH2 |
| 22 | Neu5Gcα2,3Galβ1,4GlcβO(CH2)2CH2NH2 |
| 23 | Neu5,9Ac2α2,6GalNAcαO(CH2)2CH2NH2 |
| 24 | Neu5Gc9Acα2,6GalNAcαO(CH2)2CH2NH2 |
| 25 | Neu5Acα2,3GalβO(CH2)2CH2NH2 |
| 26 | Neu5Gcα2,3GalβO(CH2)2CH2NH2 |
| 27 | Neu5Acα2,6GalβO(CH2)2CH2NH2 |
| 28 | Neu5Gcα2,6GalβO(CH2)2CH2NH2 |
| 29 | Neu5,9Ac2α2,3GalβO(CH2)2CH2NH2 |
| 30 | Neu5Gc9Acα2,3GalβO(CH2)2CH2NH2 |
| 31 | Neu5,9Ac2α2,6GalβO(CH2)2CH2NH2 |
| 32 | Neu5Gc9Acα2,6GalβO(CH2)2CH2NH2 |
| 33 | Neu5Acα2,3Galβ1,3GalNAcβO(CH2)2CH2NH2 |
| 34 | Neu5Gcα2,3Galβ1,3GalNAcβO(CH2)2CH2NH2 |
| 35 | Neu5,9Ac2α2,3Galβ1,3GalNAcβO(CH2)2CH2NH2 |
| 36 | Neu5Gc9Acα2,3Galβ1,3GalNAcβO(CH2)2CH2NH2 |
| 37 | Neu5,9Ac2α2,6Galβ1,4GlcβO(CH2)2CH2NH2 |
| 38 | Neu5Gc9Acα2,6Galβ1,4GlcβO(CH2)2CH2NH2 |
| 39 | Neu5,9Ac2α2,3Galβ1,4GlcβO(CH2)2CH2NH2 |
| 40 | Neu5Gc9Acα2,3Galβ1,4GlcβO(CH2)2CH2NH2 |
| 41 | Neu5Acα2,8Neu5Acα2,3Galβ1,4GlcβO(CH2)2CH2NH2 |
| 42 | Neu5Acα2,8Neu5Acα2,8Neu5Acα2,3Galβ1,4GlcβO(CH2)2CH2NH2 |
| 43 | Galβ1,4GlcβO(CH2)2CH2NH2 |
| 45 | Galβ1,4GlcNAcβO(CH2)2CH2NH2 |
| 47 | GalNAcαO(CH2)2CH2NH2 |
| 51 | Galβ1,3GalNAcβO(CH2)2CH2NH2 |
| 52 | Galβ1,3GlcNAcαO(CH2)2CH2NH2 |
| 53 | Galβ1,3GlcNAcβO(CH2)2CH2NH2 |
| 54 | Galβ1,4GlcNAc6SβO(CH2)2CH2NH2 |
| 55 | Neu5Acα2,3Galβ1,4(Fucα1,3)GlcNAcβO(CH2)2CH2NH2 |
| 56 | Neu5Gcα2,3Galβ1,4(Fucα1,3)GlcNAcβO(CH2)2CH2NH2 |
| 57 | Neu5Acα2,3Galβ1,4(Fucα1,3)GlcNAc6SβO(CH2)2CH2NH2 |
| 58 | Neu5Gcα2,3Galβ1,4(Fucα1,3)GlcNAc6SβO(CH2)2CH2NH2 |
| 59 | Galβ1,3GlcNAcβ1,3Galβ1,4GlcβO(CH2)2CH2NH2 |

TABLE 8-continued

Glycans used in glycan arrays

| Glycan ID | Glycan |
|---|---|
| 60 | Neu5Acα2,3Galβ1,3GlcNAcβ1,3Galβ1,4GlcβO(CH2)2CH2NH2 |
| 61 | Neu5Gcα2,3Galβ1,3GlcNAcβ1,3Galβ1,4GlcβO(CH2)2CH2NH2 |
| 62 | Neu5Acα2,3Galβ1,4GlcNAc6SβO(CH2)2CH2NH2 |
| 63 | Neu5Gcα2,3Galβ1,4GlcNAc6SβO(CH2)2CH2NH2 |
| 64 | Neu5Acα2,8Neu5Acα2,3Galβ1,4GlcβO(CH2)3NHCOCH2(OCH2CH2)6NH2 |
| 65 | Neu5Acα2,8Neu5Acα2,8Neu5Acα2,3Galβ1,4GlcβO(CH2)3NHCOCH2(OCH2CH2)6NH2 |
| 66 | Neu5Acα2,6(Neu5Acα2,3)Galβ1,4GlcβO(CH2)2CH2NH2 |
| 67 | Neu5Acα2,6(Neu5Gcα2,3)Galβ1,4GlcβO(CH2)2CH2NH2 |
| 68 | Neu5Acα2,6(KDNα2,3)Galβ1,4GlcβO(CH2)2CH2NH2 |
| 69 | Neu5Gcα2,8Neu5Acα2,3Galβ1,4GlcβO(CH2)2CH2NH2 |
| 70 | KDNα2,8Neu5Acα2,3Galβ1,4GlcβO(CH2)2CH2NH2 |
| 71 | Neu5Acα2,8Kdnα2,6Galβ1,4GlcβO(CH2)2CH2NH2 |
| 72 | Neu5Acα2,8Neu5Gcα2,3Galβ1,4GlcβO(CH2)2CH2NH2 |
| 73 | Neu5Acα2,8Neu5Gcα2,6Galβ1,4GlcβO(CH2)2CH2NH2 |
| 74 | KDNα2,8Neu5Gcα2,3Galβ1,4GlcβO(CH2)2CH2NH2 |
| 75 | Neu5Gcα2,8Neu5Gcα2,3Galβ1,4GlcβO(CH2)2CH2NH2 |
| 76 | Neu5Acα2,8Neu5Acα2,6Galβ1,4GlcβO(CH2)2CH2NH2 |

Mouse #2429 displayed strong specificity for Neu5Gc (+90-acetylated variants.) The highest signal from the array data obtained from that sample corresponded with Neu5Gc-STn (Table 9)

TABLE 9

Glycan array results

| | Intensity by Mouse ID # | | | | | | | |
|---|---|---|---|---|---|---|---|---|
| | Avg Values | | | | Std Dev | | | |
| Glycan ID No. | #2417 | #2429 | #2444 | neg control | #2417 | #2429 | #2444 | neg control |
| 1 | 0 | 0 | 0 | 0 | 0 | 0 | 0 | 0 |
| 2 | 33550 | 18800 | 150 | 0 | 14900 | 700 | 50 | 0 |
| 3 | 0 | 0 | 0 | 0 | 350 | 0 | 0 | 0 |
| 4 | 64300 | 8650 | 150 | 0 | 2250 | 5500 | 0 | 0 |
| 5 | 100 | 50 | 700 | 0 | 250 | 0 | 50 | 0 |
| 6 | 52900 | 35450 | 2800 | 0 | 15950 | 950 | 250 | 0 |
| 7 | 0 | 0 | 700 | 0 | 0 | 100 | 1200 | 0 |
| 8 | 21100 | 6700 | 50 | 0 | 12850 | 2950 | 50 | 0 |
| 9 | 0 | 0 | 0 | 0 | 350 | 0 | 0 | 0 |
| 10 | 9300 | 800 | 0 | 0 | 1150 | 100 | 0 | 0 |
| 11 | 0 | 0 | 0 | 0 | 350 | 100 | 0 | 0 |
| 12 | 10000 | 13250 | 100 | 0 | 1650 | 800 | 50 | 0 |
| 13 | 0 | 50 | 0 | 0 | 200 | 100 | 0 | 50 |
| 14 | 28000 | 16200 | 100 | 0 | 12300 | 5450 | 50 | 0 |
| 15 | 0 | 0 | 0 | 0 | 100 | 0 | 0 | 50 |
| 16 | 4850 | 5050 | 100 | 0 | 1050 | 1400 | 100 | 0 |
| 17 | 0 | 50 | 0 | 0 | 350 | 100 | 0 | 0 |
| 18 | 22600 | 17200 | 200 | 0 | 6350 | 4450 | 0 | 0 |
| 19 | 0 | 150 | 0 | 0 | 0 | 150 | 0 | 50 |
| 20 | 66900 | 12800 | 400 | 0 | 5450 | 4950 | 0 | 100 |
| 21 | 0 | 50 | 0 | 0 | 0 | 100 | 0 | 0 |
| 22 | 32500 | 7650 | 100 | 50 | 1300 | 1000 | 50 | 50 |
| 23 | 0 | 50 | 350 | 0 | 0 | 50 | 0 | 0 |
| 24 | 53800 | 10250 | 2050 | 0 | 10900 | 3850 | 300 | 0 |
| 25 | 0 | 50 | 0 | 50 | 0 | 50 | 0 | 50 |
| 26 | 47350 | 16700 | 600 | 0 | 3150 | 300 | 50 | 0 |
| 27 | 0 | 0 | 50 | 0 | 0 | 0 | 50 | 0 |
| 28 | 48600 | 14450 | 950 | 0 | 9900 | 1100 | 50 | 0 |
| 29 | 0 | 0 | 0 | 0 | 0 | 0 | 0 | 0 |
| 30 | 47500 | 19400 | 600 | 0 | 8550 | 1650 | 100 | 0 |
| 31 | 0 | 0 | 150 | 0 | 0 | 0 | 50 | 0 |
| 32 | 58450 | 21550 | 450 | 0 | 8300 | 7800 | 50 | 0 |
| 33 | 0 | 0 | 0 | 50 | 0 | 150 | 0 | 150 |
| 34 | 27500 | 11900 | 100 | 0 | 1650 | 1050 | 0 | 0 |
| 35 | 0 | 0 | 50 | 0 | 200 | 0 | 50 | 0 |
| 36 | 10600 | 3550 | 150 | 0 | 1900 | 600 | 100 | 100 |
| 37 | 0 | 0 | 0 | 0 | 0 | 600 | 0 | 0 |
| 38 | 50950 | 7150 | 150 | 0 | 8050 | 1850 | 50 | 0 |

TABLE 9-continued

Glycan array results

Intensity by Mouse ID #

| | Avg Values | | | | Std Dev | | | |
|---|---|---|---|---|---|---|---|---|
| Glycan ID No. | #2417 | #2429 | #2444 | neg control | #2417 | #2429 | #2444 | neg control |
| 39 | 0 | 0 | 0 | 0 | 0 | 50 | 0 | 0 |
| 40 | 18300 | 4350 | 0 | 0 | 850 | 1250 | 0 | 0 |
| 41 | 0 | 50 | 0 | 0 | 0 | 50 | 0 | 0 |
| 42 | 0 | 0 | 0 | 0 | 0 | 0 | 0 | 0 |
| 43 | 0 | 0 | 0 | 0 | 0 | 250 | 0 | 50 |
| 45 | 0 | 50 | 0 | 0 | 0 | 50 | 0 | 0 |
| 47 | 0 | 50 | 50 | 0 | 0 | 0 | 0 | 0 |
| 51 | 0 | 50 | 0 | 0 | 0 | 100 | 0 | 0 |
| 52 | 0 | 100 | 0 | 0 | 0 | 150 | 0 | 0 |
| 53 | 0 | 50 | 100 | 0 | 0 | 50 | 100 | 0 |
| 54 | 0 | 0 | 300 | 0 | 0 | 0 | 100 | 0 |
| 55 | 0 | 0 | 300 | 0 | 0 | 0 | 50 | 0 |
| 56 | 25350 | 7700 | 150 | 0 | 250 | 3200 | 50 | 0 |
| 57 | 0 | 50 | 150 | 0 | 0 | 0 | 50 | 0 |
| 58 | 66450 | 31600 | 450 | 0 | 2650 | 6100 | 50 | 0 |
| 59 | 50 | 0 | 150 | 0 | 100 | 0 | 50 | 0 |
| 60 | 0 | 50 | 0 | 0 | 200 | 150 | 0 | 0 |
| 61 | 3250 | 500 | 0 | 50 | 300 | 150 | 0 | 50 |
| 62 | 0 | 0 | 0 | 50 | 0 | 0 | 0 | 50 |
| 63 | 33850 | 29800 | 1250 | 0 | 3050 | 6400 | 50 | 0 |
| 64 | 0 | 50 | 0 | 50 | 0 | 50 | 0 | 50 |
| 65 | 0 | 0 | 0 | 0 | 0 | 0 | 0 | 50 |
| 66 | 100 | 0 | 0 | 0 | 100 | 100 | 0 | 50 |
| 67 | 38200 | 24650 | 500 | 50 | 4750 | 1300 | 50 | 150 |
| 68 | 0 | 0 | 0 | 0 | 0 | 0 | 0 | 50 |
| 69 | 4150 | 2750 | 0 | 50 | 1950 | 1000 | 0 | 0 |
| 70 | 0 | 0 | 0 | 50 | 0 | 0 | 0 | 50 |
| 71 | 0 | 0 | 0 | 50 | 0 | 0 | 0 | 50 |
| 72 | 0 | 100 | 550 | 0 | 250 | 150 | 300 | 0 |
| 73 | 0 | 0 | 600 | 0 | 0 | 50 | 350 | 0 |
| 74 | 100 | 200 | 50 | 0 | 0 | 350 | 100 | 0 |
| 75 | 6350 | 4650 | 550 | 0 | 550 | 1450 | 200 | 0 |
| 76 | 0 | 0 | 0 | 0 | 0 | 0 | 250 | 0 |

Mouse #2429 along with two other mice (#2417 and #2444) with the best serum titers were selected for hybridoma generation. Mice #2429 and #2417 had received PSM immunizations (to yield an anti-Neu5Gc response), while mouse #2444 had received BSM immunizations (to yield an anti-Neu5Ac-STn response.) For each mouse, 5×96-well fusion plates were prepared per myeloma (F0 and P3X63Ag8U.1) and fused with splenocytes from each mouse. Fused cells were cultured in selection media to support only fully fused cells.

Next, 20 fully fused clones were selected for screening. Clones derived from #2417 and #2429 were screened by BSM ELISA assay, while clones derived from #2444 were screened by PSM and OSM ELISA assay. Screening by BSM ELISA was carried out using de-O-acetylated bovine submaxillary mucin (BSM) as a target. The protein part of BSM differs from the PSM antigen, ensuring that anti-protein antibodies do not interfere with the assay. The glycan part of BSM is similar to PSM but has high 9-O-acetylation. ELISA plates were coated with BSM and treated to destroy 9-O-acetyl groups. Treatment was carried out with or without mild periodate to destroy the C6 side chain of BSM sialic acid, enabling the measurement of sialic acid-specific binding in the assay. Culture medium supernatant harvested from the hybridoma cultures was added to the ELISA plates and allowed to incubate for 2 hours to allow secreted antibodies to bind with the BSM. Incubation with mouse anti-STn antibody was carried out in additional wells as a positive control. Pooled naïve CMAH−/− mouse serum was used as a negative control. Hybridoma media alone was used to measure background at a 1:2 dilution factor.

Wells were washed and secondary antibody solution was added containing anti-mouse IgG conjugated to horse radish peroxidase (HRP). Wells were again washed and incubated with HRP substrate [100 μl of substrate (TMB)/well]. Reaction with the substrate was stopped with 100 μl of 1 M HCl and wells were read spectrophotometrically at 490 nm. Optical density values adjusted against blank well readings are presented in Table 10.

TABLE 10

BSM ELISA results

| Mouse ID # | Clone # | OD 490 nm |
|---|---|---|
| 2417 | 3A7 | 0.118 |
| 2417 | 3A10 | 0.104 |
| 2417 | 4G12 | 0.078 |
| 2417 | 10C7 | 0.129 |
| 2429 | 1A8 | 0.070 |
| 2429 | 2B2 | 2.934 |
| 2429 | 2C2 | 1.228 |
| 2429 | 2D2 | 0.285 |
| 2429 | 2E2 | 0.210 |
| 2429 | 2F2 | 0.104 |
| 2429 | 2G2 | 0.054 |

TABLE 10-continued

BSM ELISA results

| Mouse ID # | Clone # | OD 490 nm |
|---|---|---|
| 2429 | 2G9 | 0.056 |
| 2429 | 2H11 | 0.062 |
| 2429 | 3H12 | 0.115 |
| 2429 | 5D2 | 0.055 |
| 2429 | 5D3 | 0.054 |
| 2429 | 5E4 | 0.061 |
| 2429 | 5E5 | 0.054 |
| 2429 | 9H5 | 0.221 |
| 2429 | 10C10 | 0.069 |

Hybridoma clone 2B2 showed positive results by ELISA and was selected for expansion. Subclones 1A12-2B2, 1B10-2B2, 1C12-2B2, 1D4-2B2, 1E10-2B2 and 2A5-2B2 were cultured and antibodies secreted from those clones were analyzed by glycan array. Results of the array are shown in Table 11. In the table, "Glycan ID is indicated by "GID."

TABLE 11

Glycan array results for 2B2 subclones

Intensity by subclone ID

| | Avg Intensity | | | | | | | Std Dev | | | | | | | |
|---|---|---|---|---|---|---|---|---|---|---|---|---|---|---|---|
| GID | Anti-STn | Normal IgG | 1A12 | 1B10 | 1C12 | 1D4 | 1E10 | 2A5 | Anti-STn | Normal IgG | 1A12 | 1B10 | 1C12 | 1D4 | 1E10 | 2A5 |
| 4 | 0 | 50 | 3000 | 850 | 2900 | 800 | 1750 | 1300 | 0 | 0 | 750 | 100 | 600 | 150 | 450 | 450 |
| 5 | 550 | 0 | 0 | 0 | 0 | 0 | 0 | 0 | 50 | 0 | 0 | 0 | 0 | 0 | 0 | 0 |
| 6 | 150 | 0 | 400 | 100 | 350 | 150 | 200 | 150 | 0 | 0 | 50 | 0 | 100 | 50 | 50 | 50 |
| 11 | 50 | 150 | 0 | 0 | 0 | 0 | 0 | 0 | 0 | 50 | 0 | 0 | 0 | 0 | 0 | 0 |
| 12 | 0 | 0 | 0 | 0 | 0 | 50 | 0 | 0 | 0 | 0 | 0 | 0 | 0 | 50 | 0 | 0 |
| 13 | 50 | 0 | 0 | 0 | 0 | 0 | 0 | 0 | 50 | 0 | 0 | 0 | 0 | 0 | 0 | 0 |
| 17 | 0 | 0 | 50 | 0 | 50 | 0 | 0 | 0 | 0 | 0 | 0 | 0 | 0 | 0 | 0 | 0 |
| 18 | 0 | 100 | 3900 | 850 | 3750 | 1500 | 3000 | 1700 | 0 | 0 | 550 | 50 | 250 | 150 | 500 | 150 |
| 20 | 0 | 0 | 900 | 150 | 900 | 300 | 450 | 300 | 0 | 0 | 200 | 50 | 100 | 50 | 100 | 50 |
| 23 | 150 | 0 | 0 | 0 | 0 | 0 | 0 | 0 | 50 | 0 | 0 | 0 | 0 | 0 | 0 | 0 |
| 24 | 150 | 0 | 250 | 50 | 150 | 50 | 50 | 50 | 0 | 0 | 100 | 0 | 0 | 0 | 0 | 0 |
| 27 | 0 | 0 | 50 | 0 | 50 | 0 | 0 | 0 | 0 | 0 | 0 | 0 | 0 | 0 | 0 | 0 |
| 28 | 0 | 50 | 2350 | 500 | 1100 | 650 | 750 | 800 | 0 | 0 | 50 | 100 | 500 | 100 | 150 | 200 |
| 32 | 0 | 50 | 2900 | 250 | 1550 | 700 | 1300 | 800 | 0 | 0 | 1000 | 50 | 650 | 100 | 50 | 400 |
| 38 | 0 | 0 | 250 | 0 | 300 | 50 | 100 | 0 | 0 | 0 | 50 | 0 | 50 | 50 | 50 | 0 |
| 45 | 0 | 0 | 0 | 0 | 50 | 0 | 0 | 0 | 0 | 0 | 0 | 0 | 50 | 0 | 0 | 0 |
| 54 | 50 | 0 | 0 | 0 | 0 | 0 | 0 | 0 | 50 | 0 | 0 | 0 | 0 | 0 | 0 | 0 |
| 69 | 0 | 0 | 0 | 0 | 0 | 0 | 50 | 0 | 0 | 0 | 0 | 0 | 0 | 0 | 50 | 0 |

Glycan array results for 1A12-2B2 indicated that antibodies secreted by that clone have strong specificity for Neu5Gcα2,6Gal (glycans 6, 18, 20 and 28 on the glycan array) as well as +9O-acetylated variants (glycans 4, 24, 32 and 38 on the glycan array.) Based on these results, antibodies produced by 1A12-2B2 as well as their corresponding genes were sequenced. The amino acid sequences corresponding to the heavy and light chain variable domains are listed in Table 12. CDR regions include amino acids that are underlined and in bold.

TABLE 12

Variable domain amino acid sequences for clone 1A12-2B2 antibodies

| Sequence type | Sequence | SEQ ID NO |
|---|---|---|
| V_H domain amino acids | QVQLKESGPGLVAPSQSLSITCTVSGFSLTSYGVSWVRQPP GKGLEWLGVIWGDGSTNYHSALISRLSISKDNSKSQVFLKL NSLQTDDTATYYCAKGGYFDYWGQGTTLTVSS | 1 |
| V_L domain amino acids | QIVLTQSPAVMSASPGEKVAITCSASSSVSYMHWFQQKPGT SPKLWIYSTSNLASGVPARFSGSGSGTSYSLTISRMEAEDAA TYYCQQRSSYPWTFGGGTKLEIK | 2 |
| V_H domain nucleotide sequence | CAGGTGCAGCTGAAGGAGTCAGGACCTGGCCTGGTGGCG CCCTCACAGAGCCTGTCCATCACATGCACTGTCTCAGGGT TCTCATTAACCAGCTATGGTGTAAGCTGGGTTCGCCAGCC | 3 |

TABLE 12-continued

Variable domain amino acid sequences for clone 1A12-2B2 antibodies

| Sequence type | Sequence | SEQ ID NO |
|---|---|---|
| | TCCAGGAAAGGGTCTGGAGTGGCTGGGAGTAATATGGGG<br>TGACGGGAGCACAAATTATCATTCAGCTCTCATATCCAG<br>ACTGAGCATCAGCAAGGATAACTCCAAGAGCCAAGTTTT<br>CTTAAAACTGAACAGTCTGCAAACTGATGACACAGCCAC<br>GTACTACTGTGCCAAAGGGGCTACTTTGACTACTGGGG<br>CCAAGGCACCACTCTCACAGTCTCCTCA | |
| V$_L$ domain nucleotide sequence | CAAATTGTTCTCACCCAGTCTCCAGCAGTCATGTCTGCAT<br>CTCCAGGGGAGAAGGTCGCCATAACCTGCAGTGCCAGCT<br>CAAGTGTAAGTTACATGCACTGGTTCCAGCAGAAGCCAG<br>GCACTTCTCCCAAACTCTGGATTTATAGCACATCCAACCT<br>GGCTTCTGGAGTCCCTGCTCGCTTCAGTGGCAGTGGATCT<br>GGGACCTCTTACTCTCTCACAATCAGCCGAATGGAGGCT<br>GAAGATGCTGCCACTTATTACTGCCAGCAAAGGAGTAGT<br>TACCCGTGGACGTTCGGTGGAGGCACCAAGCTGGAAATC<br>AAAC | 4 |

The invention claimed is:

1. An antibody comprising a heavy chain variable domain (VH) comprising the amino acid sequence of SEQ ID NO: 1 and a light chain variable domain (VL) comprising the amino acid sequence of SEQ ID NO: 2.

2. A humanized antibody comprising a VH comprising the complimentarity determining regions (CDRs) of the VH domain of SEQ ID NO: 1 and a VL comprising the CDRs of the VL domain of SEQ ID NO: 2.

3. A composition comprising the antibody of claim 1 or 2 and an excipient.

* * * * *